United States Patent
Scott et al.

(10) Patent No.: US 9,902,727 B2
(45) Date of Patent: *Feb. 27, 2018

(54) AMINOALCOHOL SUBSTITUTED 2,3-DIHYDROIMIDAZO[1,2-C]QUINAZOLINE DERIVATIVES USEFUL FOR TREATING HYPER-PROLIFERATIVE DISORDERS AND DISEASES ASSOCIATED WITH ANGIOGENESIS

(71) Applicant: Bayer Intellectual Property GmbH, Monheim (DE)

(72) Inventors: William Scott, Guilford, CT (US); Ningshu Liu, Berlin (DE); Manfred Möwes, Berlin (DE); Andrea Hägebarth, Berlin (DE); Ursula Mönning, Woltersdorf (DE); Ulf Bömer, Glienicke (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,280

(22) Filed: Nov. 25, 2014

(65) Prior Publication Data

US 2015/0080374 A1 Mar. 19, 2015

Related U.S. Application Data

(63) Continuation of application No. 13/885,122, filed as application No. PCT/EP2011/069637 on Nov. 8, 2011, now Pat. No. 8,895,549.

(60) Provisional application No. 61/412,556, filed on Nov. 11, 2010.

(51) Int. Cl.

| C07D 487/04 | (2006.01) |
|---|---|
| A61K 31/519 | (2006.01) |
| A61K 45/06 | (2006.01) |
| A61K 31/5377 | (2006.01) |
| A61K 31/5386 | (2006.01) |
| A61K 31/541 | (2006.01) |
| C07D 498/08 | (2006.01) |
| C07D 471/04 | (2006.01) |

(52) U.S. Cl.
CPC .......... *C07D 487/04* (2013.01); *A61K 31/519* (2013.01); *A61K 31/5377* (2013.01); *A61K 31/5386* (2013.01); *A61K 31/541* (2013.01); *A61K 45/06* (2013.01); *C07D 471/04* (2013.01); *C07D 498/08* (2013.01)

(58) Field of Classification Search
CPC ..... C07D 487/04; A61K 31/519; A61K 45/06
See application file for complete search history.

(56) References Cited

U.S. PATENT DOCUMENTS

| 8,466,283 | B2 | 6/2013 | Hentemann et al. |
|---|---|---|---|
| 8,895,549 | B2* | 11/2014 | Scott ................ C07D 487/04 514/233.2 |
| 2011/0251191 | A1 | 10/2011 | Liu et al. |
| 2013/0261113 | A1 | 10/2013 | Hentemann et al. |
| 2013/0330327 | A1 | 12/2013 | Scott et al. |

FOREIGN PATENT DOCUMENTS

| WO | WO-1995019346 | 7/1995 | |
|---|---|---|---|
| WO | WO-1997033889 | 9/1997 | |
| WO | WO-2004029055 | 4/2004 | |
| WO | WO-2005028469 | 3/2005 | |
| WO | WO-2008014822 | 2/2008 | |
| WO | WO 2008/070150 | * 6/2008 | ............ A01N 43/54 |
| WO | WO-2009152868 | 12/2009 | |
| WO | WO-2009156315 | 12/2009 | |
| WO | WO-2010034414 | 4/2010 | |
| WO | WO-2011128407 | 10/2011 | |

OTHER PUBLICATIONS

West, Anthony R., Solid State Chemistry and Its Applications, Wiley, New York, 1988, 358.*
International Search Report dated Feb. 20, 2012 for PCT Application No. PCT/EP2011/069637 filed Nov. 8, 2011, 5 pages.
Opposition to Ecuador application SP-13-12618, received Jul. 10, 2014.
West, A.R., *Solid State Chemistry and Its Applications*, Wiley, New York, 1988, 358.

* cited by examiner

*Primary Examiner* — Erich A Leeser
(74) *Attorney, Agent, or Firm* — Morrison & Foerster LLP

(57) ABSTRACT

This invention relates to novel 2,3-dihydroimidazo[1,2-c] quinazoline compounds, pharmaceutical compositions containing such compounds and the use of those compounds or compositions for phosphotidylinositol-3-kinase (PI3K) inhibition and treating diseases associated with phosphotidylinositol-3-kinase (PI3K) activity, in particular treating hyper-proliferative and/or angiogenesis disorders, as a sole agent or in combination with other active ingredients.

15 Claims, No Drawings

AMINOALCOHOL SUBSTITUTED 2,3-DIHYDROIMIDAZO[1,2-C]QUINAZOLINE DERIVATIVES USEFUL FOR TREATING HYPER-PROLIFERATIVE DISORDERS AND DISEASES ASSOCIATED WITH ANGIOGENESIS

CROSS REFERENCE TO RELATED APPLICATIONS

This application is a continuation application of U.S. patent application Ser. No. 13/885,122, which adopts the international filing date Nov. 8, 2011, now U.S. Pat. No. 8,895,549, which is the National Phase application under 35 U.S.C. § 371 of International Application No. PCT/EP2011/069637, filed Nov. 8, 2011, which claims the benefit of U.S. Provisional Application No. 61/412,556, filed Nov. 11, 2010, the disclosures of each of which are hereby incorporated by reference in their entireties for all purposes.

FIELD OF THE INVENTION

The present invention relates to arylaminoalcohol-substituted 2,3-dihydroimidazo[1,2-c]quinolines, (hereinafter referred to as "compounds of general formula (I)") as described and defined herein, to methods of preparing said compounds, to intermediates for the preparation of said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

BACKGROUND OF THE INVENTION

In the last decade the concept of developing anti-cancer medications which target abnormally active protein kinases has led to a number of successes. In addition to the actions of protein kinases, lipid kinases also play an important role in generating critical regulatory second messengers. The PI3K family of lipid kinases generates 3'-phosphoinositides that bind to and activate a variety of cellular targets, initiating a wide range of signal transduction cascades (Vanhaesebroeck et al., 2001; Toker, 2002; Pendaries et al., 2003; Downes et al., 2005). These cascades ultimately induce changes in multiple cellular processes, including cell proliferation, cell survival, differentiation, vesicle trafficking, migration, and chemotaxis.

PI3Ks can be divided into three distinct classes based upon differences in both structure, and substrate preference. While members of the Class II family of PI3Ks have been implicated in the regulation of tumor growth (Brown & Shepherd, 2001; Traer et al., 2006), the bulk of research has focused on the Class I enzymes and their role in cancer (Stauffer et al., 2005; Stephens et al., 2005; Vivanco & Sawyers, 2002; Workman, 2004; Chen et al., 2005; Hennessy et al., 2005; Cully et al., 2006).

Class I PI3Ks have traditionally been divided into two distinct sub-classes based upon differences in protein subunit composition. The Class $I_A$ PI3Ks are comprised of a catalytic p110 catalytic subunit (p110α, β or δ) heterodimerized with a member of the p85 regulatory subunit family. In contrast, the Class $I_B$ PI3K catalytic subunit (p110γ) heterodimerizes with a distinct p101 regulatory subunit (reviewed by Vanhaesebroeck & Waterfield, 1999; Funaki et al., 2000; Katso et al., 2001). The C-terminal region of these proteins contains a catalytic domain that possesses distant homology to protein kinases. The PI3Kγ structure is similar to Class $I_A$ p110s, but lacks the N-terminal p85 binding site (Domin & Waterfield, 1997). Though similar in overall structure, the homology between catalytic p110 subunits is low to moderate. The highest homology between the PI3K isoforms is in the kinase pocket of the kinase domain.

The Class $I_A$ PI3K isoforms associate with activated receptor tyrosine kinases (RTKs) (including PDGFR, EGFR, VEGFR, IGF1-R, c-KIT, CSF—R and Met), or with tyrosine phosphorylated adapter proteins (such as Grb2, Cbl, IRS-1 or Gab1), via their p85 regulatory subunits resulting in stimulation of the lipid kinase activity. Activation of the lipid kinase activity of the p110β and p110γ isoforms has been shown to occur in response to binding to activated forms of the ras Oncogene (Kodaki et al., 1994). In fact, the oncogenic activity of these isoforms may require binding to ras (Kang et al., 2006). In contrast, the p110α and p110δ isoforms exhibit oncogenic activity independent of ras binding, through constitutive activation of Akt.

Class I PI3Ks catalyze the conversion of $PI(4,5)P_2$ [$PIP_2$] to $PI(3,4,5)P_3$ [$PIP_3$]. The production of $PIP_3$ by PI3K affects multiple signaling processes that regulate and coordinate the biological end points of cell proliferation, cell survival, differentiation and cell migration. $PIP_3$ is bound by Pleckstrin-Homology (PH) domain-containing proteins, including the phosphoinositide-dependent kinase, PDK1 and the Akt proto-oncogene product, localizing these proteins in regions of active signal transduction and also contributing directly to their activation (Klippel et al., 1997; Fleming et al., 2000; Itoh & Takenawa, 2002; Lemmon, 2003). This co-localization of PDK1 with Akt facilitates the phosphorylation and activation of Akt. Carboxy-terminal phosphorylation of Akt on $Ser^{473}$ promotes phosphorylation of $Thr^{308}$ in the Akt activation loop (Chan & Tsichlis, 2001; Hodgkinson et al., 2002; Scheid et al., 2002; Hresko et al., 2003). Once active, Akt phosphorylates and regulates multiple regulatory kinases of pathways that directly influence cell cycle progression and cell survival.

Many of the effects of Akt activation are mediated via its negative regulation of pathways which impact cell survival and which are commonly dysregulated in cancer. Akt promotes tumor cell survival by regulating components of the apoptotic and cell cycle machinery. Akt is one of several kinases that phosphorylate and inactivate pro-apoptotic BAD proteins (del Peso et al., 1997; Pastorino et al., 1999). Akt may also promote cell survival through blocking cytochrome C-dependent caspase activation by phosphorylating Caspase 9 on $Ser^{196}$ (Cardone et al., 1998).

Akt impacts gene transcription on several levels. The Akt-mediated phosphorylation of the MDM2 E3 ubiquitin ligase on $Ser^{166}$ and $Ser^{186}$ facilitates the nuclear import of MDM2 and the formation and activation of the ubiquitin ligase complex. Nuclear MDM2 targets the p53 tumor suppressor for degradation, a process that can be blocked by LY294002 (Yap et al., 2000; Ogawara et al., 2002). Down-regulation of p53 by MDM2 negatively impacts the transcription of p53-regulated pro-apoptotic genes (e.g. Bax, Fas, PUMA and DR5), the cell cycle inhibitor, $p21^{Cip1}$, and the PTEN tumor suppressor (Momand et al., 2000; Hupp et al., 2000; Mayo et al., 2002; Su et al., 2003). Similarly, the Akt-mediated phosphorylation of the Forkhead transcription factors FKHR, FKHRL and AFX (Kops et al., 1999; Tang et al., 1999), facilitates their binding to 14-3-3 proteins and export from the cell nucleus to the cytosol (Brunet et al., 1999). This functional inactivation of Forkhead activity also impacts pro-apoptotic and pro-angiogenic gene transcription including the transcription of Fas ligand (Ciechomska et al., 2003) Bim, a pro-apoptotic Bcl-2 family member (Dijkers et al., 2000), and the Angiopoietin-1 (Ang-1) antagonist, Ang-2 (Daly et al., 2004). Forkhead transcription factors regulate the expression of the cyclin-dependent kinase (Cdk) inhibitor p27$^{Kip1}$. Indeed, PI3K inhibitors have been demonstrated to induce p27$^{Kip1}$ expression resulting in Cdk1 inhibition, cell cycle arrest and apoptosis (Dijkers et al., 2000). Akt is also reported to phosphorylate p21$^{Cip1}$ on Thr$^{145}$ and p27$^{Kip1}$ on Thr$^{157}$ facilitating their association with 14-3-3 proteins, resulting in nuclear export and cytoplasmic retention, preventing their inhibition of nuclear Cdks (Zhou et al., 2001; Motti et al., 2004; Sekimoto et al., 2004). In addition to these effects, Akt phosphorylates IKK (Romashkova & Makarov, 1999), leading to the phosphorylation and degradation of IκB and subsequent nuclear translocation of NFκB, resulting in the expression of survival genes such as IAP and Bcl-X$_L$.

The PI3K/Akt pathway is also linked to the suppression of apoptosis through the JNK and p38$^{MAPK}$ MAP Kinases that are associated with the induction of apoptosis. Akt is postulated to suppress JNK and p38$^{MAPK}$ signaling through the phosphorylation and inhibition of two JNK/p38 regulatory kinases, Apoptosis Signal-regulating Kinase 1 (ASK1) (Kim et al., 2001; Liao & Hung, 2003; Yuan et al., 2003), and Mixed Lineage Kinase 3 (MLK3) (Lopez-Ilasaca et al., 1997; Barthwal et al., 2003; Figueroa et al., 2003). The induction of p38$^{MAPK}$ activity is observed in tumors treated with cytotoxic agents and is required for those agents to induce cell death (reviewed in Olson & Hallahan, 2004). Thus, inhibitors of the PI3K pathway may promote the activities of co-administered cytotoxic drugs.

An additional role for PI3K/Akt signaling involves the regulation of cell cycle progression through modulation of Glycogen Synthase Kinase 3 (GSK3) activity. GSK3 activity is elevated in quiescent cells, where it phosphorylates cyclin D$_1$ on Ser$^{286}$, targeting the protein for ubiquitination and degradation (Diehl et al., 1998) and blocking entry into S-phase. Akt inhibits GSK3 activity through phosphorylation on Ser$^9$ (Cross et al., 1995). This results in the elevation of Cyclin D$_1$ levels which promotes cell cycle progression. Inhibition of GSK3 activity also impacts cell proliferation through activation of the wnt/beta-catenin signaling pathway (Abbosh & Nephew, 2005; Naito et al., 2005; Wilker et al., 2005; Segrelles et al., 2006). Akt mediated phosphorylation of GSK3 results in stabilization and nuclear localization of the beta-catenin protein, which in turn leads to increased expression of c-myc and cyclin D1, targets of the beta-catenin/Tcf pathway.

Although PI3K signaling is utilized by many of the signal transduction networks associated with both oncogenes and tumor suppressors, PI3K and its activity have been linked directly to cancer. Overexpression of both the p110α and p110 isoforms has been observed in bladder and colon tumors and cell lines, and overexpression generally correlates with increased PI3K activity (Bénistant et al., 2000). Overexpression of p110α□□ has also been reported in ovarian and cervical tumors and tumor cell lines, as well as in squamous cell lung carcinomas. The overexpression of p110α in cervical and ovarian tumor lines is associated with increased PI3K activity (Shayesteh et al., 1999; Ma et al., 2000). Elevated PI3K activity has been observed in colorectal carcinomas (Phillips et al., 1998) and increased expression has been observed in breast carcinomas (Gershtein et al., 1999).

Over the last few years, somatic mutations in the gene encoding p110α (PIK3CA) have been identified in numerous cancers. The data collected to date suggests that PIK3CA is mutated in approximately 32% of colorectal cancers (Samuels et al., 2004; Ikenoue et al., 2005), 18-40% of breast cancers (Bachman et al., 2004; Campbell et al., 2004; Levine et al., 2005; Saal et al., 2005; Wu et al., 2005), 27% of glioblastomas (Samuels et al., 2004; Hartmann et al., 2005; Gallia et al., 2006), 25% of gastric cancers (Samuels et al., 2004; Byun et al., 2003; Li et al., 2005), 36% of hepatocellular carcinomas (Lee et al., 2005), 4-12% of ovarian cancers (Levine et al., 2005; Wang et al., 2005), 4% of lung cancers (Samuels et al., 2004; Whyte & Holbeck, 2006), and up to 40% of endometrial cancers (Oda et al., 2005). PIK3CA mutations have been reported in oligodendroma, astrocytoma, medulloblastoma, and thyroid tumors as well (Broderick et al., 2004; Garcia-Rostan et al., 2005). Based upon the observed high frequency of mutation, PIK3CA is one of the two most frequently mutated genes associated with cancer, the other being K-ras. More than 80% of the PIK3CA mutations cluster within two regions of the protein, the helical (E545K) and catalytic (H1047R) domains. Biochemical analysis and protein expression studies have demonstrated that both mutations lead to increased constitutive p110α catalytic activity and are in fact, oncogenic (Bader et al., 2006; Kang et al., 2005; Samuels et al., 2005; Samuels & Ericson, 2006). Recently, it has been reported that PIK3CA knockout mouse embryo fibroblasts are deficient in signaling downstream from various growth factor receptors (IGF-1, Insulin, PDGF, EGF), and are resistant to transformation by a variety of oncogenic RTKs (IGFR, wild-type EGFR and somatic activating mutants of EGFR, Her2/Neu) (Zhao et al., 2006).

Functional studies of PI3K in vivo have demonstrated that siRNA-mediated downregulation of p110β inhibits both Akt phosphorylation and HeLa cell tumor growth in nude mice (Czauderna et al., 2003). In similar experiments, siRNA-mediated downregulation of p110β was also shown to inhibit the growth of malignant glioma cells in vitro and in vivo (Pu et al., 2006). Inhibition of PI3K function by dominant-negative p85 regulatory subunits can block mitogenesis and cell transformation (Huang et al., 1996; Rahimi et al., 1996). Several somatic mutations in the genes encoding the p85α and p85β regulatory subunits of PI3K that result in elevated lipid kinase activity have been identified in a number of cancer cells as well (Janssen et al., 1998; Jimenez et al., 1998; Philp et al., 2001; Jucker et al., 2002; Shekar et al., 2005). Neutralizing PI3K antibodies also block mitogenesis and can induce apoptosis in vitro (Roche et al., 1994; Roche et al., 1998; Bénistant et al., 2000). In vivo proof-of-principle studies using the PI3K inhibitors LY294002 and wortmannin, demonstrate that inhibition of PI3K signaling slows tumor growth in vivo (Powis et al., 1994; Schultz et al., 1995; Semba et al., 2002; Ihle et al., 2004).

Overexpression of Class I PI3K activity, or stimulation of their lipid kinase activities, is associated with resistance to both targeted (such as imatinib and tratsuzumab) and cytotoxic chemotherapeutic approaches, as well as radiation therapy (West et al., 2002; Gupta et al., 2003; Osaki et al., 2004; Nagata et al., 2004; Gottschalk et al., 2005; Kim et al., 2005). Activation of PI3K has also been shown to lead to expression of multidrug resistant protein-1 (MRP-1) in prostate cancer cells and the subsequent induction of resistance to chemotherapy (Lee et al., 2004).

The importance of PI3K signaling in tumorigenesis is further underscored by the findings that the PTEN tumor suppressor, a PI(3)P phosphatase, is among the most commonly inactivated genes in human cancers (Li et al., 1997; Steck et al., 1997; Ali et al., 1999; Ishii et al., 1999). PTEN dephosphorylates PI(3,4,5)P$_3$ to PI(4,5)P$_2$ thereby antagonizing PI3K-dependent signaling. Cells containing functionally inactive PTEN have elevated levels of PIP$_3$, high levels of activity of PI3K signaling (Haas-Kogan et al., 1998; Myers et al., 1998; Taylor et al., 2000), increased proliferative potential, and decreased sensitivity to pro-apoptotic stimuli (Stambolic et al., 1998). Reconstitution of a functional PTEN suppresses PI3K signaling (Taylor et al., 2000), inhibits cell growth and re-sensitizes cells to pro-apoptotic stimuli (Myers et al., 1998; Zhao et al., 2004). Similarly, restoration of PTEN function in tumors lacking functional PTEN inhibits tumor growth in vivo (Stahl et al., 2003; Su et al., 2003; Tanaka & Grossman, 2003) and sensitizes cells to cytotoxic agents (Tanaka & Grossman, 2003).

The signaling inputs to Class I PI3Ks are diverse and can be deduced through genetic analyses. Thus, activation of AKT was impaired in p110α-deficient murine embryonic fibroblasts (MEFs) upon stimulation by classical Receptor Tyrosine Kinase (RTK) ligands (e.g., EGF, insulin, IGF-1, and PDGF) (Zhao et al., 2006). However, MEFs in which p110β is ablated or replaced by a kinase-dead allele of p110β respond normally to growth factor stimulation via RTKs (Jia et al., 2008). In contrast, p110β catalytic activity is required for AKT activation in response to GPCR ligands (such as LPA). As such, p110α appears to carry the majority of the PI3K signal in classic RTK signaling and is responsible for tumor cell growth, proliferation, survival, angiogenesis and metabolism, whereas p110β mediates GPCR signaling from mitogens and chemokines and therefore may regulate tumor cell proliferation, metabolism, inflammation and invasion (Vogt et al., 2009; Jia et al., 2009).

The mutation of the gene encoding p110β is rare in tumors, but amplification of PI3Kβ has been found in many tumors (Bénistant et al., 2000; Brugge et al., 2007). Importantly, in a mouse prostate tumor model driven by PTEN deficiency, ablation of p110α was shown to have no effect on tumorigenesis (Jia et al., 2008). Furthermore, in PTEN-deficient human cancer cell lines (e.g., PC-3, U87MG, and BT549) of p110β, but not p110α, inhibits downstream activation of AKT, cell transformation, and the growth of PTEN-deficient cells and tumor xenografts (Wee et al., 2008). Genetic studies have suggested that the kinase activity of p110β is essential in cellular transformation caused by PTEN loss. For example, adding back a kinase-dead p110β, but not its wild-type counterpart, impaired focus formation in PTEN-deficient PC3 cells depleted for endogenous p110β (Wee et al., 2008). These studies demonstrate that PTEN-deficient tumor cells depend on p110β and its catalytic activity for signaling and growth.

Genetic alteration of tumor suppressor gene PTEN is frequently found in many cancers (Liu et al., 2009), such as endometrial cancer (43%), CRPC (35-79%), glioma (19%) and melanoma (18%). In the case of endometrial cancer, coexisting PIK3CA and PTEN genetic alteration was confirmed (Yuan & Cantley, 2008). In addition to mutation, amplification of PIK3CA and loss-of-function of PTEN by various molecular mechanisms have been discovered. For example, amplification of PIK3CA and loss-of-function of PTEN was found in 30-50% and 35-60% of gastric cancer patients, respectively, although PIK3CA and PTEN mutation rate was reported to be less than 7% of each (Byun et al., 2003; Oki et al., 2006; Li et al., 2005; Sanger Database).

While a subset of tumor types are solely dependent on PI3Kα signaling, other tumors are dependent on PI3K signaling or on a combination of both PI3Kα and PI3Kβ signaling.

Therefore, there remains a need for balanced PI3K α/β inhibitors capable of inhibiting both PI3K alpha and beta targets.

WO 2008/070150 (Bayer Schering Pharma Aktiengesellschaft) relates to 2,3-dihydroimidazo[1,2-c]quinazoline compounds, to pharmaceutical compositions containing such compounds and the use of such compounds or compositions for phosphotidylinositol-3-kinase (PI3K) inhibition, and treating diseases associated with PI3K activity, in particular treating hyper-proliferative and/or angiogenesis disorders, as a sole agent or in combination with other active ingredients. Said compounds show an increased activity (lower IC$_{50}$) against PI3K alpha than against PI3k beta.

However, the state of the art described above does not describe the compounds of general formula (I) of the present invention, a stereoisomer, a tautomer, an N-oxide, a hydrate, a solvate, or a salt thereof, or a mixture of same, as described and defined in the claims herein, and as hereinafter referred to as "compounds of the present invention". Nor does the state of the art described above show the pharmacological activity as shown by the compounds of general formula (I) of the present invention.

It has now been found, and this constitutes the basis of the present invention, that said compounds of the present invention, as described and defined herein, and as hereinafter referred to as "compounds of the present invention", have surprising and advantageous properties: the compounds of the present invention display surprising balanced activity for the inhibition of phosphatidylinositol-3-kinase alpha- and beta-isoforms as shown in the biological section of this text, which is shown as the ratio PI3K beta IC$_{50}$/PI3K alpha IC$_{50}$.

The compounds of the present invention, including salts, metabolites, solvates, solvates of salts, hydrates, and stereoisomeric forms thereof, exhibit anti-proliferative activity and are thus useful to prevent or treat the disorders associated with hyper-proliferation: in particular, said compounds of general formula (I) of the present invention may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by the PI3K pathway, such as, for example, haemotological tumours, solid tumours, and/or metastases thereof, e.g. Leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

DESCRIPTION OF THE INVENTION

One embodiment of this invention encompasses a compound having the general formula (I):

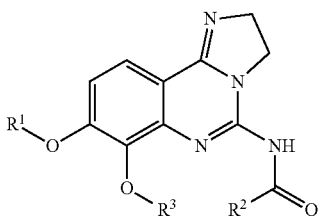
(I)

in which:
R¹ represents —(CH₂)ₙ—(CHR⁴)—(CH₂)ₘ—N(R⁵)(R⁵')
R² represents a heteroaryl of structure:

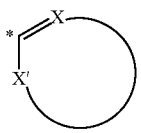

optionally substituted with 1, 2 or 3 R⁶ groups,
in which:
* represents the point of attachment of said heteroaryl with the rest of the compound of general formula (I),
X represents N or C—R⁶,
X' represents O, S, NH, N—R⁶, N or C—R⁶,
with the proviso that when X and X' are both C—R⁶, then one C—R⁶ is C—H;
R³ is methyl;
R⁴ is hydroxy;
R⁵ and R⁵' are the same or different and are, independently of each other, a hydrogen atom, or a C₁-C₆-alkyl, C₃-C₆-cycloalkyl-C₁-C₆-alkyl, or C₁-C₆-alkoxy-C₁-C₆-alkyl,
or
R⁵ and R⁵', taken together with the nitrogen atom to which they are bound, represent a 3- to 7-membered nitrogen containing heterocyclic ring optionally containing at least one additional heteroatom selected from oxygen, nitrogen or sulfur and which may be optionally substituted with 1 or more R⁶' groups;
each occurrence of R⁶ may be the same or different and is independently a hydrogen atom, a halogen atom, C₁-C₆-alkyl, C₂-C₆-alkenyl, C₂-C₆-alkynyl, C₃-C₆-cycloalkyl, C₃-C₆-cycloalkyl-C₁-C₆-alkyl, aryl, aryl-C₁-C₆-alkyl, heteroaryl, heteroaryl-C₁-C₆-alkyl, 3- to 8-membered heterocyclic ring, 3- to 8-membered heterocyclyl-C₁-C₆-alkyl, —C₁-C₆-alkyl-OR⁷, —C₁-C₆-alkyl-SR⁷, —C₁-C₆-alkyl-N(R⁷)(R⁷'), —C₁-C₆-alkyl-C(=O)R⁷, —CN, —C(=O)OR⁷, —C(=O)N(R⁷)(R⁷'), —OR⁷, —SR⁷, —N(R⁷)(R⁷'), or —NR⁷C(=O)R⁷ each of which may be optionally substituted with 1 or more R⁸ groups;
each occurrence of R⁶' may be the same or different and is independently C₁-C₆-alkyl, C₃-C₆-cycloalkyl-C₁-C₆-alkyl, or C₁-C₆-alkyl-OR⁷;
each occurrence of R⁷ and R⁷' may be the same or different and is independently a hydrogen atom, or a C₁-C₆-alkyl, C₂-C₆-alkenyl, C₂-C₆-alkynyl, C₃-C₆-cycloalkyl, C₃-C₆-cycloalkyl-C₁-C₆-alklyl, C₃-C₆-cycloalkenyl, aryl, aryl-C₁-C₆-alkyl, heteroaryl, 3- to 8-membered heterocyclic ring, 3- to 8-membered heterocyclyl-C₁-C₆-alkyl, or heteroaryl-C₁-C₆-alkyl;
each occurrence of R⁸ is independently a halogen atom, or nitro, hydroxy, cyano, formyl, acetyl, amino, C₁-C₆-alkyl, C₁-C₆-alkoxy, C₂-C₆-alkenyl, C₂-C₆-alkynyl, C₃-C₆-cycloalkyl, C₃-C₆-cycloalkyl-C₁-C₆-alkyl, C₁-C₆-cycloalkenyl, aryl, aryl-C₁-C₆-alkyl, heteroaryl, 3- to 8-membered heterocyclic ring, heterocyclyl-C₁-C₆-alkyl, or heteroaryl-C₁-C₆-alkyl;
n is an integer of 1 and m is an integer of 1;
with the proviso that when:
said R⁵ and R⁵', taken together with the nitrogen atom to which they are bound, represent:

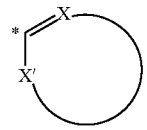

in which * represents the point of attachment with the rest of the structure of general formula (I),
then
said R² heteroaryl of structure:

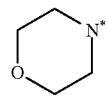

is not:

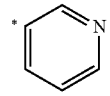

in which * represents the point of attachment with the rest of the structure of general formula (I).
or a stereoisomer, a tautomer, an N-oxide, a hydrate, a solvate, or a salt thereof, in particular a physiologically acceptable salt, or a mixture of same.

DEFINITIONS

The terms as mentioned in the present text have preferably the following meanings:
The term "halogen atom" or "halo" is to be understood as meaning a fluorine, chlorine, bromine or iodine atom.
The term "C₁-C₆-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2 or 3 carbon atoms ("C₁-C₃-alkyl"), methyl, ethyl, n-propyl- or iso-propyl.
The term "C₁-C₆-alkoxy" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "$C_1$-$C_6$-alkoxy-$C_1$-$C_6$-alkyl" is to be understood as preferably meaning a linear or branched, saturated, monovalent alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, in which the term "$C_1$-$C_6$-alkyl" is defined supra, or an isomer thereof.

The term "$C_2$-$C_6$-alkenyl" is to be understood as preferably meaning a linear or branched, monovalent hydrocarbon group, which contains one or more double bonds, and which has 2, 3, 4, 5, or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5, or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-inyl, hex-3-inyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-inyl, 1,1-dimethylbut-3-ynyl, 1,1-dimethylbut-2-ynyl, or 3,3-dimethyl-but-1-ynyl group. Particularly, said alkynyl group is ethynyl, prop-1-ynyl, or prop-2-inyl.

The term "$C_3$-$C_6$-cycloalkyl" is to be understood as preferably meaning a saturated, monovalent, mono-, or bicyclic hydrocarbon ring which contains 3, 4, 5, or 6 carbon atoms. Said $C_3$-$C_6$-cycloalkyl group is for example, a monocyclic hydrocarbon ring, e.g. a cyclopropyl, cyclobutyl, cyclopentyl, or cyclohexyl group, or a bicyclic hydrocarbon ring, e.g. a perhydropentalenylene or decalin ring. Said cycloalkyl ring can optionally contain one or more double bonds e.g. cycloalkenyl, such as a cyclopropenyl, cyclobutenyl, cyclopentenyl or cyclohexenyl group, wherein the bond between said ring with the rest of the molecule may be to any carbon atom of said ring, be it saturated or unsaturated.

The term "alkylene" is understood as preferably meaning an optionally substituted hydrocarbon chain (or "tether") having 1, 2, 3, 4, 5, or 6 carbon atoms, i.e. an optionally substituted —$CH_2$— ("methylene" or "single membered tether" or, for example —$C(Me)_2$-), —$CH_2$—$CH_2$— ("ethylene", "dimethylene", or "two-membered tether"), —$CH_2$—$CH_2$—$CH_2$— ("propylene", "trimethylene", or "three-membered tether"), —$CH_2$—$CH_2$—$CH_2$—$CH_2$— ("butylene", "tetramethylene", or "four-membered tether"), —$CH_2$—$CH_2$—$CH_2$—$CH_2$—$CH_2$— ("pentylene", "pentamethylene" or "five-membered ether"), or —$CH_2$—$CH_2$—$CH_2$—$CH_2$—$CH_2$—$CH_2$— ("hexylene", "hexamethylene", or "six-membered tether") group. Particularly, said alkylene tether has 1, 2, 3, 4, or 5 carbon atoms, more particularly 1 or 2 carbon atoms.

The term "3- to 8-membered heterocycloalkyl", is to be understood as meaning a saturated, monovalent, mono- or bicyclic hydrocarbon ring which contains 2, 3, 4, 5, 6 or 7 carbon atoms, and one or more heteroatom-containing groups selected from C(=O), O, S, S(=O), S(=O)$_2$, NR$^a$, in which R$^a$ represents a hydrogen atom, or a $C_1$-$C_6$-alkyl- or halo-$C_1$-$C_6$-alkyl-group; it being possible for said heterocycloalkyl group to be attached to the rest of the molecule via any one of the carbon atoms or, if present, the nitrogen atom.

Particularly, said 3- to 8-membered heterocycloalkyl can contain 2, 3, 4, 5, 6 or 7 carbon atoms, and one or more of the above-mentioned heteroatom-containing groups (a "3- to 8-membered heterocycloalkyl"), more particularly said heterocycloalkyl can contain 4 or 5 carbon atoms, and one or more of the above-mentioned heteroatom-containing groups (a "5- to 7-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused.

Said heterocyclyl can be bicyclic, such as, without being limited thereto, a 5,5-membered ring, e.g. a hexahydrocyclopenta[c]pyrrol-2(1H)-yl) ring, or a 5,6-membered bicyclic ring, e.g. a hexahydropyrrolo[1,2-a]pyrazin-2(1H)-yl ring, or 8-oxa-3-azabicyclo[3.2.1]oct-3-yl ring, for example.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group. A particular example of an aryl group is one of the following possible structures:

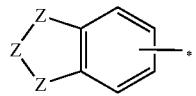

in which z represents O, S, NH or N($C_1$-$C_6$-alkyl), and * indicates the point of attachment of said aryl group with the rest of the molecule.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed.

Particularly, said heteroaryl is of structure:

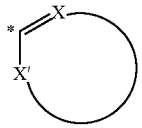

optionally substituted with 1, 2 or 3 $R^6$ groups, in which:
* represents the point of attachment of said heteroaryl with the rest of the compound of general formula (I) as defined supra,
X represents N or C—$R^6$,
X' represents O, S, NH, N—$R^6$, N or C—$R^6$,
  each occurrence of $R^6$ may be the same or different and is independently a hydrogen atom, a halogen atom, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, aryl, aryl-$C_1$-$C_6$-alkyl, heteroaryl, heteroaryl-$C_1$-$C_6$-alkyl, 3- to 8-membered heterocyclic ring, 3- to 8-membered heterocyclyl-$C_1$-$C_6$-alkyl, —$C_1$-$C_6$-alkyl-$OR^7$, —$C_1$-$C_6$-alkyl-$SR^7$, —$C_1$-$C_6$-alkyl-N($R^7$)($R^{7'}$), —$C_1$-$C_6$-alkyl-C(=O)$R^7$, —CN, —C(=O)$OR^7$, —C(=O)N($R^7$)($R^{7'}$), —$OR^7$, —$SR^7$, —N($R^7$)($R^{7'}$), or —$NR^7$C(=O)$R^7$ each of which may be optionally substituted with 1 or more $R^8$ groups;
each occurrence of $R^7$ and $R^{7'}$ may be the same or different and is independently a hydrogen atom, or a $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alklyl, $C_3$-$C_6$-cycloalkenyl, aryl, aryl-$C_1$-$C_6$-alkyl, heteroaryl, 3- to 8-membered heterocyclic ring, 3- to 8-membered heterocyclyl-$C_1$-$C_6$-alkyl, or heteroaryl-$C_1$-$C_6$-alkyl;
each occurrence of $R^8$ is independently a halogen atom, or nitro, hydroxy, cyano, formyl, acetyl, amino, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-cycloalkenyl, aryl, aryl-$C_1$-$C_6$-alkyl, heteroaryl, 3- to 8-membered heterocyclic ring, heterocyclyl-$C_1$-$C_6$-alkyl, or heteroaryl-$C_1$-$C_6$-alkyl.

More particularly, said heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl" or "$C_1$-$C_6$-alkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

Tautomers, sometimes referred to as proton-shift tautomers, are two or more compounds that are related by the migration of a hydrogen atom accompanied by the switch of one or more single bonds and one or more adjacent double bonds. The compounds of this invention may exist in one or more tautomeric forms. For example, a compound of Formula I may exist in tautomeric form Ia, tautomeric form Ib, or tautomeric form Ic, or may exist as a mixture of any of these forms. It is intended that all such tautomeric forms are included within the scope of the present invention.

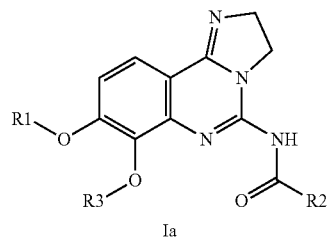
Ia

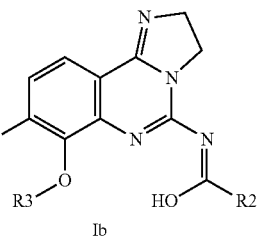
Ib

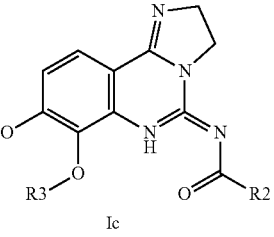
Ic

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more times", e.g. in the definition of the substituents of the compounds of the general formulae of the present invention, is understood as meaning "one, two, three, four or five times, particularly one, two, three or four times, more particularly one, two or three times, even more particularly one or two times".

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The term "carbonyl" refers to an oxygen atom bound to a carbon atom of the molecule by a double bond.

The compounds of this invention may contain one or more asymmetric centers, depending upon the location and nature of the various substituents desired. Asymmetric carbon atoms may be present in the (R)- or (S)-configuration, resulting in racemic mixtures in the case of a single asymmetric center, and diastereomeric mixtures in the case of multiple asymmetric centers. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those, which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The present invention also relates to useful forms of the compounds as disclosed herein, such as pharmaceutically acceptable salts, co-precipitates, metabolites, hydrates, solvates and prodrugs of all the compounds of examples. The term "pharmaceutically acceptable salt" refers to a relatively non-toxic, inorganic or organic acid addition salt of a compound of the present invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, sulfate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, or butyl chlorides, bromides and iodides; dialkyl sulfates like dimethyl, diethyl, dibutyl sulfate, or diamyl sulfates, long chain halides such as decyl, lauryl, myristyl and strearyl chlorides, bromides and iodides, aralkyl halides like benzyl and phenethyl bromides and others.

A solvate for the purpose of this invention is a complex of a solvent and a compound of the invention in the solid state. Exemplary solvates would include, but are not limited to, complexes of a compound of the invention with ethanol or methanol. Hydrates are a specific form of solvate wherein the solvent is water.

In a preferred embodiment, the invention encompasses the compound of Formula (I), wherein:
$R^1$ represents —$(CH_2)_n$—$(CHR^4)$—$(CH_2)_m$—$N(R^5)(R^{5'})$;
$R^2$ represents a heteroaryl of structure:

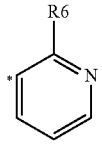

in which:
* \* represents the point of attachment of said heteroaryl with the rest of the structure of general formula (I);
* $R^3$ is methyl;
* $R^4$ is hydroxy;
* $R^5$ and $R^{5'}$ are the same or different and are, independently of each other, a hydrogen atom, or a $C_1$-$C_6$-alkyl, $C_3$-$C_6$-cycloalkyl-$C_1$-$C_6$-alkyl, or $C_1$-$C_6$-alkoxy-$C_1$-$C_6$-alkyl, or
* $R^5$ and $R^{5'}$, taken together with the nitrogen atom to which they are bound, represent a 3- to 7-membered nitrogen containing heterocyclic ring optionally containing at least one additional heteroatom selected from oxygen, nitrogen or sulfur and which may be optionally substituted with 1 or more $R^{6'}$ groups;
* each occurrence of $R^6$ may be the same or different and is independently a hydrogen atom, a halogen atom, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, aryl, aryl-$C_1$-$C_6$-alkyl, heteroaryl, heteroaryl-$C_1$-$C_6$-alkyl, 3- to 8-membered heterocyclic ring, 3- to 8-membered heterocyclyl-$C_1$-$C_6$-alkyl, —$C_1$-$C_6$-alkyl-$OR^7$, —$C_1$-$C_6$-alkyl-$SR^7$, —$C_1$-$C_6$-alkyl-$N(R^7)(R^{7'})$, —$C_1$-$C_6$-alkyl-$C(=O)R^7$, —CN, —$C(=O)OR^7$, —$C(=O)N(R^7)(R^{7'})$, —$OR^7$, —$SR^7$, —$N(R^7)(R^{7'})$, or —$NR^7C(=O)R^7$ each of which may be optionally substituted with 1 or more $R^8$ groups;
* each occurrence of $R^{6'}$ may be the same or different and is independently $C_1$-$C_6$-alkyl, $C_3$-$C_6$-cycloalkyl-$C_1$-$C_6$-alkyl, or $C_1$-$C_6$-alkyl-$OR^7$; each occurrence of $R^7$ and $R^{7'}$ may be the same or different and is independently a hydrogen atom, or a $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_3$-$C_6$-cycloalkenyl, aryl, aryl-$C_1$-$C_6$-alkyl, heteroaryl, 3- to 8-membered heterocyclic ring, 3- to 8-membered heterocyclyl-$C_1$-$C_6$-alkyl, or heteroaryl-$C_1$-$C_6$-alkyl;
* each occurrence of $R^8$ is independently a halogen atom, or nitro, hydroxy, cyano, formyl, acetyl, amino, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-cycloalkenyl, aryl, aryl-$C_1$-$C_6$-alkyl, heteroaryl, 3- to 8-membered heterocyclic ring, heterocyclyl-$C_1$-$C_6$-alkyl, or heteroaryl-$C_1$-$C_6$-alkyl;

n is an integer of 1 and m is an integer of 1;
with the proviso that when:
said $R^5$ and $R^{5'}$, taken together with the nitrogen atom to which they are bound, represent:

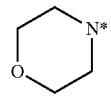

in which * represents the point of attachment with the rest of the structure of general formula (I),
then
said $R^2$ heteroaryl of structure:

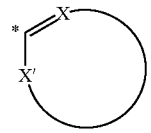

is not:

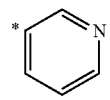

in which * represents the point of attachment with the rest of the structure of general formula (I).

or a stereoisomer, a tautomer, an N-oxide, a hydrate, a solvate, or a salt thereof, in particular a physiologically acceptable salt, or a mixture of same.

In another preferred embodiment, the invention encompasses the compound of Formula (I), wherein
$R^1$ represents —$(CH_2)_n$—$(CHR^4)$—$(CH_2)_m$—$N(R^5)(R^{5'})$;
$R^2$ represents a heteroaryl of structure:

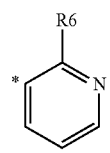

in which:
* \* represents the point of attachment of said heteroaryl with the rest of the structure of general formula (I);
* $R^3$ is methyl;
* $R^4$ is hydroxy;
* $R^5$ and $R^{5'}$ are the same or different and are, independently of each other, a hydrogen atom, or a $C_1$-$C_6$-alkyl, $C_3$-$C_6$-cycloalkyl-$C_1$-$C_6$-alkyl, or $C_1$-$C_6$-alkoxy-$C_1$-$C_6$-alkyl, or
* $R^5$ and $R^{5'}$, taken together with the nitrogen atom to which they are bound, represent a 3- to 7-membered nitrogen containing heterocyclic ring optionally containing at least one additional heteroatom selected from oxygen, nitrogen or sulfur and which may be optionally substituted with 1 or more R$^{6'}$ groups;

each occurrence of R$^6$ may be the same or different and is independently a hydrogen atom, a halogen atom, C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, aryl, aryl-C$_1$-C$_6$-alkyl, heteroaryl, heteroaryl-C$_1$-C$_6$-alkyl, 3- to 8-membered heterocyclic ring, 3- to 8-membered heterocyclyl-C$_1$-C$_6$-alkyl, —C$_1$-C$_6$-alkyl-OR$^7$, —C$_1$-C$_6$-alkyl-SR$^7$, —C$_1$-C$_6$-alkyl-N(R$^7$)(R$^{7'}$), —C$_1$-C$_6$-alkyl-C(=O)R$^7$, —CN, —C(=O)OR$^7$, —C(=O)N(R$^7$)(R$^{7'}$), —OR$^7$, —SR$^7$, —N(R$^7$)(R$^{7'}$), or —NR$^7$C(=O)R$^7$ each of which may be optionally substituted with 1 or more R$^8$ groups;

each occurrence of R$^{6'}$ may be the same or different and is independently C$_1$-C$_6$-alkyl, C$_3$-C$_6$-cycloalkyl-C$_1$-C$_6$-alkyl, or C$_1$-C$_6$-alkyl-OR$^7$;

each occurrence of R$^7$ and R$^{7'}$ may be the same or different and is independently a hydrogen atom, or a C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alklyl, C$_3$-C$_6$-cycloalkenyl, aryl, aryl-C$_1$-C$_6$-alkyl, heteroaryl, 3- to 8-membered heterocyclic ring, 3- to 8-membered heterocyclyl-C$_1$-C$_6$-alkyl, or heteroaryl-C$_1$-C$_6$-alkyl;

each occurrence of R$^8$ is independently a halogen atom, or nitro, hydroxy, cyano, formyl, acetyl, amino, C$_1$-C$_6$-alkyl, C$_1$-C$_6$-alkoxy, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, C$_1$-C$_6$-cycloalkenyl, aryl, aryl-C$_1$-C$_6$-alkyl, heteroaryl, 3- to 8-membered heterocyclic ring, heterocyclyl-C$_1$-C$_6$-alkyl, or heteroaryl-C$_1$-C$_6$-alkyl;

n is an integer of 1 and m is an integer of 1;

with the proviso that when:

said R$^5$ and R$^{5'}$, taken together with the nitrogen atom to which they are bound, represent:

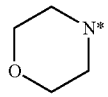

in which * represents the point of attachment with the rest of the structure of general formula (I), then said R$^2$ heteroaryl of structure:

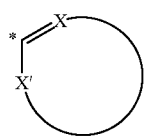

is not:

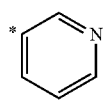

in which * represents the point of attachment with the rest of the structure of general formula (I).

or a stereoisomer, a tautomer, an N-oxide, a hydrate, a solvate, or a salt thereof, in particular a physiologically acceptable salt, or a mixture of same.

In still another preferred embodiment, the invention encompasses the compound of Formula (I), wherein:

R$^1$ represents —(CH$_2$)$_n$—(CHR$^4$)—(CH$_2$)$_m$—N(R$^5$)(R$^{5'}$)

R$^2$ represents a heteroaryl of structure:

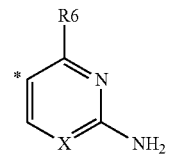

in which:

* represents the point of attachment of said heteroaryl with the rest of the structure of general formula (I), and Z represents N or C—R$^6$;

R$^3$ is methyl;

R$^4$ is hydroxy;

R$^5$ and R$^{5'}$ are the same or different and are, independently of each other, a hydrogen atom, or a C$_1$-C$_6$-alkyl, C$_3$-C$_6$-cycloalkyl-C$_1$-C$_6$-alkyl, or C$_1$-C$_6$-alkoxy-C$_1$-C$_6$-alkyl, or R$^5$ and R$^{5'}$, taken together with the nitrogen atom to which they are bound, represent a 3- to 7-membered nitrogen containing heterocyclic ring optionally containing at least one additional heteroatom selected from oxygen, nitrogen or sulfur and which may be optionally substituted with 1 or more R$^{6'}$ groups;

each occurrence of R$^6$ may be the same or different and is independently a hydrogen atom, a halogen atom, C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, aryl, aryl-C$_1$-C$_6$-alkyl, heteroaryl, heteroaryl-C$_1$-C$_6$-alkyl, 3- to 8-membered heterocyclic ring, 3- to 8-membered heterocyclyl-C$_1$-C$_6$-alkyl, —C$_1$-C$_6$-alkyl-OR$^7$, —C$_1$-C$_6$-alkyl-SR$^7$, —C$_1$-C$_6$-alkyl-N(R$^7$)(R$^{7'}$), —C$_1$-C$_6$-alkyl-C(=O)R$^7$, —CN, —C(=O)OR$^7$, —C(=O)N(R$^7$)(R$^{7'}$), —OR$^7$, —SR$^7$, —N(R$^7$)(R$^{7'}$), or —NR$^7$C(=O)R$^7$ each of which may be optionally substituted with 1 or more R$^8$ groups;

each occurrence of R$^{6'}$ may be the same or different and is independently C$_1$-C$_6$-alkyl, C$_3$-C$_6$-cycloalkyl-C$_1$-C$_6$-alkyl, or C$_1$-C$_6$-alkyl-OR$^7$;

each occurrence of R$^7$ and R$^{7'}$ may be the same or different and is independently a hydrogen atom, or a C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alklyl, C$_3$-C$_6$-cycloalkenyl, aryl, aryl-C$_1$-C$_6$-alkyl, heteroaryl, 3- to 8-membered heterocyclic ring, 3- to 8-membered heterocyclyl-C$_1$-C$_6$-alkyl, or heteroaryl-C$_1$-C$_6$-alkyl;

each occurrence of R$^8$ is independently a halogen atom, or nitro, hydroxy, cyano, formyl, acetyl, amino, C$_1$-C$_6$-alkyl, C$_1$-C$_6$-alkoxy, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, C$_1$-C$_6$-cycloalkenyl, aryl, aryl-C$_1$-C$_6$-alkyl, heteroaryl, 3- to 8-membered heterocyclic ring, heterocyclyl-C$_1$-C$_6$-alkyl, or heteroaryl-C$_1$-C$_6$-alkyl;

n is an integer of 1 and m is an integer of 1;

or a stereoisomer, a tautomer, an N-oxide, a hydrate, a solvate, or a salt thereof, in particular a physiologically acceptable salt, or a mixture of same.

In yet another preferred embodiment, the invention encompasses the compound of Formula (I), wherein:
$R^1$ represents —(CH$_2$)$_n$—(CHR$^4$)—(CH$_2$)$_m$—N(R$^5$)(R$^{5'}$)
$R^2$ represents a heteroaryl of structure:

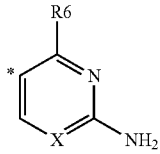

in which:
* represents the point of attachment of said heteroaryl with the rest of the structure of general formula (I), and
Z represents N or C—R$^6$;
$R^3$ is methyl;
$R^4$ is hydroxy;
$R^5$ and $R^{5'}$ are the same or different and are, independently of each other, a hydrogen atom, or a C$_1$-C$_6$-alkyl, C$_3$-C$_6$-cycloalkyl-C$_1$-C$_6$-alkyl, or C$_1$-C$_6$-alkoxy-C$_1$-C$_6$-alkyl,
or
$R^5$ and $R^{5'}$, taken together with the nitrogen atom to which they are bound, represent a 3- to 7-membered nitrogen containing heterocyclic ring optionally containing at least one additional heteroatom selected from oxygen, nitrogen or sulfur and which may be optionally substituted with 1 or more R$^{6'}$ groups;
each occurrence of R$^6$ may be the same or different and is independently a hydrogen atom, a halogen atom, C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, aryl, aryl-C$_1$-C$_6$-alkyl, heteroaryl, heteroaryl-C$_1$-C$_6$-alkyl, 3- to 8-membered heterocyclic ring, 3- to 8-membered heterocyclyl-C$_1$-C$_6$-alkyl, —C$_1$-C$_6$-alkyl-OR$^7$, —C$_1$-C$_6$-alkyl-SR$^7$, —C$_1$-C$_6$-alkyl-N(R$^7$)(R$^{7'}$), —C$_1$-C$_6$-alkyl-C(═O)R$^7$, —CN, —C(═O)OR$^7$, —C(═O)N(R$^7$)(R$^{7'}$), —OR$^7$, —SR$^7$, —N(R$^7$)(R$^{7'}$), or —NR$^7$C(═O)R$^7$ each of which may be optionally substituted with 1 or more R$^8$ groups;
each occurrence of R$^{6'}$ may be the same or different and is independently C$_1$-C$_6$-alkyl, C$_3$-C$_6$-cycloalkyl-C$_1$-C$_6$-alkyl, or C$_1$-C$_6$-alkyl-OR$^7$;
each occurrence of R$^7$ and R$^{7'}$ may be the same or different and is independently a hydrogen atom, or a C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alklyl, C$_3$-C$_6$-cycloalkenyl, aryl, aryl-C$_1$-C$_6$-alkyl, heteroaryl, 3- to 8-membered heterocyclic ring, 3- to 8-membered heterocyclyl-C$_1$-C$_6$-alkyl, or heteroaryl-C$_1$-C$_6$-alkyl;
each occurrence of R$^8$ is independently a halogen atom, or nitro, hydroxy, cyano, formyl, acetyl, amino, C$_1$-C$_6$-alkyl, C$_1$-C$_6$-alkoxy, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, C$_1$-C$_6$-cycloalkenyl, aryl, aryl-C$_1$-C$_6$-alkyl, heteroaryl, 3- to 8-membered heterocyclic ring, heterocyclyl-C$_1$-C$_6$-alkyl, or heteroaryl-C$_1$-C$_6$-alkyl;
n is an integer of 1 and m is an integer of 1;
or a stereoisomer, a tautomer, an N-oxide, a hydrate, a solvate, or a salt thereof, in particular a physiologically acceptable salt, or a mixture of same.
In a further embodiment of the above-mentioned aspects, the invention relates to compounds of formula (I), wherein $R^1$ represents —(CH$_2$)$_n$—(CHR$^4$)—(CH$_2$)$_m$—N(R$^5$)(R$^{5'}$);
In a further embodiment of the above-mentioned aspects, the invention relates to compounds of formula (I), wherein $R^2$ represents a heteroaryl of structure:

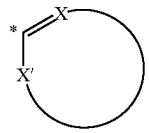

optionally substituted with 1, 2 or 3 R$^6$ groups, in which:
* represents the point of attachment of said heteroaryl with the rest of the compound of general formula (I),
X represents N or C—R$^6$,
X' represents O, S, NH, N—R$^6$, N or C—R$^6$,
with the proviso that when X and X' are both C—R$^6$, then one C—R$^6$ is C—H;
In a further embodiment of the above-mentioned aspects, the invention relates to compounds of formula (I), wherein $R^3$ is methyl;
In a further embodiment of the above-mentioned aspects, the invention relates to compounds of formula (I), wherein $R^4$ is hydroxy;
In a further embodiment of the above-mentioned aspects, the invention relates to compounds of formula (I), wherein $R^5$ and $R^{5'}$ are the same or different and are, independently of each other, a hydrogen atom, or a C$_1$-C$_6$-alkyl, C$_3$-C$_6$-cycloalkyl-C$_1$-C$_6$-alkyl, or C$_1$-C$_6$-alkoxy-C$_1$-C$_6$-alkyl,
or
$R^5$ and $R^{5'}$, taken together with the nitrogen atom to which they are bound, represent a 3- to 8-membered nitrogen containing heterocyclic ring optionally containing at least one additional heteroatom selected from oxygen, nitrogen or sulfur and which may be optionally substituted with 1 or more R$^{6'}$ groups;
In a further embodiment of the above-mentioned aspects, the invention relates to compounds of formula (I), wherein each occurrence of R$^6$ may be the same or different and is independently a hydrogen atom, a halogen atom, C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alkyl, aryl, aryl-C$_1$-C$_6$-alkyl, heteroaryl, heteroaryl-C$_1$-C$_6$-alkyl, 3- to 8-membered heterocyclic ring, 3- to 8-membered heterocyclyl-C$_1$-C$_6$-alkyl, —C$_1$-C$_6$-alkyl-OR$^7$, —C$_1$-C$_6$-alkyl-SR$^7$, —C$_1$-C$_6$-alkyl-N(R$^7$)(R$^{7'}$), —C$_1$-C$_6$-alkyl-C(═O)R$^7$, —CN, —C(═O)OR$^7$, —C(═O)N(R$^7$)(R$^{7'}$), —OR$^7$, —SR$^7$, —N(R$^7$)(R$^{7'}$), or —NR$^7$C(═O)R$^7$ each of which may be optionally substituted with 1 or more R$^8$ groups;
In a further embodiment of the above-mentioned aspects, the invention relates to compounds of formula (I), wherein each occurrence of R$^{6'}$ may be the same or different and is independently C$_1$-C$_6$-alkyl, C$_3$-C$_6$-cycloalkyl-C$_1$-C$_6$-alkyl, or C$_1$-C$_6$-alkyl-OR$^7$;
In a further embodiment of the above-mentioned aspects, the invention relates to compounds of formula (I), wherein each occurrence of R$^7$ and R$^{7'}$ may be the same or different and is independently a hydrogen atom, or a C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_6$-alklyl, C$_3$-C$_6$-cycloalkenyl, aryl, aryl-C$_1$-C$_6$-alkyl, heteroaryl, 3- to 8-membered heterocyclic ring, 3- to 8-membered heterocyclyl-C$_1$-C$_6$-alkyl, or heteroaryl-C$_1$-C$_6$-alkyl;
In a further embodiment of the above-mentioned aspects, the invention relates to compounds of formula (I), wherein each occurrence of R$^8$ is independently a halogen atom, or nitro, hydroxy, cyano, formyl, acetyl, amino, C$_1$-C$_6$-alkyl, C$_1$-C$_6$-alkoxy, C$_2$-C$_6$-alkenyl, C$_2$-C$_6$-alkynyl, C$_3$-C$_6$-cycloalkyl, $C_3$-$C_6$-cycloalkyl-$C_1$-$C_6$-alkyl, $C_1$-$C_6$-cycloalkenyl, aryl, aryl-$C_1$-$C_6$-alkyl, heteroaryl, 3- to 8-membered heterocyclic ring, heterocyclyl-$C_1$-$C_6$-alkyl, or heteroaryl-$C_1$-$C_6$-alkyl;

In a further embodiment of the above-mentioned aspects, the invention relates to compounds of formula (I), wherein n is an integer of 1 and m is an integer of 1;
with the proviso that when:
said $R^5$ and $R^{5'}$, taken together with the nitrogen atom to which they are bound, represent:

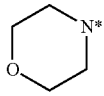

in which * represents the point of attachment with the rest of the structure of general formula (I),
then
said $R^2$ heteroaryl of structure:

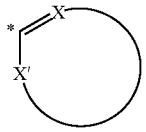

is not:

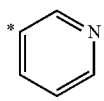

in which * represents the point of attachment with the rest of the structure of general formula (I).
$R^2$ represents a heteroaryl of structure:

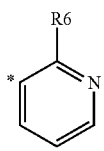

in which:
* represents the point of attachment of said heteroaryl with the rest of the structure of general formula (I);

In a further embodiment of the above-mentioned aspects, the invention relates to compounds of formula (I), wherein $R^2$ represents a heteroaryl of structure:

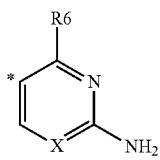

in which:
* represents the point of attachment of said heteroaryl with the rest of is the structure of general formula (I), and
Z represents N or C—$R^6$;

In an embodiment of the above-mentioned aspects, the invention relates to compounds of formula (I), according to any of the above-mentioned embodiments, in the form of or a stereoisomer, a tautomer, an N-oxide, a hydrate, a solvate, or a salt thereof, or a mixture of same.

It is to be understood that the present invention relates to any sub-combination within any embodiment of the present invention of compounds of general formula (I), supra.

More particularly still, the present invention covers compounds of general formula (I) which are disclosed in the Example section of this text, infra.

In accordance with another aspect, the present invention covers a method of preparing compounds of the present invention, the method comprising the steps as described herein.

In accordance with a further aspect, the present invention covers intermediate compounds which are useful in the preparation of compounds of the present invention of general formula (I), particularly in the method described herein. In particular, the present invention covers compounds of general formula (XI):

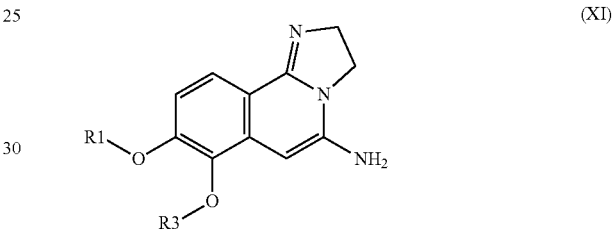

in which R1 and R3 are as defined supra as for general formula (I).

In accordance with yet another aspect, the present invention covers the use of the intermediate compounds of general formula (XI), supra, for the preparation of the compounds of the present invention of general formula (I), supra.

Where there is a discrepancy between the chemical name and the chemical structure depicted, the chemical structure depicted takes precedence over the chemical name given.

EXPERIMENTAL

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Synthetic transformations that may be employed in the synthesis of compounds of this invention and in the synthesis of intermediates involved in the synthesis of compounds of this invention are known by or accessible to one skilled in the art. Collections of synthetic transformations may be found in compilations, such as:

J. March. *Advanced Organic Chemistry*, 4th ed.; John Wiley: New York (1992) R. C. Larock. *Comprehensive Organic Transformations*, 2nd ed.; Wiley-VCH: New York (1999)

F. A. Carey; R. J. Sundberg. *Advanced Organic Chemistry*, 2nd ed.; Plenum Press: New York (1984)

T. W. Greene; P. G. M. Wuts. *Protective Groups in Organic Synthesis*, 3rd ed.; John Wiley: New York (1999)

L. S. Hegedus. *Transition Metals in the Synthesis of Complex Organic Molecules*, 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocyclic Chemistry II*; Pergamon Press: Oxford, UK (1996)

C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie* (Beilstein), which may be searched using SpotFire, and REACCS.

In the following, "PG" refers to a suitable protecting group, well-known to the person skilled in the art, e.g. from T. W. Greene; P. G. M. Wuts. *Protective Groups in Organic Synthesis*, 3rd ed.; John Wiley: New York (1999).

Reaction Scheme 1

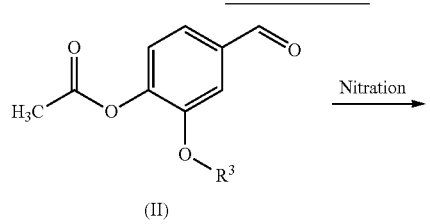

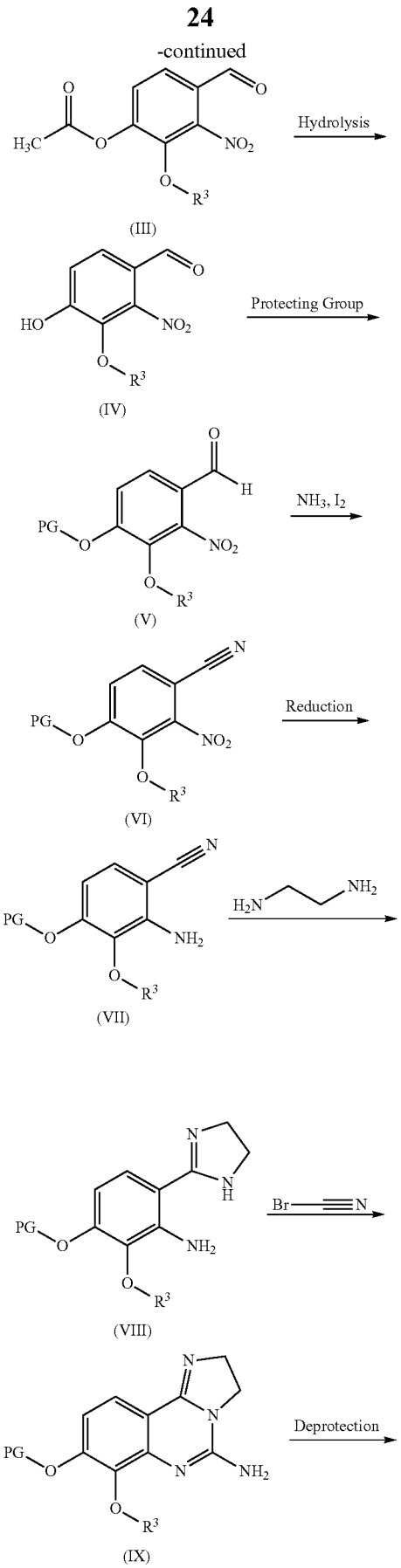

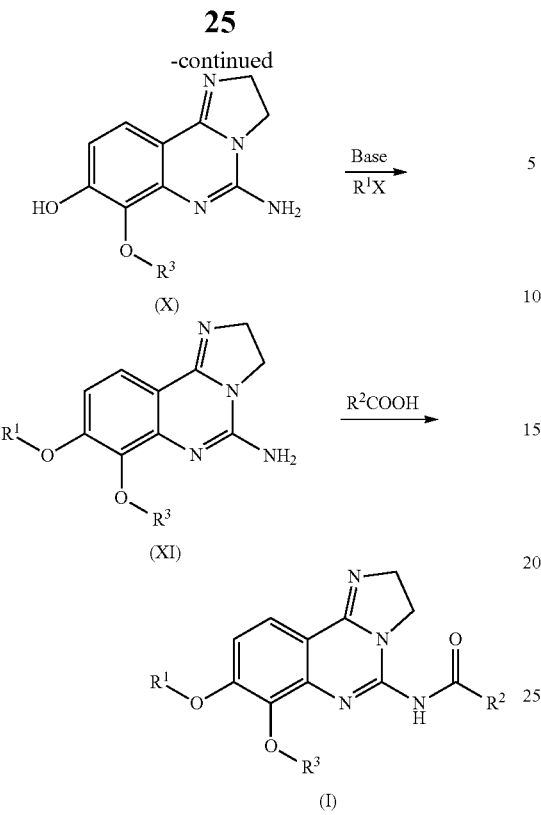

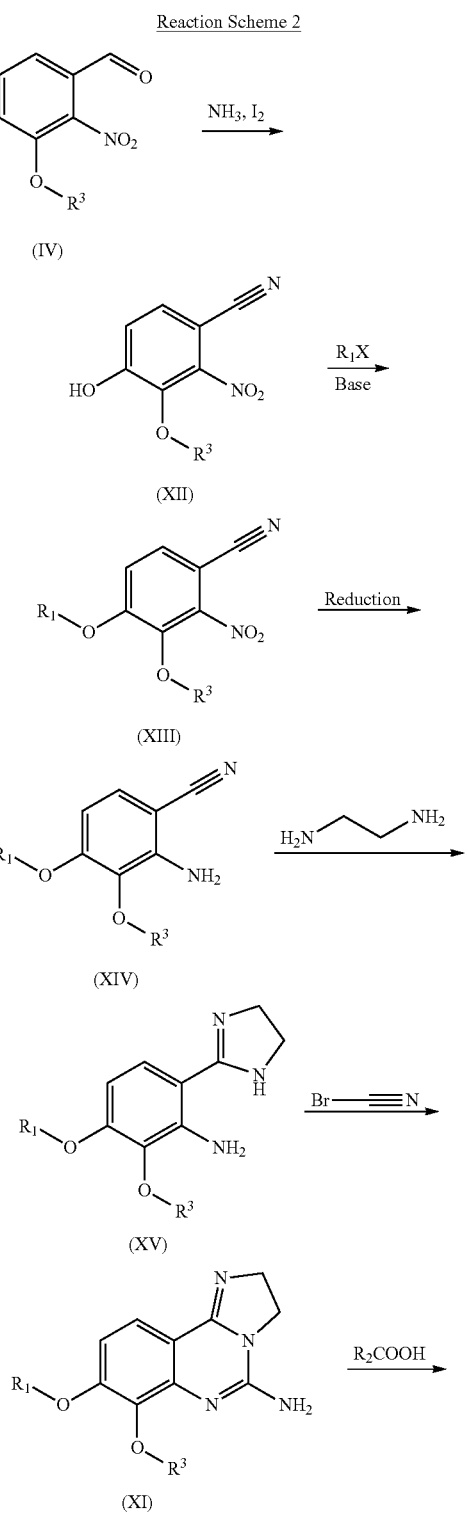

group, to provide compounds of formula (XI). Lastly, amides of formula (I) can be formed using activated esters such as acid chlorides and anhydrides or alternatively formed using carboxylic acids and appropriate coupling agents such as PYBOP, DCC, or EDCI in polar aprotic solvents.

In Reaction Scheme 1, vanillin acetate can be converted to intermediate (III) via nitration conditions such as neat fuming nitric acid or nitric acid in the presence of another strong acid such as sulfuric acid. Hydrolysis of the acetate in intermediate (III) would be expected in the presence of bases such as sodium hydroxide, lithium hydroxide, or potassium hydroxide in a protic solvent such as methanol. Protection of intermediate (IV) to generate compounds of Formula (V) (PG=protecting group, well-known to the person skilled in the art) could be accomplished by standard methods (Greene, T. W.; Wuts, P. G. M.; *Protective Groups in Organic Synthesis*; Wiley & Sons: New York, 1999). Conversion of compounds of formula (V) to those of formula (VI) can be achieved using ammonia in the presence of iodine in an aprotic solvent such as THF or dioxane. Reduction of the nitro group in formula (VI) could be accomplished using iron in acetic acid or hydrogen gas in the presence of a suitable palladium, platinum or nickel catalyst. Conversion of compounds of formula (VII) to the imidazoline of formula (VIII) is best accomplished using ethylenediamine in the presence of a catalyst such as elemental sulfur with heating. The cyclization of compounds of formula (VIII) to those of formula (IX) is accomplished using cyanogen bromide in the presence of an amine base such as triethylamine, diisopropylethylamine, or pyridine in a halogenated solvent such as DCM or dichloroethane. Removal of the protecting group in formula (IX) will be dependent on the group selected and can be accomplished by standard methods (Greene, T. W.; Wuts, P. G. M.; *Protective Groups in Organic Synthesis*; Wiley & Sons: New York, 1999). Alkylation of the phenol in formula (X) can be achieved using a base such as caesium carbonate, sodium hydride, or potassium t-butoxide in a polar aprotic solvent such as DMF or DMSO with introduction of a side chain bearing an appropriate leaving group such as a halide, or a sulfonate

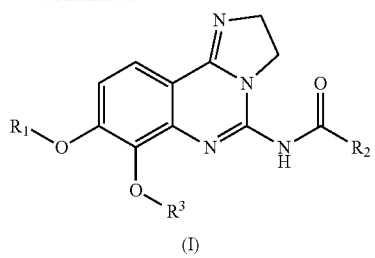

(I)

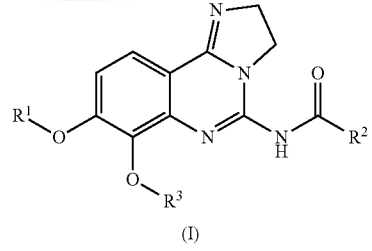

(I)

In Reaction Scheme 2, a compound of formula (IV), prepared as described above, can be converted to a structure of formula (XII) using ammonia in the presence of iodine in an aprotic solvent such as THF or dioxane. Alkylation of the phenol in formula (XII) can be achieved using a base such as caesium carbonate, sodium hydride, or potassium t-butoxide in a polar aprotic solvent such as DMF or DMSO with introduction of a side chain bearing an appropriate leaving group such as a halide, or a sulfonate group. Reduction of the nitro group in formula (XIII) could be accomplished using iron in acetic acid or hydrogen gas in the presence of a suitable palladium, platinum or nickel catalyst. Conversion of compounds of formula (XIV) to the imidazoline of formula (XV) is best accomplished using ethylenediamine in the presence of a catalyst such as elemental sulfur with heating. The cyclization of compounds of formula (XV) to those of formula (XVI) is accomplished using cyanogen bromide in the presence of an amine base such as triethylamine, diisopropylethylamine, or pyridine in a halogenated solvent such as DCM or dichloroethane. Lastly, amides of formula (I) can be formed using activated esters such as acid chlorides and anhydrides or alternatively formed using carboxylic acids and appropriate coupling agents such as PYBOP, DCC, or EDCI in polar aprotic solvents.

In Reaction Scheme 3, a compound of formula (X), prepared as described above, can be converted to amide (XVI) using activated esters such as acid chlorides and anhydrides or alternatively formed using carboxylic acids and appropriate coupling agents such as PYBOP, DCC, or EDCI in polar aprotic solvents. This could then be converted to compounds of formula (I) using a base such as caesium carbonate, sodium hydride, or potassium t-butoxide in a polar aprotic solvent such as DMF or DMSO with introduction of a side chain bearing an appropriate leaving group such as a halide, or a sulfonate group.

Reaction Scheme 4

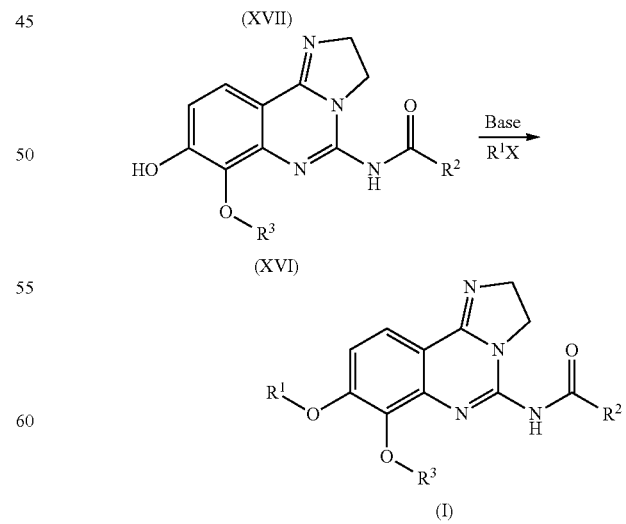

Reaction Scheme 3

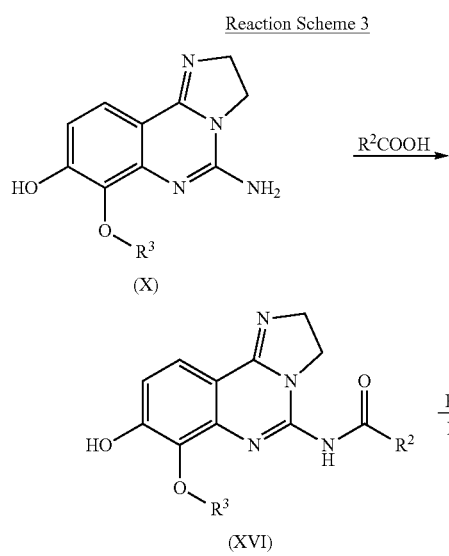

In Reaction Scheme 4, a compound of formula (IX), prepared as described above, can be converted to amide (XVII) using activated esters such as acid chlorides and anhydrides or alternatively formed using carboxylic acids and appropriate coupling agents such as PYBOP, DCC, or EDCI in polar aprotic solvents. Removal of the protecting group in formula (XVII) will be dependent on the group selected and can be accomplished by standard methods (Greene, T. W.; Wuts, P. G. M.; *Protective Groups in Organic Synthesis*; Wiley & Sons: New York, 1999). Alkylation of the phenol in formula (XVI) can be achieved using a base such as caesium carbonate, sodium hydride, or potassium t-butoxide in a polar aprotic solvent such as DMF or DMSO with introduction of a side chain bearing an appropriate leaving group such as a halide, or a sulfonate group.

Reaction Scheme 5

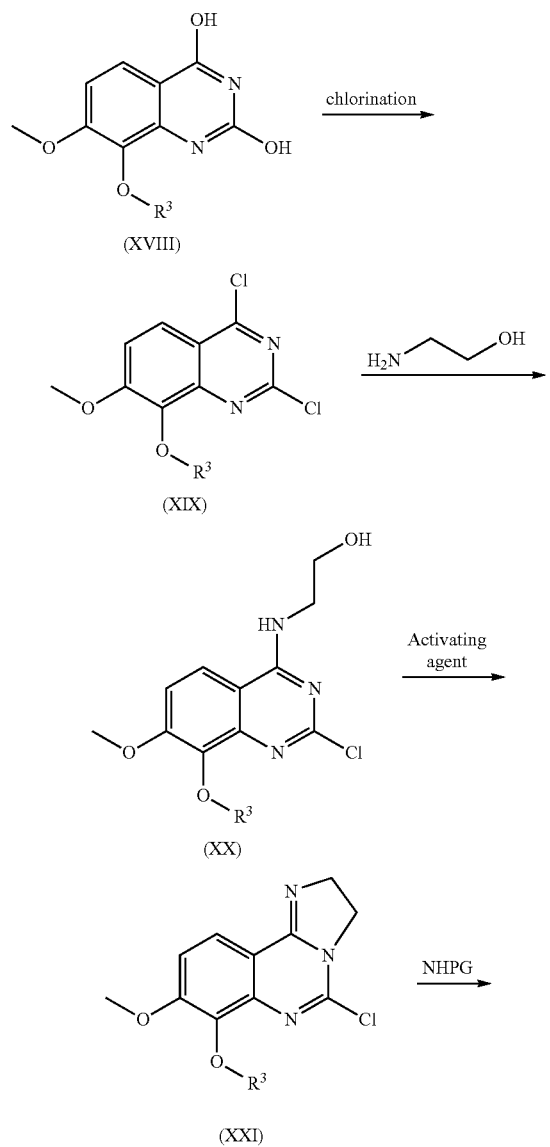

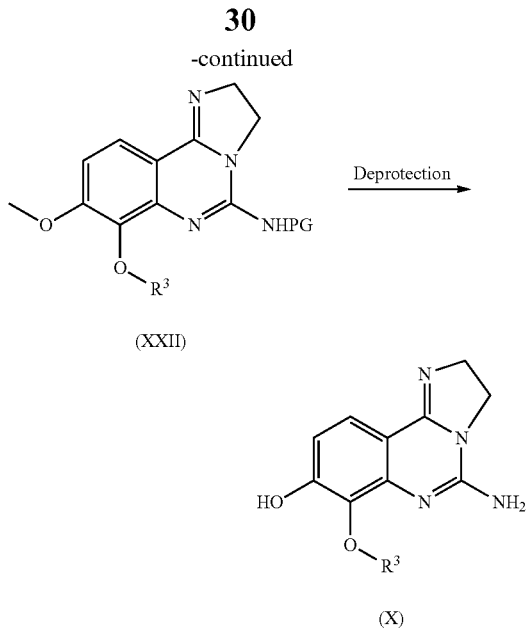

In Reaction Scheme 5, a compound of formula XVIII can be converted to the bis chloride compound of formula XIX using chlorinating agents such as $POCl_3$ or $COCl_2$ in aprotic solvents. The chloride thus obtained can be converted to imidazolines of formula XXI through reaction with appropriate quantities of ethanolamine or a suitably protected substitute, followed by activation with a suitable activating agent such as a sulfonyl chloride, $PPh_3$, or an halogenating agent such as $SOCl_2$. Chloride XXI can be converted to amine XXII through the use of any source of nucleophilic amine such as ammonia, phthalimide, or protected amines such as benzyl amine. in a polar solvent such as DMF or DMSO. Formation of the phenol depicted in formula X can be accomplished through deprotection of the methyl ether using any of the conditions outlined in the literature (Greene, T. W.; Wuts, P. G. M.; *Protective Groups in Organic Synthesis*; Wiley & Sons: New York, 1999).

In order that this invention may be better understood, the following examples are set forth. These examples are for the purpose of illustration only, and are not to be construed as limiting the scope of the invention in any manner. All publications mentioned herein are incorporated by reference in their entirety.

Abbreviations and Acronyms

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:
 acac acetylacetonate
 $Ac_2O$ acetic anhydride
 AcO (or OAc) acetate
 anh anhrous
 aq aqueous
 Ar aryl atm atmosphere
9-BBN 9-borabicyclo[3.3.1]nonyl
BINAP 2,2'-bis(diphenylphosphino)-1,1'-binaphthyl
Bn benzyl
bp boiling point
br s broad singlet
Bz benzoyl
BOC tert-butoxycarbonyl
n-BuOH n-butanol
t-BuOH tert-butanol
t-BuOK potassium tert-butoxide
C Celsius
calcd calculated
CAN ceric ammonium nitrate
Cbz carbobenzyloxy
CDI carbonyl diimidazole
$CD_3OD$ methanol-$d_4$
Celite® diatomaceous earth filter agent, Celite® Corp.
CI-MS chemical ionization mass spectroscopy
$^{13}C$ NMR carbon-13 nuclear magnetic resonance
m-CPBA meta-chloroperoxybenzoic acid
d doublet
dd doublet of doublets
DABCO 1,4-diazabicyclo[2.2.2]octane
DBU 1,8-diazabicyclo[5.4.0]undec-7-ene
DCC N,N'-dicyclohexylcarbodiimide
DCM dichloromethane
DEAD diethyl azodicarboxylate
dec decomposition
DIA diisopropylamine
DIBAL diisobutylaluminum hydride
DMAP 4-(N,N-dimethylamino)pyridine
DME 1,2-dimethoxyethane
DMF N,N-dimethylformamide
DMSO dimethylsulfoxide
E entgegen (configuration)
EDCI or 1-(3-dimethylaminopropyl)-3-ethylcarbodiimide
EDCI.HCl hydrochloride
ee enantiomeric excess
EI electron impact
ELSD evaporative light scattering detector
equiv equivalent
ES-MS electrospray mass spectroscopy
EtOAc ethyl acetate
EtOH ethanol (100%)
EtSH ethanethiol
$Et_2O$ diethyl ether
$Et_3N$ triethylamine
Fmoc 9-fluorenylmethoxycarbonyl
GC gas chromatography
GC-MS gas chromatography-mass spectroscopy
h hour, hours
hex hexanes, or hexane
$^1H$ NMR proton nuclear magnetic resonance
HMPA hexamethylphosphoramide
HMPT hexamethylphosphoric triamide
HOBT hydroxybenzotriazole
HPLC high performance liquid chromatography
insol insoluble
IPA isopropylamine
iPrOH isopropylalcohol
IR infrared
J coupling constant (NMR spectroscopy)
L liter
LAH lithium aluminum hydride
LC liquid chromatography
LC-MS liquid chromatography-mass spectrometry
LDA lithium diisopropylamide
M mol $L^{-1}$ (molar)
m multiplet
m meta
MeCN acetonitrile
MeOH methanol
MHz megahertz
min minute, minutes
μL microliter
mL milliliter
μM micromolar
mol mole
mp melting point
MS mass spectrum, mass spectrometry
Ms methanesulfonyl
m/z mass-to-charge ratio
N equiv $L^{-1}$ (normal)
NBS N-bromosuccinimide
nM nanomolar
NMM 4-methylmorpholine
NMR Nuclear Magnetic Resonance
o ortho
obsd observed
p para
p page
pp pages
$PdCl_2$dppf [1,1'-bis(diphenylphosphino)ferrocene]dichloropalladium(II)
$Pd(OAc)_2$ palladium acetate
PG protecting group, well-known to the person skilled in the art (e.g.
pH negative logarithm of hydrogen ion concentration
Ph phenyl
pK negative logarithm of equilibrium constant
$pK_a$ negative logarithm of equilibrium constant for association
PPA poly(phosphoric acid)
PS-DIEA Polystyrene-bound diisopropylethylamine
PyBOP benzotriazole-1-yl-oxy-tris-pyrrolidino-phosphonium hexafluorophosphate
q quartet
rac racemic
R rectus (configurational)
rel refers to a compound in which one chiral center is not defined, said chiral center being in the presence of one or more other chiral centers which are defined
$R_f$ retardation factor (TLC)
RT retention time (HPLC)
rt room temperature
s singlet
S sinister (configurational)
t triplet
TBDMS, TBP tert-butyldimethylsilyl
TBDPS, TPS tert-butyldiphenylsilyl
TEA triethylamine
THF tetrahydrofuran
Tf trifluoromethanesulfonyl (triflyl)
TFA trifluoroacetic acid
TFFH Fluoro-N,N,N',N'-tetramethylformamidinium hexafluorophosphate
TLC thin layer chromatography
TMAD N,N,N',N'-tetramethylethylenediamine
TMSCl trimethylsilyl chloride
Ts p-toluenesulfonyl v/v volume to volume ratio
w/v weight to volume ratio
w/w weight to weight ratio
Z zusammen (configuration)

SPECIFIC EXPERIMENTAL DESCRIPTIONS

Analytical HPLC-MS Conditions:
HPLC-MS-data given in the subsequent specific experimental descriptions refer to the following conditions:

| System: | Waters Acquity UPLC-MS: Binary Solvent Manager, Sample Manager/Organizer, Column Manager, PDA, ELSD, SQD 3001 or ZQ4000 |
|---|---|
| System: | Waters Acquity UPLC-MS: Binary Solvent Manager, Sample Manager/Organizer, PDA, ELSD, |
| Column: | Acquity UPLC BEH C18 1.7 50 × 2.1 mm |
| Solvent: | A1 = H2O + 0.1% HCOOH |
| | A2 = H2O + 0.2% NH3 |
| | B1 = Acetonitrile |
| Gradient: | 0-1.6 min 1-99% B, 1.6-2.0 min 99% B |
| Flow: | 0.8 mL/min |
| Temperature: | 60° C. |
| Injection: | 2.0 µl |
| Detection: | DAD scan range 210-400 nm |

Method 1: 99% 0.1% aqueous Formic Acid:1% $CH_3CN$ to 1% 0.1% aqueous Formic Acid:99% $CH_3CN$ over 1.6 min.; 1% 0.1% aqueous Formic Acid:99% $CH_3CN$ over 1.6 min. for 0.4 min.

Method 2: 99% 0.2% aqueous Ammonia:1% $CH_3CN$ to 1% 0.1% aqueous Ammonia:99% $CH_3CN$ over 1.6 min.; 1% 0.1% aqueous Ammonia:99% $CH_3CN$ over 1.6 min. for 0.4 min.

Unless otherwise stated, analytical HPLC utilized Method 2.

Preparative HPLC Conditions:
Unless otherwise noted, "Purification by preparative HPLC" in the subsequent specific experimental descriptions refers to the following conditions:
Analytics:

| System: | Waters Aqcuity UPLC-MS: Binary Solvent Manager, Sample Manager/Organizer, Column Manager, PDA, ELSD, SQD 3001 |
|---|---|
| Column: | Aqcuity BEH C18 1.7 50 × 2.1 mm |
| Solvent: | A = H2O + 0.1% HCOOH |
| | B = Acetonitrile |
| Gradient: | 0-1.6 min 1-99% B, 1.6-2.0 min 99% B |
| Flow: | 0.8 mL/min |
| Temperature: | 60° C. |
| Injection: | 2.0 µl |
| Detection: | DAD scan range 210-400 nm |
| | MS ESI+, ESI−, scan range 160-1000 m/z |
| | ELSD |

Preparation:

| System: | Waters Autopurificationsystem: Pump 2545, Sample Manager 2767, CFO, DAD 2996, ELSD 2424, SQD 3001 |
|---|---|
| Column: | XBrigde C18 5 µm 100 × 30 mm |
| Solvent: | A = H2O + 0.1% HCOOH |
| | B = Acetonitril |
| Gradient: | 0-1 min 1% B, 1-8 min 1-99% B, 8-10 min 99% B |
| Flow: | 50 mL/min |
| Temperature: | RT |
| Solution: | Max. 250 mg/2.5 mL DMSO o. DMF |
| Injection: | 1 × 2.5 mL |

| Detection: | DAD scan range 210-400 nm |
|---|---|
| | MS ESI+, ESI−, scan range 160-1000 m/z |

Chiral HPLC Conditions:
Chiral HPLC-data given in the subsequent specific experimental descriptions refer to the following conditions:
Analytics:

| System: | Dionex: Pump 680, ASI 100, Waters: UV-Detektor 2487 |
|---|---|
| Column: | Chiralpak IC 5 µm 150 × 4.6 mm |
| Solvent: | Hexan/Ethanol 80:20 + 0.1% Diethylamin |
| Flow: | 1.0 mL/min |
| Temperature: | 25° C. |
| Solution: | 1.0 mg/mL EtOH/MeOH 1:1 |
| Injection: | 5.0 µl |
| Detection: | UV 280 nm |

Preparation:

| System: | Agilent: Prep 1200, 2xPrep Pump, DLA, MWD, Prep FC, ESA: Corona |
|---|---|
| Column: | Chiralpak IC 5 µm 250 × 30 mm |
| Solvent: | Hexan/Ethanol 80:20 + 0.1% Diethylamin |
| Flow: | 40 mL/min |
| Temperature: | RT |
| Solution: | 660 mg/5.6 mL EtOH |
| Injection: | 8 × 0.7 mL |
| Detection: | UV 280 nm |

Preparative MPLC:
Preparative medium pressure liquid chromatography (MPLC) was carried out by standard silica gel "flash chromatography" techniques (e.g., Still et al., 1978), or by using silica gel cartridges and devices such as the Flashmaster or Biotage Flash systems.

Unless otherwise stated, MPLC purifications were conducted using a Flash Master II chromatograph equipped with an Isolute Flash $NH_2$ reverse phase column eluting with a mixed solvent gradient (100% $CH_2Cl_2$ for 3 min., gradient to 90% $CH_2Cl_2$:10% MeOH over 12 minutes; gradient to 80% $CH_2Cl_2$:20% MeOH over 20 min.; gradient to 70% $CH_2Cl_2$:30% MeOH over 10 min.; and gradient to 50% $CH_2Cl_2$:50% MeOH over 15 min.) at the flow rate recommended for the column size (i.e., 5 g column, 10 mL/min.; 50 g column, 30 ml/min.). Eluant was monitored with a UV detector at 254 nm.

Determination of Optical Rotation Conditions:
Optical rotations were measured in DMSO, at 589 nm wavelength, 20° C., concentration 1.0000 g/100 mL, intergration time 10 s, film thickness 100.00 mm.

The structures of compounds of this invention were confirmed using one or more of the following procedures.
NMR NMR spectra were acquired for each compound and were consistent with the structures shown.

Routine one-dimensional NMR spectroscopy was performed on either 300 or 400 MHz Varian® Mercury-plus spectrometers. The samples were dissolved in deuterated solvents. Chemical shifts were recorded on the ppm scale and were referenced to the appropriate solvent signals, such as 2.49 ppm for DMSO-$d_6$, 1.93 ppm for $CD_3CN$, 3.30 ppm for $CD_3OD$, 5.32 ppm for $CD_2Cl_2$ and 7.26 ppm for CDCl3 for $^1H$ spectra.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" refers to use of a Buchi rotary evaporator at approximately 15 mm of Hg. All temperatures are reported uncorrected in degrees Celsius (° C.).

Thin layer chromatography (TLC) was performed on pre-coated glass-backed silica gel 60 A F-254 250 μm plates.

Reactions employing microwave irradiation were run with a Biotage Initator® microwave oven optionally equipped with a robotic unit. The reported reaction times employing microwave heating are intended to be understood as fixed reaction times after reaching the indicated reaction temperature.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated in vacuo" refers to use of a *Buchi* rotary evaporator at a minimum pressure of approximately 15 mm of Hg. All temperatures are reported uncorrected in degrees Celsius (° C.).

Names of compounds were generated using ACD/Name Batch version 12.01. In some cases generally accepted names of commercially available reagents were used.

Synthesis of Intermediates

Intermediate A

Preparation of 2-aminopyrimidine-5-carboxylic acid

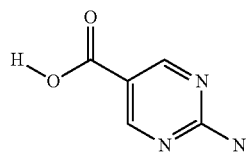

Sodium (1Z)-2-(dimethoxymethyl)-3-methoxy-3-oxoprop-1-en-1-olate was prepared as described by Zhichkin (Zhichkin et al., 2002).

Sodium (1Z)-2-(dimethoxymethyl)-3-methoxy-3-oxoprop-1-en-1-olate (1.37 g, 7.8 mmol) was diluted in DMF (12 mL), and guanidine hydrochloride (640 mg, 6.7 mmol) was added. The mixture was stirred at 100° C. for 1 h, then was cooled to rt and diluted with water. Methyl 2-aminopyrimidine-5-carboxylate precipitated as a light yellow solid, which was isolated by vacuum filtration (510 mg, 50%): $^1$H NMR (DMSO-$d_6$) δ: 8.67 (s, 2H), 7.56 (br s, 2H), 3.79 (s, 3H).

Methyl 2-aminopyrimidine-5-carboxylate (300 mg, 2.0 mmol) was diluted in methanol (5 mL) containing a few drops of water. Lithium hydroxide (122 mg, 5.1 mmol) was added, and the reaction mixture was stirred at 60° C. overnight. The mixture was concentrated under reduced pressure, then diluted in water and adjusted to pH 4 with 1 M HCl. 2-Aminopyrimidine-5-carboxylic acid precipitated as a white solid, which was isolated by vacuum filtration (244 mg, 90%): $^1$H NMR (DMSO-$d_6$) δ: 12.73 (1H, br s), 8.63 (2H, s), 7.44 (2H, br s).

Intermediate B

Preparation of 4-(3-chloropropyl)morpholine hydrochloride

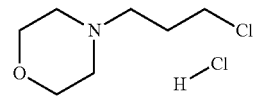

To a solution of 1-bromo-3-chloropropane (45 g, 0.29 mol) in toluene (100 mL) was added morpholine (38 g, 0.44 mol). The solution was stirred at 84° C. for 3 h, during which time a precipitate formed. After cooling to rt, the precipitate was isolated by vacuum filtration, washed with ether, and the solid was discarded. The mother liquor was acidified with HCl (4 M in dioxane, 72 mL, 0.29 mol), which caused the desired product to precipitate as an HCl salt. Solvent was removed under reduced pressure, and the resultant solid was dried to afford the title compound (53 g, 90%): $^1$H NMR (DMSO-$d_6$) δ: 11.45 (1H, br s), 3.94-3.77 (4H, m), 3.74 (2H, t), 3.39 (2H, m), 3.15 (2H, m), 3.03 (2H, m), 2.21 (2H, m).

Intermediate B

Preparation of 6-amino-2-methylnicotinic acid

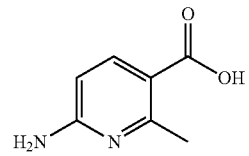

A suspension of 6-amino-2-methylnicotinonitrile (1.0 g, 7.5 mmol) in an aqueous KOH solution (20%, 12 mL) was heated at the reflux temperature for 3 days. After this time, it was cooled to room temperature, neutralized with concentrated HCl, filtered and dried to give the desired product which was used without further purification (1.1 g, 96%).

Intermediate C

Preparation of 4-[(2-oxido-1,3,2-dioxathiolan-4-yl)methyl]morpholine hydrochloride

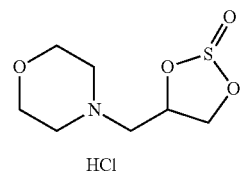 [SMILES: O=S1OCC(CN2CCOCC2)O1 ; Cl]

3-Morpholin-4-ylpropane-1,2-diol (2.1 g, 9.07 mmol) was dissolved in DCM (15 mL) and cooled to 0° C. The cooled solution was treated with thionyl chloride (1.81 mL, 24.8 mmol) and then heated at the reflux temperature for 1 h. The reaction mixture was then concentrated under reduced pressure to give a solid (2.5 g, 97%): $^1$H NMR (DMSO-d$_6$) δ: 11.4 (1H, br s), 5.64-5.55 (1H, m) 4.82 (1H, dd), 4.50 (1H, dd), 4.02-3.71 (4H, m), 3.55-3.33 (4H, m), 3.26-3.06 (2H, br s).

Intermediate D

Preparation of 8-(benzyloxy)-7-methoxy-2,3-dihydroimidazo[1,2-c]quinazolin-5-amine Step 1: Preparation of 4-formyl-2-methoxy-3-nitrophenyl acetate

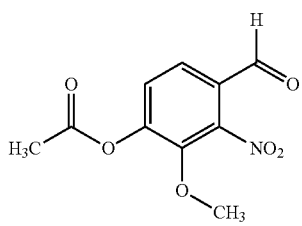 [SMILES: COc1c(OC(C)=O)ccc(C=O)c1[N+](=O)[O-]]

Fuming nitric acid (2200 mL) under nitrogen was cooled to 0° C. at which time vanillin acetate (528 g, 2.7 mol) was added portionwise, keeping the internal temperature below 10° C. After 2 h the resulting mixture was poured over ice with stirring. The slurry was filtered and the resulting solids were washed with water (3×100 mL) and air-dried. After 2 days the solids were heated in DCM (3000 mL) until complete dissolution. The solution was allowed to cool to room temperature while hexanes (3000 mL) was added dropwise. The solids were filtered, washed with hexanes (500 mL) and air dried to give 4-formyl-2-methoxy-3-nitrophenyl acetate (269 g, 41%): $^1$H NMR, (DMSO-d$_6$) δ: 9.90 (s, 1H), 7.94 (d, 1H), 7.75 (d, 1H), 3.87 (s, 3H), 2.40 (s, 3H).

Step 2: Preparation of 4-hydroxy-3-methoxy-2-nitrobenzaldehyde

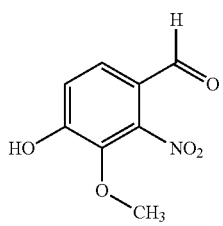

A mixture of 4-formyl-2-methoxy-3-nitrophenyl acetate 438 g (1.8 mol) and potassium carbonate (506 g, 3.7 mol) in MeOH (4000 mL) was stirred at room temperature for 16 h. The reaction mixture was concentrated under reduced pressure to afford a viscous oil. This was dissolved in water, acidified using a solution of HCl (2 N) and extracted with EtOAc. The organic layer was washed with a saturated sodium chloride solution, dried (magnesium sulfate) and filtered. The solvent was concentrated under reduced pressure to ⅓ volume and the resulting solids were filtered and air-dried to give 4-hydroxy-3-methoxy-2-nitrobenzaldehyde (317 g, 88%): $^1$H NMR (DMSO-d$_6$) δ: 9.69 (1H, s), 7.68 (1H, d), 7.19 (1H, d), 3.82 (3H, s).

Step 3: Preparation of 4-(benzyloxy)-3-methoxy-2-nitrobenzaldehyde

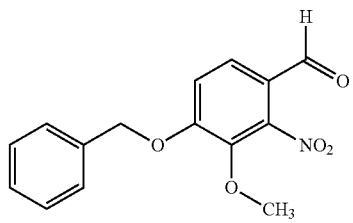 [SMILES: COc1c(OCc2ccccc2)ccc(C=O)c1[N+](=O)[O-]]

4-Hydroxy-3-methoxy-2-nitrobenzaldehyde (155 g, 786 mmol) was dissolved in DMF (1500 mL) and the stirred solution was treated with potassium carbonate (217 g, 1.57 mol) followed by benzyl bromide (161 g, 0.94 mol). After stirring for 16 h the reaction mixture was concentrated under reduced pressure and separated between water (2 L) and EtOAc (2 L). The organic layer was washed with a saturated sodium chloride solution (3×2 L), dried (an. sodium sulfate) and concentrated under reduced pressure. The resulting solids were triturated with Et$_2$O (1 L) to give 4-(benzyloxy)-3-methoxy-2-nitrobenzaldehyde (220 g, 97%): $^1$H NMR (DMSO-d$_6$) δ: 9.77 (1H, s), 7.87 (1H, d), 7.58 (1H, d), 7.51 (1H, m), 7.49 (1H, m), 7.39 (3H, m), 5.36 (2H, s), 3.05 (3H, s).

Step 4: Preparation of 4-(benzyloxy)-3-methoxy-2-nitrobenzonitrile

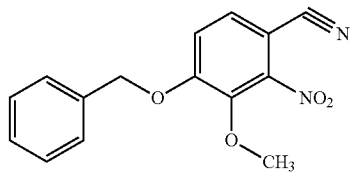

Iodine (272 g, 1.1 mmol) was added to a mixture of 4-(benzyloxy)-3-methoxy-2-nitrobenzaldehyde (220 g, 766 mmol) and ammonium hydroxide (28% solution, 3 L) dissolved in THF (5 L). After 16 h the reaction mixture was treated with sodium sulfite (49 g, 383 mmol) and concentrated under reduced pressure to afford a thick slurry. The slurry was filtered, washed with water (250 mL) and dried to afford 4-(benzyloxy)-3-methoxy-2-nitrobenzonitrile as a solid (206 g, 95%): $^1$H NMR (DMSO-d$_6$) δ: 7.89 (1H, d), 7.59 (1H, d), 7.49 (2H, m), 7.40 (3H, m), 5.35 (2H, s), 3.91 (3H, s).

Step 5: Preparation of 2-amino-4-(benzyloxy)-3-methoxybenzonitrile

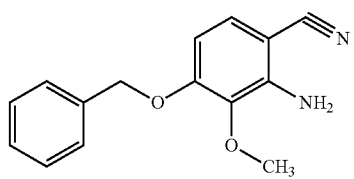 [SMILES: COc1c(OCc2ccccc2)ccc(C#N)c1[N+](=O)[O-]]

A degassed solution of 4-(benzyloxy)-3-methoxy-2-nitrobenzonitrile (185 g, 651 mmol) in glacial acetic acid (3500 mL) and water (10 mL) was cooled to 5° C. and treated with iron powder (182 g, 3.25 mol). After 3 days the reaction mixture was filtered through Celite, and the filtrate concentrated under reduced pressure. The oil, thus obtained, was treated with a saturated sodium chloride solution, neutralized with a sodium bicarbonate solution and extracted into $CH_2Cl_2$. The resulting emulsion was filtered through Celite after which the organic layer was separated, washed with a saturated sodium chloride solution, dried (an. sodium sulfate) and concentrated under reduced pressure to afford 2-amino-4-(benzyloxy)-3-methoxybenzonitrile as a solid (145 g, 88%): $^1$H NMR (DMSO-$d_6$) δ: 7.32-7.44 (5H, m), 7.15 (1H, d), 6.47 (1H, d), 5.69 (2H, s), 5.15 (2H, s), 3.68 (3H, s).

Step 6: Preparation of 3-(benzyloxy)-6-(4,5-dihydro-1H-imidazol-2-yl)-2-methoxyaniline

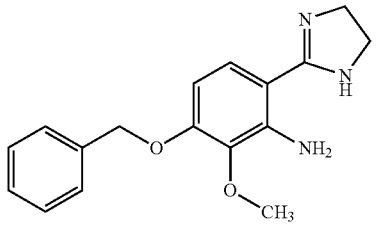 [SMILES: COc1c(OCc2ccccc2)ccc(C2=NCCN2)c1N]

A mixture of 2-amino-4-(benzyloxy)-3-methoxybenzonitrile (144 g, 566 mmol) and sulfur (55 g, 1.7 mol) in ethylenediamine (800 mL) was degassed for 30 minutes then heated to 100° C. After 16 h the reaction mixture was cooled to room temperature and then filtered. The filtrate was concentrated under reduced pressure, diluted with a saturated sodium bicarbonate solution and extracted with EtOAc. The organic layer was washed with brine, dried (sodium sulfate), filtered and concentrated under reduced pressure. The resulting solids were recrystallized from EtOAc and hexanes to afford 3-(benzyloxy)-6-(4,5-dihydro-1H-imidazol-2-yl)-2-methoxyaniline (145 g, 86%): $^1$H NMR (DMSO-$d_6$) δ: 7.27-7.48 (5H, m), 7.14 (1H, d), 6.92 (2H, m), 6.64 (1H, m), 6.32 (1H, d), 5.11 (2H, s), 3.67 (3H, s), 3.33 (2H, s).

Step 7: Preparation of 8-(benzyloxy)-7-methoxy-2,3-dihydroimidazo[1,2-c]quinazolin-5-amine

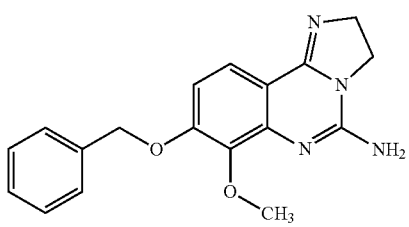 [SMILES: COc1c(OCc2ccccc2)ccc2c1N=C(N)N1CCN=C21]

A mixture of 3-(benzyloxy)-6-(4,5-dihydro-1H-imidazol-2-yl)-2-methoxyaniline (100 g, 336 mmol) and triethylamine (188 mL) in DCM (3 L) was cooled to 0° C. and treated with cyanogen bromide (78.4 g, 740 mmol). The reaction mixture was stirred and allowed to warm to room temperature gradually. After 16 h the reaction mixture was diluted with a solution of saturated sodium bicarbonate and extracted with $CH_2Cl_2$. The organic layer was washed 3 times with saturated bicarbonate solution followed by multiple washes with brine. The organic layer was dried (sodium sulfate) and concentrated under reduced pressure to give a semi solid (130 g with triethylamine salt contamination): $^1$H NMR (DMSO-$d_6$) δ: 7.30-7.48 (7H, m), 5.31 (2H, s), 4.32 (2H, m), 4.13 (2H, m), 3.81 (3H, s).

Intermediate E

Preparation of 5-amino-7-methoxy-2,3-dihydroimidazo[1,2-c]quinazolin-8-ol bis(trifluoroacetate)

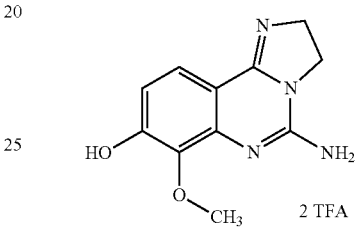

3-(Benzyloxy)-6-(4,5-dihydro-1H-imidazol-2-yl)-2-methoxyaniline (30 g, 93 mmol) was added portionwise over 1 h to a round bottom flask containing TFA (400 mL) precooled with an ice bath. The reaction mixture was heated to 60° C. and allowed to stir at this temperature for 17 h at which time it was cooled to rt and the reaction mixture concentrated under reduced pressure. The resulting residue was taken up in DCM and hexanes and concentrated under reduced pressure. The material thus obtained was dissolved in a MeOH/$CH_2Cl_2$ solution (250 mL, 1:1) and concentrated under reduced pressure. The resulting solid was dried overnight under vacuum with low heat to give 5-amino-7-methoxy-2,3-dihydroimidazo[1,2-c]quinazolin-8-ol bis(trifluoroacetate) (44.7 g, >100%): $^1$H NMR (DMSO-$d_6$) δ: 7.61 (1H, m), 6.87 (1H, m), 4.15 (2H, br t), 4.00 (2H, m), 3.64 (3H, s).

Intermediate F

Preparation of 7-Methoxy-8-[(2R)-oxiran-2-yl methoxy]-2,3-dihydroimidazo[1,2-c]quinazolin-5-amine

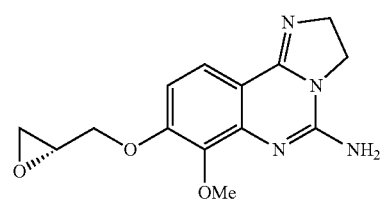 [SMILES: COc1c(OC[C@H]2CO2)ccc2c1N=C(N)N1CCN=C21]

Step 1: Preparation of (R)-Glycidyl Methanesulfonate

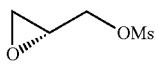

A solution of (S)-(−)-glycidol (8.6 mL, 130 mmol) and triethylamine (36.2 mL, 260 mmol, 2.0 equiv.) in DMF (250 mL) was cooled over an ice bath and methanesulfonyl chloride (10.1 mL, 130 mmol, 1.0 equiv.) was added dropwise. The mixture was stirred for 1.5 hr at room temperature affording a 0.47 M solution of (R)-glycidyl methanesulfonate in DMF, which was used without further purification.

Step 2: Preparation of 7-Methoxy-8-[(2R)-oxiran-2-ylmethoxy]-2,3-dihydroimidazo[1,2-c]quinazolin-5-amine To a solution of 5-amino-7-methoxy-2,3-dihydroimidazo[1,2-c]quinazolin-8-ol bis(trifluoroacetate) (Intermediate E, 0.30 g, 0.65 mmol) in DMF (8 mL) was added caesium carbonate to generate a white suspension. The suspension was stirred at room temperature for 1.5 hr, then (R)-glycidyl methanesulfonate (Intermediate F, Step 1, 3.9 mL of 0.34 M solution in DMF, 1.30 mmol, 2.0 equiv.) was added, and the resulting solution was stirred at 60° C. for 20 h. The resulting suspension was concentrated under reduced pressure and the residue was treated separated between a saturated sodium bicarbonate solution (30 mL) and a 4:1 CH$_2$Cl$_2$/isopropanol solution (30 mL). The aqueous phase was extracted with a 4:1 CH$_2$Cl$_2$/isopropanol solution (30 mL). The combined organic phases were dried (an. sodium sulfate) and concentrated under reduced pressure. The residue was purified using MPLC (Isolute Flash NH$_2$ reverse phase column; 100% CH$_2$Cl$_2$ for 5 min., gradient to 95% CH$_2$Cl$_2$:5% MeOH over 15 minutes; gradient to 90% CH$_2$Cl$_2$:10% MeOH over 15 min.; gradient to 80% CH$_2$Cl$_2$: 20% MeOH over 15 min.; and gradient to 75% CH$_2$Cl$_2$:25% MeOH over 15 min.) to give 7-methoxy-8-[(2R)-oxiran-2-ylmethoxy]-2,3-dihydroimidazo[1,2-c]quinazolin-5-amine (0.080 g, 43%): $^1$H NMR (DMSO-d$_6$+1 drop TFA-d) δ 2.71 (dd, J=2.5, 4.8 Hz, 1H), 2.85, (t, J=4.6 Hz, 1H), 3.34-3.40 (br m, 1H), 3.75 (s, 3H), 3.82 (s, 3H), 4.30 (dd, J=6.6, 11.4 Hz, 1H), 4.10 (br t, J=9.7 Hz, 2H), 4.31 (br t, J=9.7 Hz, 2H), 4.54 (dd, J=2.3, 11.6 Hz, 1H), 7.26 (d, J=9.4 Hz, 1H), 7.84 (d, J=9.1 Hz, 1H).

Intermediate G

Preparation of 7-Methoxy-8-(oxiran-2-ylmethoxy)-2,3-dihydroimidazo[1,2-c]quinazolin-5-amine

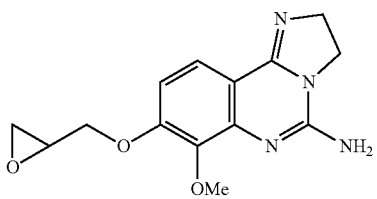 [SMILES: COc1c(OCC2CO2)ccc2c1N=C(N)N1CCN=C21]

Step 1: Preparation of Racemic Glycidyl Methanesulfonate

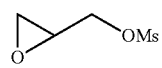

Racemic glycidol methanesulfonate was synthesized in a manner analogous to Intermediate F, Step 1, substituting racemic glycidol for (S)-(−)-glycidol The solution of racemic glycidyl methanesulfonate in DMF was used in further transformations without further purification.

Step 2: Preparation of 7-Methoxy-8-(oxiran-2-ylmethoxy)-2,3-dihydroimidazo[1,2-c]quinazolin-5-amine Intermediate G was synthesized in an analogous manner Intermediate F, Step 2 substituting racemic glycidyl methanesulfonate for (R)-glycidyl methanesulfonate (0.30 g, 24%): HPLC ret. time 0.62 min.; $^1$H NMR (DMSO-d$_6$+1 drop TFA-d) δ 2.71 (dd, J=2.5, 4.8 Hz, 1H), 2.85, (t, J=4.6 Hz, 1H), 3.34-3.40 (br m, 1H), 4.30 (dd, J=6.6, 11.4 Hz, 1H), 4.10 (br t, J=9.7 Hz, 2H), 4.31 (br t, J=9.7 Hz, 2H), 4.54 (dd, J=2.3, 11.6 Hz, 1H), 7.21 (d, J=9.4 Hz, 1H), 7.79 (d, J=9.1 Hz, 1H).

Intermediate H

Preparation of 7-methoxy-8-[(2S)-oxiran-2-ylmethoxy]-2,3-dihydroimidazo[1,2-c]quinazolin-5-amine

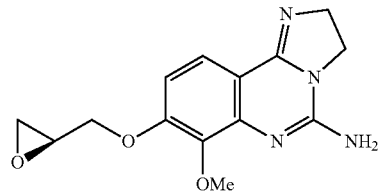 [SMILES: COc1c(OC[C@@H]2CO2)ccc2c1N=C(N)N1CCN=C21]

Step 1: Preparation of (S)-Glycidyl Methanesulfonate

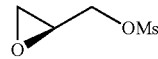

(S)-Glycidyl Methanesulfonate was synthesized in an analogous manner to Intermediate F, Step 1, substituting (R)-(+)-glycidol for (S)-(−)-glycidol. This was used in further transformations as a solution of (S)-glycidyl methanesulfonate in DMF, without further purification.

Step 2: Preparation of 7-methoxy-8-[(2S)-oxiran-2-ylmethoxy]-2,3-dihydroimidazo[1,2-c]quinazolin-5-amine Intermediate G was synthesized in an analogous manner Intermediate F, Step 2 substituting (S)-glycidyl methanesulfonate for (R)-glycidyl methanesulfonate (0.14 g, 15%): HPLC ret. time 0.62 min.; $^1$H NMR (DMSO-$d_6$+1 drop TFA-d) δ 2.71 (dd, J=2.5, 4.8 Hz, 1H), 2.85, (t, J=4.6 Hz, 1H), 3.34-3.40 (br m, 1H), 4.30 (dd, J=6.6, 11.4 Hz, 1H), 4.10 (br t, J=9.7 Hz, 2H), 4.31 (br t, J=9.7 Hz, 2H), 4.54 (dd, J=2.3, 11.6 Hz, 1H), 7.21 (d, J=9.4 Hz, 1H), 7.79 (d, J=9.1 Hz, 1H).

Intermediate I

Preparation of N-[7-methoxy-8-(oxiran-2-yl-methoxy)-2,3-dihydroimidazo[1,2-c]quinazolin-5-yl]nicotinamide

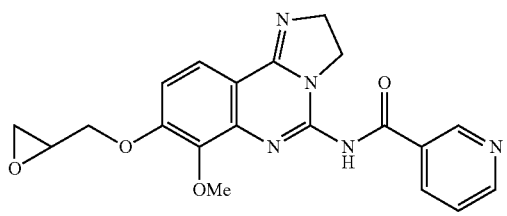 [SMILES: COc1c(OCC2CO2)ccc2c1N=C(NC(=O)c1cccnc1)N1CCN=C21]

Step 1: Preparation of N-[8-(benzyloxy)-7-methoxy-2,3-dihydroimidazo[1,2-c]quinazolin-5-yl]nicotinamide

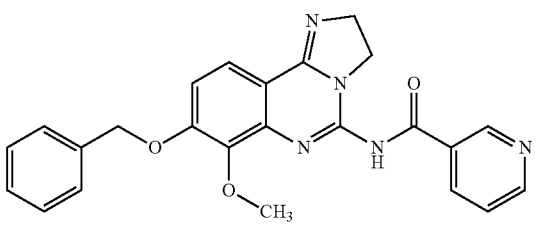 [SMILES: COc1c(OCc2ccccc2)ccc2c1N=C(NC(=O)c1cccnc1)N1CCN=C21]

To a suspension of 8-(benzyloxy)-7-methoxy-2,3-dihydroimidazo[1,2-c]quinazolin-5-amine (21 g, 65 mmol) and nicotinic acid (12 g, 97.7 mmol) in DMF (240 mL) was added diisopropylethylamine (33.7 g, 260.4 mmol) followed by PYBOP (51 g, 97.7 mmol). The resulting mixture was stirred with the aid of an overhead stirrer for 3 days at ambient temperature. The resultant precipitate was isolated by vacuum filtration, washed repeatedly with EtOAc and dried under vacuum with slight heating to yield N-[8-(benzyloxy)-7-methoxy-2,3-dihydroimidazo[1,2-c]quinazolin-5-yl]nicotinamide (27.3 g, 98%): $^1$H NMR (DMSO-$d_6$+2 drops TFA-d) δ: 9.32 (1H, s), 8.89 (1H, br m), 8.84 (1H, d), 7.89 (1H, br m), 7.82 (1H, d), 7.37 (1H, d), 7.27 (1H, d), 7.16 (6H, m), 5.18 (2H, s), 4.36 (2H, t), 4.04 (2H, t), 3.78 (3H, s); mass spectrum m/z 338 ((M+1)$^+$, 6%).

Step 2: Preparation of N-(8-hydroxy-7-methoxy-2,3-dihydroimidazo[1,2-c]quinazolin-5-yl)nicotinamide

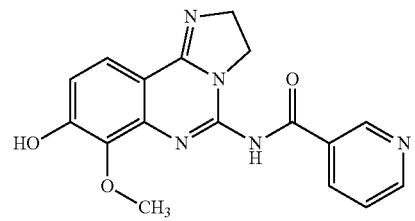 [SMILES: COc1c(O)ccc2c1N=C(NC(=O)c1cccnc1)N1CCN=C21]

N-[8-(Benzyloxy)-7-methoxy-2,3-dihydroimidazo[1,2-c]quinazolin-5-yl]nicotinamide (20 g, 45.1 mmol) was added portionwise over 1 h to a round bottom flask containing TFA (400 mL) precooled with an ice bath. The reaction mixture was heated to 60° C. and allowed to stir at this temperature for 17 h at which time it was cooled to room temperature. The reaction mixture was then concentrated under reduced pressure. The resulting residue was dissolved in CH$_2$Cl$_2$ and hexane and concentrated under reduced pressure. The material thus obtained was dissolved in MeOH and CH$_2$Cl$_2$ (250 mL, 1:1) and concentrated under reduced pressure. The resulting solids were dried overnight under vacuum with low heat to give N-(8-hydroxy-7-methoxy-2,3-dihydroimidazo[1,2-c]quinazolin-5-yl)nicotinamide (17.3 g, 66%): $^1$H NMR (DMSO-$d_6$+2 drops TFA-d) δ: 13.41 (1H, s), 12.21 (1H, brs), 9.38 (1H, s), 8.78 (1H, d), 8.53 (1H, d), 7.85 (1H, d), 7.59 (1H, m), 7.17 (1H, d), 4.54 (2H, m), 4.21 (2H, m), 3.98 (3H, s); mass spectrum m/z 481 ((M+1)$^+$).

Step 3: Preparation of N-[7-methoxy-8-(oxiran-2-yl methoxy)-2,3-dihydroimidazo[1,2-c]quinazolin-5-yl]nicotinamide A mixture of N-{8-hydroxy-7-methoxy-2,3-dihydroimidazo[1,2-c]quinazolin-5-yl}pyridine-3-carboxamide (0.85 g, 1.50 mmol) and caesium carbonate (2.93 g, 8.99 mmol, 6.0 equiv.) in DMF (12.5 mL) was stirred at room temperature for 1 h, then was treated with racemic epichlorohydrin (0.29 mL, 3.75 mmol, 2.5 equiv.), and the resulting mixture was stirred at room temperature for 16 h. The resulting mixture was used in further transformations as a 0.120 M solution of N-[7-methoxy-8-(oxiran-2-ylmethoxy)-2,3-dihydroimidazo[1,2-c]quinazolin-5-yl]nicotinamide in DMF.

Intermediate J

Preparation of N-{7-methoxy-8-[(2R)-oxiran-2-ylmethoxy]-2,3-dihydroimidazo[1,2-c]quinazolin-5-yl}nicotinamide

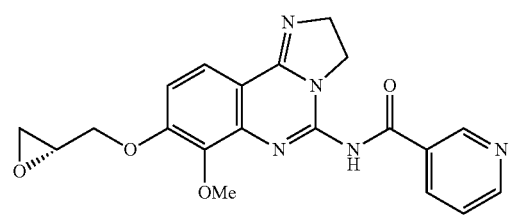 [SMILES: COc1c(OC[C@H]2CO2)ccc2c1N=C(NC(=O)c1cccnc1)N1CCN=C21]

A mixture of N-{8-hydroxy-7-methoxy-2,3-dihydroimidazo[1,2-c]quinazolin-5-yl}pyridine-3-carboxamide (Intermediate I, Step 2 (used as bis-TFA salt), 1.50 g, 2.65 mmol) and caesium carbonate (4.32 g, 13.3 mmol, 5.0 equiv.) in DMF (37 mL) was stirred at room temperature for 1 h, then was treated with (R)-glycidyl methanesulfonate (Intermediate F, Step 1, 21.2 mL, 0.25 M in DMF, 5.31 mmol, 2.0 equiv.). The resulting mixture was stirred at room temperature for 16 h at 60° C., then was cooled to room temperature and concentrated under reduced pressure. The resulting residue was separated between water (50 mL) and a 4:1 CH$_2$Cl$_2$/isopropanol solution (50 mL). The organic phase was washed with a concentrated sodium bicarbonate solution, dried (an. sodium sulfate), and concentrated under reduced pressure. The resulting material was triturated with EtOH and dried under reduced pressure to give N-{7-methoxy-8-[(2R)-oxiran-2-ylmethoxy]-2,3-dihydroimidazo[1,2-c]quinazolin-5-yl}nicotinamide (0.72 g, 69%): HPLC ret. time 0.94 min.; $^1$H NMR (DMSO-d$_6$+1 drop TFA-d) δ 2.75 (dd, J=2.5, 5.1 Hz, 1H), 2.88 (app t, J=4.7, 1H), 3-42-3.47 (m, 1H), 4.01 (s, 3H), 4.14 (dd, J=6.6, 11.6 Hz, 1H), 4.20-4.29 (m, 3H), 4.52-4.59 (m, 2H), 4.68 (dd, J=2.3, 11.6 Hz, 1H), 7.47 (d, J=9.4 Hz, 1H), 7.92 (dd, J=5.6, 7.8 Hz, 1H), 8.03 (d, J=9.1 Hz, 1H), 8.90 (br d, J=7.8 Hz, 1H), 8.97 (dd, J=1.5, 5.6 Hz, 1H), 9.49 (d, J=1.5 Hz, 1H); mass spectrum m/z 394 ((M+1)$^+$, 11%).

EXAMPLES

Comparative Example 1 (from WO 2008/070150)

Preparation of N-{8-[2-hydroxy-3-(morpholin-4-yl)propoxy]-7-methoxy-2,3-dihydroimidazo[1,2-c]quinazolin-5-yl}pyridine-3-carboxamide

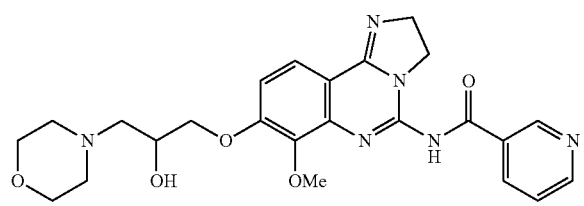

Caesium carbonate (3 g, 9.37 mmol) was added to a suspension of N-(8-hydroxy-7-methoxy-2,3-dihydroimidazo[1,2-c]quinazolin-5-yl)nicotinamide bis-trifluoroacetate (1.0 g, 1.88 mmol) in DMF (40 mL) and stirred for 1.5 h before adding 4-[(2-oxido-1,3,2-dioxathiolan-4-yl)methyl]morpholine hydrochloride (Intermediate C, 0.39 g, 1.88 mmol). After 3 h, the reaction mixture was treated with another equivalent of 4-[(2-oxido-1,3,2-dioxathiolan-4-yl)methyl]morpholine hydrochloride (Intermediate C, Step 2) and stirred at 60° C. overnight. The reaction mixture was concentrated under reduced pressure and the product was extracted with a solution of 20% isopropanol/80% chloroform and washed with a saturated solution of sodium hydrogen carbonate. The organics were dried (magnesium sulfate) and concentrated under reduced pressure, and the resulting residue was triturated with EtOAc and filtered. The solid was then purified by HPLC (Gilson, 5% MeOH/95% H$_2$O to 50% MeOH/50% H$_2$O gradient, 0.1% NH$_4$OH) to give N-{8-[2-hydroxy-3-(morpholin-4-yl)propoxy]-7-methoxy-2,3-dihydroimidazo[1,2-c]quinazolin-5-yl}pyridine-3-carboxamide (160 mg, 18%): HPLC MS RT=0.19 min.; $^1$H NMR (DMSO-d$_6$+1 drop TFA-d) δ 13.40-13.38 (1H, br s), 9.45 (1H, d), 8.90 (1H, dd), 8.72 (1H, d), 8.06 (1H, d), 7.77 (1H, dd), 7.51 (1H, d) 4.59 (2H, t), 4.49-4.41 (1H, br s), 4.33-4.22 (4H, m), 4.06 (3H, s) 4.05-3.92 (2H, m), 3.86-3.67 (2H, m), 3.51 (2H, d), 3.43-3.13 (4H, m); mass spectrum m/z 495 ((M+1)$^+$).

The following examples were prepared in a manner analogous to Comparative Example 1:

Example 21

6-amino-N-{8-[2-hydroxy-3-(morpholin-4-yl)propoxy]-7-methoxy-2,3-dihydroimidazo[1,2-c]quinazolin-5-yl}pyridine-3-carboxamide

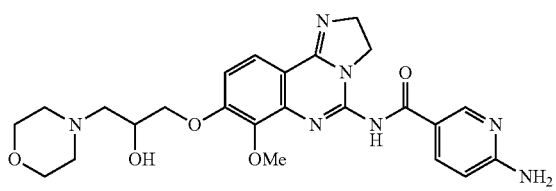 [SMILES: COc1c(OCC(O)CN2CCOCC2)ccc2c1N=C(NC(=O)c1ccc(N)nc1)N1CCN=C21]

Prepared using 6-amino-3-pyridinecarboxylic acid in place of nicotinic acid in the preparation of Intermediate I, Step 2 (94.0 mg, 31%): TLC (9:1 CH$_2$Cl$_2$/MeOH+1% NH$_4$OH in MeOH) R$_f$ 0.35; $^1$H NMR (DMSO-d$_6$+1 drop TFA-d) δ 3.14-3.44 (m, 4H), 3.48-3.56 (m, 2H), 3.68-3.87 (m, 2H), 3.94-4.03 (m, 2H), 4.05 (s, 3H), 4.22-4.32 (m, 4H), 4.42-4.50 (m, 1H), 4.50-4.59 (m, 2H), 7.07 (d, J=9.4 Hz, 1H), 7.51 (d, J=9.2 Hz, 1H), 8.06 (d, J=9.2 Hz, 1H), 8.49 (dd, J=1.9, 9.2 Hz, 1H), 8.80 (d, J=2.1 Hz, 1H); mass spectrum m/z 496 ((M+1)$^+$, 10%).

Example 2

Preparation of N-(8-{[(2R)-2-hydroxy-3-(morpholin-4-yl)propyl]oxy}-7-methoxy-2,3-dihydroimidazo[1,2-c]quinazolin-5-yl)pyridine-3-carboxamide

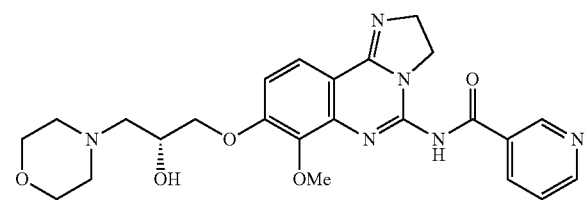 [SMILES: COc1c(OC[C@H](O)CN2CCOCC2)ccc2c1N=C(NC(=O)c1cccnc1)N1CCN=C21]

Step 1: Preparation of (2R)-3-(4-morpholinyl)-1,2-propanediol

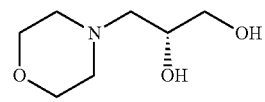

A solution of (S)-glycidol (1.00 mL, 15.0 mmol) and morpholine (1.96 mL, 22.5 mmol, 2.5 equiv.) in abs. ethanol was heated in a microwave for 4 min. at 140 0° C., cooled to room temperature and concentrated at 70° C. under a 12 mbar vacuum to afford (2R)-3-(4-morpholinyl)-1,2-propanediol (2.47 g, 102%): $^1$H NMR (CDCl$_3$) δ 2.37 (dd J=4.0, 12.4 Hz, 1H), 2.40-2.48 (m, 2H), 2.57 (dd, J=9.6, 12.4 Hz, 1H), 2.62-2.71 (m, 2H), 3.50 (dd, J=4.2, 11.4 Hz, 1H), 3.65-3.79 (m, 5H), 3.79-3.88 (m, 1H).

Step 2: Preparation of 4-[(4R)-(2-oxido-1,3,2-dioxathiolan-4-yl)methyl]morpholine hydrochloride

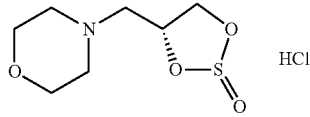

To a solution of (2R)-3-(4-morpholinyl)-1,2-propanediol (0.447 g, 2.77 mmol) in CH$_2$Cl$_2$ (7.5 mL) was cooled to 0° C. and added thionyl chloride (0.41 mL, 5.55 mmol, 2.0 equiv.) was added dropwise. The resulting solution was heated at the reflux temperature for 1 hr, cooled to room temperature and concentrated under reduced pressure to give 4-[(4R)-(2-oxido-1,3,2-dioxathiolan-4-yl)methyl]morpholine hydrochloride (0.70 g, 104%). This material was used in the next step without further purification.

Step 3: Preparation of N-(8-{[(2R)-2-hydroxy-3-(morpholin-4-yl)propyl]oxy}-7-methoxy-2,3-dihydroimidazo[1,2-c]quinazolin-5-yl)pyridine-3-carboxamide To a solution of N-(8-hydroxy-7-methoxy-2,3-dihydroimidazo[1,2-c]quinazolin-5-yl)nicotinamide bis-TFA salt (Intermediate I, Step 2, 0.750 g, 1.3 mmol) in DMF (50 mL) was added caesium carbonate (1.30 g, 3.9 mmol, 3.0 equiv.) and the resulting slurry was stirred at room temperature for 1.5 hr, followed by the addition of cyclic sulfite ester (0.275 g, 1.3 mmol, 1.0 equiv). This mixture was stirred at 60° C. for 12 hr, cooled to room temperature, treated with additional caesium carbonate (0.86 g, 2.6 mmol, 2.0 equiv.) and cyclic sulfite ester (0.275 g, 1.3 mmol, 1.0 equiv.) and stirred at 60° C. for an additional 12 hr. The resulting mixture was concentrated under reduced pressure. The residue was dissolved in a 4:1 CH$_2$Cl$_2$/isopropanol solution (100 mL), then was washed with a saturated sodium bicarbonate solution (50 mL) and a saturated sodium chloride solution (50 mL), dried (an. sodium sulfate), and concentrated under reduced pressure. The residue (1.77 g) was purified by preparative HPLC to give N-(8-{[(2R)-2-hydroxy-3-(morpholin-4-yl)propyl]oxy}-7-methoxy-2,3-dihydroimidazo[1,2-c]quinazolin-5-yl)pyridine-3-carboxamide (0.52 g, 82%): TLC (9:1 CH$_2$CO$_2$/MeOH+1% NH$_4$OH in MeOH) R$_f$ 0.35; Preparative HPLC (condition A) ret. time 3.70 min.; $^1$H NMR (DMSO-d$_6$+1 drop TFA-d) δ 3.10-3.40 (m, 4H), 3.47 (br d, J=11.9 Hz, 2H), 3.63-3.84 (m, 2H), 3.88-4.01 (m, 2H), 4.03 (s, 3H), 4.20-4.30 (m, 4H), 4.42 (br s, 1H), 4.57 (app t, J=10.3 Hz, 2H), 7.50 (d, J=9.2 Hz, 1H), 7.96 (dd, J=5.0, 7.5 Hz, 1H), 8.04 (d, J=9.2 Hz, 1H), 8.94 (br d, J=7.7 Hz, 1H), 8.99 (D, J=5.2 Hz, 1H), 9.50 (d, J=1.1 Hz, 1H); mass spectrum m/z 481 ((M+1)$^+$, 11%).

The following examples were prepared in a manner analogous to Example 2:

Example 27

2-amino-N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]pyrimidine-5-carboxamide

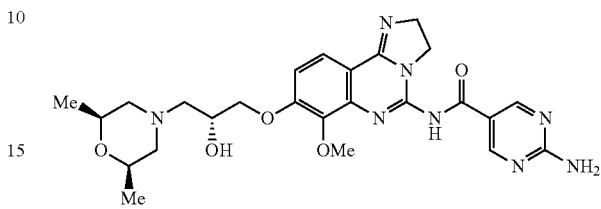

Prepared using cis-2,6-dimethylmorpholine in place of morpholine in Step 1, and using 2-amino-5-pyrimidinecarboxylic acid in place of nicotinic acid in Step 2 (61.0 mg, 31%): TLC (9:1 CH$_2$Cl$_2$/MeOH+1% NH$_4$OH in MeOH) R$_f$ 0.35; HPLC ret. time 0.81 min.; $^1$H NMR (DMSO-d$_6$+1 drop TFA-d) δ 1.08-1.14 (m, 6H), 2.72-2.83 (m, 2H), 3.23-3.30 (m, 1H), 3.43-3.55 (m, 2H), 3.77-3.89 (m, 2H), 3.89-3.97 (m, 2H), 3.99 (s, 3H), 4.15-4.26 (m, 4H), 4.39-4.54 (m, 3H), 7.43 (d, J=9.0 Hz, 1H), 7.99 (d, J=8.9 Hz, 1H), 8.99 (s, 2H); mass spectrum m/z 525 ((M+1)$^+$, 4.1%).

Example 3

Preparation of N-(8-{[(2S)-2-hydroxy-3-(morpholin-4-yl)propyl]oxy}-7-methoxy-2,3-dihydroimidazo[1,2-c]quinazolin-5-yl)pyridine-3-carboxamide

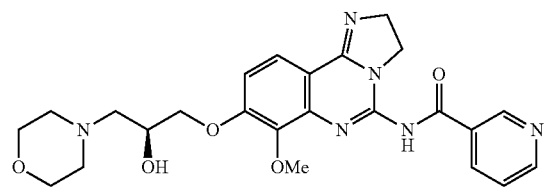 [SMILES: COc1c(OC[C@@H](O)CN2CCOCC2)ccc2c1N=C(NC(=O)c1cccnc1)N1CCN=C21]

Step 1: Preparation of (2S)-3-(4-morpholinyl)-1,2-propanediol

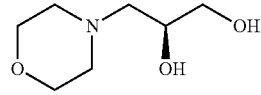

A solution of (R)-glycidol (0.33 mL, 5.0 mmol) and morpholine (0.65 mL, 7.5 mmol, 1.5 equiv.) in abs. ethanol was heated in a microwave for 4 min. at 140 0° C., cooled to room temperature and concentrated at 70° C. under a 12 mBar vacuum to afford (2S)-3-(4-morpholinyl)-1,2-propanediol (0.91 g, 113%): $^1$H NMR (CDCl3) δ 2.37 (dd, J=3.9, 12.5 Hz, 1H), 2.41-2.48 (m, 2H), 2.57 (dd, J=9.7, 12.5 Hz, 1H), 3.51 (dd, J=4.3, 11.4 Hz, 1H), 3.66-3.79 (m, 5H), 3.81-3.87 (m, 1H).

Step 2: Preparation of 4-[(4S)-(2-oxido-1,3,2-dioxa-thiolan-4-yl)methyl]morpholine hydrochloride

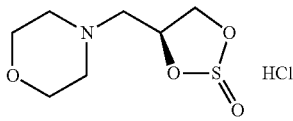

To a solution of (2S)-3-(4-morpholinyl)-1,2-propanediol (0.90 g, 5.6 mmol) in CH$_2$Cl$_2$ (7.5 mL) was cooled to 0° C. and added thionyl chloride (0.81 mL, 11.1 mmol, 2.0 equiv.) was added dropwise. The resulting solution was heated at the reflux temperature for 1 hr, cooled to room temperature and concentrated under reduced pressure to give 4-[(4S)-(2-oxido-1,3,2-dioxathiolan-4-yl)methyl]morpholine hydrochloride (1.40 g, 103%). This material was used in the next step without further purification.

Step 3: Preparation of N-(8-{[(2S)-2-hydroxy-3-(morpholin-4-yl)propyl]oxy}-7-methoxy-2,3-dihydroimidazo[1,2-c]quinazolin-5-yl)pyridine-3-carboxamide To a solution of N-(8-hydroxy-7-methoxy-2,3-dihydroimidazo[1,2-c]quinazolin-5-yl)nicotinamide bis-TFA salt (Intermediate I, Step 2, 0.210 g, 0.37 mmol) in DMF (12 mL) was added Cs$_2$CO$_3$ (0.61 g, 1.86 mmol, 5.0 equiv.) and the resulting slurry was stirred at room temperature for 1.5 hr, followed by the addition of cyclic sulfite ester (0.092 g, 0.45 mmol, 1.2 equiv). This mixture was stirred at 60° C. for 12 hr, cooled to room temperature, treated with additional caesium carbonate (0.86 g, 2.6 mmol, 2.0 equiv.) and cyclic sulfite ester (0.076 g, 0.37 mmol, 1.0 equiv.) and stirred at 60° C. for an additional 3.5 days. The resulting mixture was concentrated under reduced pressure. The residue was dissolved in a 4:1 CH$_2$Cl$_2$/isopropanol solution (50 mL), then was washed with a saturated NaHCO$_3$ (25 mL) and a saturated NaCl solution (25 mL), dried (an. Na$_2$SO$_4$), and concentrated under reduced pressure. Trituration with MeOH afforded crystals that were washed with water, then MeOH, and dried at 50° C. under reduced pressure. The resulting solids (0.077 g) were purified by preparative HPLC to give N-(8-{[(2S)-2-hydroxy-3-(morpholin-4-yl)propyl]oxy}-7-methoxy-2,3-dihydroimidazo[1,2-c]quinazolin-5-yl)pyridine-3-carboxamide (0.52 g, 82%): TLC (9:1 CH$_2$Cl$_2$/MeOH+1% NH$_4$OH in MeOH) R$_f$ 0.35; HPLC (condition A) ret. time 4.29 min.; $^1$H NMR (DMSO-d$_6$+1 drop TFA-d) δ 3.09-3.41 (m, 4H), 3.48 (br d, J=11.7 Hz, 2H), 3.62-3.85 (m, 2H), 3.88-4.01 (m, 2H), 4.03 (s, 3H), 4.20-4.31 (m, 4H), 4.41 (br s, 1H), 4.52-4.62 (m, 2H), 7.50 (d, J=9.4 Hz, 1H), 7.95 (dd, J=5.3, 7.9 Hz, 1H), 8.04 (d, J=9.2 Hz, 1H), 8.92 (br d, J=8.1 Hz, 1H), 8.98 (dd, J=1.1, 5.3 Hz, 1H), 9.49 (d, J=1.5 Hz, 1H).

Example 4

Preparation of N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]pyridine-3-carboxamide

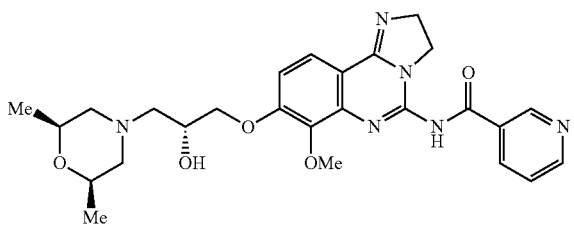 [SMILES: COc1c(OC[C@H](O)CN2C[C@@H](C)O[C@@H](C)C2)ccc2c1N=C(NC(=O)c1cccnc1)N1CCN=C21]

Step 1: Preparation of N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]amine

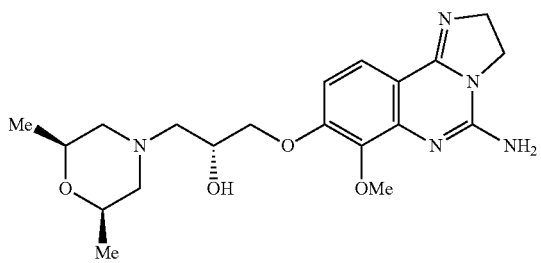 [SMILES: COc1c(OC[C@H](O)CN2C[C@@H](C)O[C@@H](C)C2)ccc2c1N=C(N)N1CCN=C21]

A solution of 7-Methoxy-8-[(2R)-oxiran-2-ylmethoxy]-2,3-dihydroimidazo[1,2-c]quinazolin-5-amine (Intermediate F, 1.50 g, 5.20 mmol) and cis-2,6-dimethylmorpholine (6.4 mL, 52.0 mmol, 10 equiv.) in DMF (36 mL) was heated in two portions in a microwave reactor for 45 min. at 140° C. The resulting combined mixtures were concentrated under reduced pressure and purified using MPLC to give N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]amine (2.02 g, 96%): Preparative HPLC ret. time 4.29 min.; $^1$H NMR (DMSO-d$_6$+1 drop TFA-d) δ 1.10 (d, J=7.3 Hz, 3H), 1.14 (d, J=7.3 Hz, 3H), 2.69 (t, J=11.6 Hz, 1H), 2.76 (t, J=11.6 Hz, 1H), 3.23-3.32 (m, 2H), 3.43-3.54 (m, 2H), 3.80 (s, 3H), 3.81-3.87 (m, 1H), 3.88-3.97 (m, 1H), 4.31 (app dd, J=8.6, 12.1 Hz, 2H), 4.35-4.43 (m, 1H), 7.22 (J=9.4 Hz, 1H), 7.81 (d, J=9.1 Hz, 1H); mass spectrum m/z 404 ((M+1)$^+$, 100%).

Step 2: Preparation of N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]pyridine-3-carboxamide A mixture of N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]amine (2.02 g, 5.01 mmol) and nicotinic acid (0.80 g, 6.51 mmol, 1.3 equiv) in DMF (139 mL) was treated with PyBOP (3.39 g, 6.51 mmol, 1.3 equiv.) followed by N,N-diisopropylethylamine (3.50 mL, 20.0 mmol, 4.0 equiv.) slowly leading to a clear solution. The mixture was stirred at room temperature for 24 h. The resulting solids were filtered and washed with DMF, H₂O, and MeOH, then dried at 60° C. under reduced pressure to give N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]pyridine-3-carboxamide (1.64 g, 64%): TLC (9:1 CH₂Cl₂/MeOH+1% NH₄OH in MeOH) R$_f$ 0.40; ¹H NMR (DMSO-d₆+1 drop TFA-d) δ 1.15 (d, J=9.5 Hz, 3H), 1.16 (d, J=9.5 Hz, 3H), 2.76 (t, J=11.2 Hz, 1H), 2.83 (t, J=11.4 Hz, 1H), 3.26-3.38 (m, 2H), 3.50-3.58 (m, 2H), 3.86-3.93 (m, 1H), 3.95-4.02 (m, 1H), 4.08 (s, 3H), 4.26-4.33 (m, 4H), 4.50 (br s, 1H), 4.61 (app t, J=10.7 Hz, 2H), 7.54 (d, J=9.1 Hz, 1H), 7.96 (dd, J=5.7, 7.6 Hz, 1H), 8.09 (d, J=9.1 Hz, 1H), 8.92 (d, J=7.9 Hz, 1H), 9.01 (d, J=4.1 Hz, 1H), 9.53 (s, 1H); mass spectrum m/z 507 ((M−1)⁻, 100%), 509 ((M+1)⁺, 24%).

The following examples were prepared in a manner analogous to Example 4:

Example 13

N-{8-[2-hydroxy-3-(morpholin-4-yl)propoxy]-7-methoxy-2,3-dihydroimidazo[1,2-c]quinazolin-5-yl}-2-methylpyridine-3-carboxamide

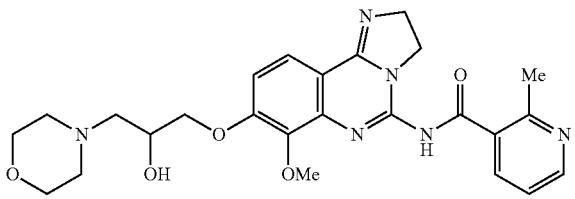

Prepared using Intermediate G in place of Intermediate F in Step 1 and 2-methyl-3-pyridinecarboxylic acid in place of nicotinic acid in Step 2 (50.0 mg, 58%): TLC (9:1 CH₂Cl₂/MeOH+1% NH₄OH in MeOH) R$_f$ 0.45; HPLC ret. time 0.81 min.; ¹H NMR (DMSO-d₆+1 drop TFA-d) δ 3.00 (s, 3H), 3.10-3.40 (m, 4H), 3.48 (br d, J=12.1 Hz, 2H), 3.64-3.83 (m, 2H), 3.89-4.02 (m, 2H), 4.02 (s, 3H), 4.18-4.28 (m, 4H), 4.38-4.46 (m, 1H), 4.46-4.55 (m, 2H), 7.50 (d, J=9.0 Hz, 1H), 7.96 (dd, J=6.2, 7.5 Hz, 1H), 8.05 (d, J=9.0 Hz, 1H), 8.91 (d, J=5.5 Hz, 1H), 9.06 (br d, J=8.3 Hz, 1H); mass spectrum m/z 495 ((M+1)⁺, 5.5%).

Example 5

Preparation of N-(8-{[(2R)-2-hydroxy-3-(8-oxa-3-azabicyclo[3.2.1]oct-3-yl)propyl]oxy}-7-methoxy-2,3-dihydroimidazo[1,2-c]quinazolin-5-yl)pyridine-3-carboxamide

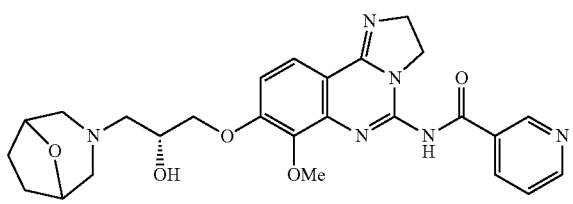 [SMILES: COc1c(OC[C@H](O)CN2CC3CCC(C2)O3)ccc2c1N=C(NC(=O)c1cccnc1)N1CCN=C21]

Step 1: Preparation of N-(8-{[(2R)-2-hydroxy-3-(8-oxa-3-azabicyclo[3.2.1]oct-3-yl)propyl]oxy}-7-methoxy-2,3-dihydroimidazo[1,2-c]quinazolin-5-ylamine

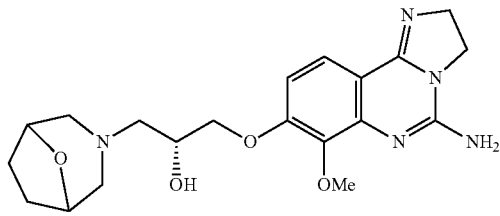 [SMILES: COc1c(OC[C@H](O)CN2CC3CCC(C2)O3)ccc2c1N=C(N)N1CCN=C21]

A solution of 7-methoxy-8-[(2R)-oxiran-2-ylmethoxy]-2,3-dihydroimidazo[1,2-c]quinazolin-5-amine (Intermediate F, 0.195 g, 0.68 mmol) and 8-oxa-3-azabicyclo[3.2.1]octane hydrochloride (0.506 g, 3.38 mmol, 10 equiv.) in DMF (4.5 mL) was heated in a microwave reactor for 45 min. at 140° C. The resulting mixture was concentrated under reduced pressure. The residue was treated with a 4:1 CH₂Cl₂/isopropanol solution (25 mL), washed with a saturated sodium bicarbonate solution (25 mL), dried (an. sodium sulfate) and concentrated under reduced pressure. The resulting residue was purified using MPLC to give N-(8-{[(2R)-2-hydroxy-3-(8-oxa-3-azabicyclo[3.2.1]oct-3-yl)propyl]oxy}-7-methoxy-2,3-dihydroimidazo[1,2-c]quinazolin-5-ylamine (0.74 g, 16%): HPLC ret. time 0.70 min.; mass spectrum m/z 402 ((M+1)⁺, 7%).

Step 2: Preparation of N-(8-{[(2R)-2-hydroxy-3-(8-oxa-3-azabicyclo[3.2.1]oct-3-yl)propyl]oxy}-7-methoxy-2,3-dihydroimidazo[1,2-c]quinazolin-5-yl)pyridine-3-carboxamide A mixture of N-(8-{[(2R)-2-hydroxy-3-(8-oxa-3-azabicyclo[3.2.1]oct-3-yl)propyl]oxy}-7-methoxy-2,3-dihydroimidazo[1,2-c]quinazolin-5-ylamine (70.0 mg, 0.17 mmol) and nicotinic acid (26.0 mg, 0.22 mmol, 1.3 equiv) in DMF (2.5 mL) was treated with PyBOP (11.3 mg, 0.22 mmol, 1.3 equiv.) followed by N,N-diisopropylethylamine (0.12 mL, 0.70 mmol, 4.0 equiv) slowly leading to a clear solution. The mixture was stirred at room temperature for 2 days. The reaction mixture was concentrated under reduced pressure. The residue was separated between water (10 mL) and a 4:1 CH₂Cl₂/isopropanol solution (10 mL). The organic phase was washed with a saturated sodium bicarbonate solution, dried (an. sodium sulfate) and concentrated under reduced pressure. The resulting residue was purified using MPLC to give partially purified material (36.6 mg), which was further purified using preparative HPLC to give N-(8-{[(2R)-2-hydroxy-3-(8-oxa-3-azabicyclo[3.2.1]oct-3-yl)propyl]oxy}-7-methoxy-2,3-dihydroimidazo[1,2-c]quinazolin-5-yl)pyridine-3-carboxamide (10.0 mg, 11%): HPLC ret. time 0.98 min.; ¹H NMR (DMSO-d₆+1 drop TFA-d) δ 1.85-2.00 (m, 3H), 2.10-2.19 (m, 1H), 3.24 (app t, J=11.5 Hz, 2H), 3.29-3.38 (m, 2H), 3.44 (d, J=11.9 Hz, 2H), 4.02 (s, 3H), 4.20-4.29 (m, 4H), 4.41 (br s, 1H), 4.49 (br app t, J=8.1 Hz, 2H), 4.57 (t, J=9.7 Hz, 2H), 7.49 (d, J=9.4 Hz, 1H), 8.00-8.06 (m, 1H), 8.04 (d, J=11.1 Hz, 1H), 8.98-9.04 (m, 2H), 9.52 (d, J=1.8 Hz, 1H); mass spectrum m/z 507 ((M+1)⁺, 3%).

The following examples were prepared in a manner analogous to Example 5:

Example 16

N-(8-{[(2R)-3-(Azetidin-1-yl)-2-hydroxypropyl]oxy}-7-methoxy-2,3-dihydroimidazo[1,2-c]quinazolin-5-yl)-2-methylpyridine-3-carboxamide

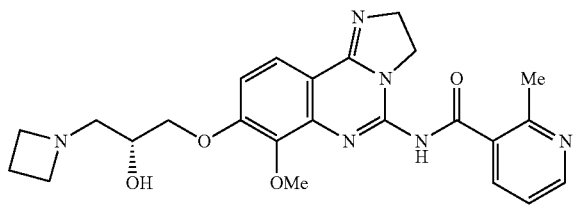 [SMILES: COc1c(OC[C@H](O)CN2CCC2)ccc2c1N=C(NC(=O)c1cccnc1C)N1CCN=C21]

Prepared using aziridine in place of 8-oxa-3-azabicyclo[3.2.1]octane hydrochloride in Step 1, and using 2-methyl-3-pyridinecarboxylic acid in place of nicotinic acid in Step 2 (78.0 mg, 41%): $^1$H NMR (DMSO-$d_6$+1 drop TFA-d) δ 2.99 (s, 3H), 3.19-3.29 (m, 1H), 3.34-3.42 (m, 1H), 4.01 (s, 3H), 4.06-4.18 (m, 6H), 4.18-4.27 (m, 4H), 4.45-4.55 (m, 2H), 7.49 (d, J=9.2 Hz, 1H), 7.96 (dd, J=5.8, 7.5 Hz, 1H), 8.04 (d, J=9.2 Hz, 1H), 8.91 (dd, J=1.5, 5.7 Hz, 1H), 9.07 (br d, J=7.5 Hz, 1H); mass spectrum m/z 465 ((M+1)$^+$, 3.6%).

Example 17

N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]-2-methylpyridine-3-carboxamide

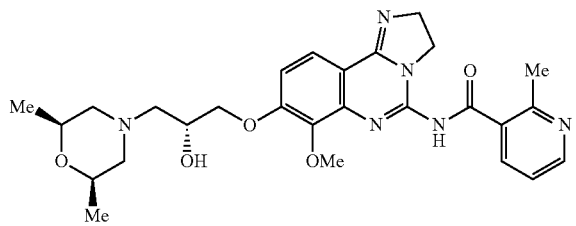 [SMILES: COc1c(OC[C@H](O)CN2C[C@@H](C)O[C@@H](C)C2)ccc2c1N=C(NC(=O)c1cccnc1C)N1CCN=C21]

Prepared using cis-2,6-dimethylmorpholine in place of 8-oxa-3-azabicyclo[3.2.1]octane hydrochloride in Step 1, and using 2-methyl-3-pyridinecarboxylic acid in place of nicotinic acid in Step 2 (0.67 g, 51%): HPLC ret. time 1.00 min.; $^1$H NMR (DMSO-$d_6$+1 drop TFA-d) δ 1.10 (d, J=5.8 Hz, 3H), 1.13 (d, J=5.8 Hz, 3H), 2.66-2.83 (m, 2H), 2.99 (s, 3H), 3.20-3.34 (m, 2H), 3.49 (app br t, J=12.0, 2H), 3.81-3.98 (m, 2H), 4.02 (s, 3H), 4.18-4.29 (m, 4H), 4.41-4.55 (m, 3H), 7.50 (d, J=9.2 Hz, 1H), 7.94 (dd, J=5.7, 7.5 Hz, 1H), 8.05 (d, J=9.0 Hz, 1H), 8.91 (dd, J=1.5, 7.2 Hz, 1H), 9.04 (br d, J=6.6 Hz, 1H); mass spectrum m/z 521 ((M-1)$^-$, 18%), 523 ((M+1)$^+$, 3.8%).

Example 28

2-Amino-N-(8-{[(2R)-2-hydroxy-3-(8-oxa-3-azabicyclo[3.2.1]oct-3-yl)propyl]oxy}-7-methoxy-2,3-dihydroimidazo[1,2-c]quinazolin-5-yl)pyrimidine-5-carboxamide dihydrochloride

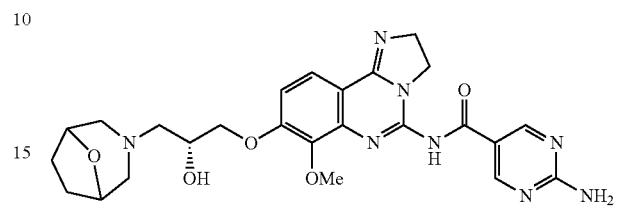

Prepared using 2-amino-5-pyrimidinecarboxylic acid in place of nicotinic acid in Step 2. The title compound was isolated as the bis-HCl salt (48.9 mg, 25%): HPLC ret. time 0.86 min.; $^1$H NMR (DMSO-$d_6$+1 drop TFA-d) δ 1.85-2.00 (m, 2H), 2.09-2.18 (m, 1H), 3.17-3.48 (m, 5H), 3.82-3.90 (m, 1H), 3.98 (s, 3H), 4.12-4.28 (m, 4H), 4.35-4.43 (m, 1H), 4.43-54 (m, 3H), 7.42 (d, J=9.4 Hz, 1H), 7.98 (d, J=9.0 Hz, 1H), 9.00 (s, 2H); mass spectrum m/z 524 ((M+1)$^+$, 0.2%).

Example 34

N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]-1,3-thiazole-5-carboxamide

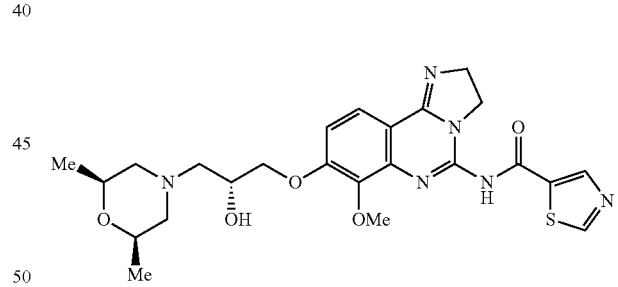

Prepared using cis-2,6-dimethylmorpholine in place of 8-oxa-3-azabicyclo[3.2.1]octane hydrochloride in Step 1, and using 1,3-thiazole-5-carboxylic acid in place of nicotinic acid in Step 2 (82.0 mg, 69%): HPLC ret. time 1.01 min.; $^1$H NMR (DMSO-$d_6$+1 drop TFA-d) δ 1.10 (d, J=6.0 Hz, 3H), 1.13 (d, J=6.0 Hz, 3H), 2.66-2.82 (m, 2H), 3.23-3.31 (m, 2H), 3.49 (app br t, J=12.0, 2H), 3.79-3.97 (m, 2H), 4.01 (s, 3H), 4.16-4.27 (m, 4H), 4.41-4.50 (m, 3H), 7.46 (d, J=9.0 Hz, 1H), 8.01 (d, J=9.0 Hz, 1H), 8.61 (s, 1H), 9.31 (s, 1H); mass spectrum m/z 513 ((M-1)$^-$, 0.4%), 515 ((M+1)$^+$, 0.9%).

Example 35

N-(8-{[(2R)-3-(Azetidin-1-yl)-2-hydroxypropyl]oxy}-7-methoxy-2,3-dihydroimidazo[1,2-c]quinazolin-5-yl)-1,3-thiazole-5-carboxamide

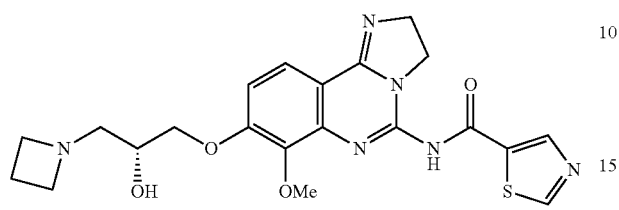

Prepared using azetidine in place of 8-oxa-3-azabicyclo[3.2.1]octane hydrochloride in Step 1, and using 1,3-thiazole-5-carboxylic acid in place of nicotinic acid in Step 2 (5.0 mg, 2.4%): $^1$H NMR (DMSO-d$_6$+1 drop TFA-d) δ 2.72-2.87 (m, 2H), 3.18-3.28 (m, 2H), 3.33-3.45 (m, 2H), 4.00 (s, 3H), 4.05-4.25 (m, 6H), 4.40-4.50 (m, 3H), 7.44 (d, J=9.0 Hz, 1H), 8.00 (d, J=9.0 Hz, 1H), 8.61 (s, 1H), 9.31 (s, 1H); mass spectrum m/z 457 ((M+1)$^+$, 1.0%).

Example 6

Preparation of N-{8-[2-hydroxy-3-(thiomorpholin-4-yl)propoxy]-7-methoxy-2,3-dihydroimidazo[1,2-c]quinazolin-5-yl}pyridine-3-carboxamide

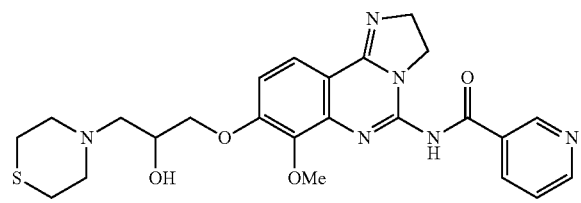 [SMILES: COc1c(OCC(O)CN2CCSCC2)ccc2c1N=C(NC(=O)c1cccnc1)N1CCN=C21]

A mixture of N-[7-methoxy-8-(oxiran-2-ylmethoxy)-2,3-dihydroimidazo[1,2-c]quinazolin-5-yl]nicotinamide (Intermediate I, 7.6 mL of 0.120 M solution in DMF, 0.92 mmol) and thiomorpholine (0.46 mL, 4.60 mmol, 5.0 equiv.) was heated in a microwave reactor for 30 min. at 140° C. The resulting mixture was concentrated under reduced pressure, and the residue was dissolved in a 4:1 CH$_2$Cl$_2$/isopropanol solution (50 mL). The resulting solution was washed with a saturated NaHCO$_3$ solution (25 mL), dried (an. Na$_2$SO$_4$), and concentrated under reduced pressure. The resulting residue was purified using MPLC to yield impure product (128 mg) that was further purified using preparative HPLC to give N-{8-[2-hydroxy-3-(thiomorpholin-4-yl)propoxy]-7-methoxy-2,3-dihydroimidazo[1,2-c]quinazolin-5-yl}pyridine-3-carboxamide (34.0 mg, 7%): HPLC ret. time 0.61 min.; $^1$H NMR (DMSO-d$_6$+1 drop TFA-d) δ 2.75-3.05 (m, 3H), 3.05-3.44 (m, 4H), 4.02 (s, 3H), 4.19-4.28 (m, 4H), 4.43 (br s, 1H), 4.55 (br app t, J=9.8 Hz, 2H), 7.47 (d, J=9.1 Hz, 1H), 7.77 (dd, J=5.3, 7.8, 1H), 8.02 (d, J=9.1 Hz, 1H), 8.72 (br d, J=7.8 Hz, 1H), 8.89 (dd, J=1.5, 5.1 Hz, 1H), 9.43 (br s, 1H); mass spectrum m/z 507 ((M−1)$^-$, 100%), 509 ((M+1)$^+$, 24%).

The following examples were prepared in a manner analogous to Example 6:

Example 10

N-{8-[3-(dimethylamino)-2-hydroxypropoxy]-7-methoxy-2,3-dihydroimidazo[1,2-c]quinazolin-5-yl}pyridine-3-carboxamide

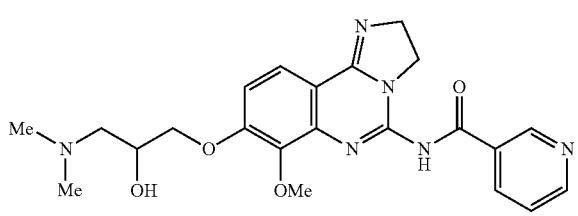 [SMILES: COc1c(OCC(O)CN(C)C)ccc2c1N=C(NC(=O)c1cccnc1)N1CCN=C21]

Prepared using dimethylamine in place of thiomorpholine in Step 1 (0.14 g, 68%): HPLC ret. time 0.52 min.; $^1$H NMR (DMSO-d$_6$+1 drop TFA-d) δ 2.82 (s, 3H), 2.86 (s, 3H), 3.18-3.30 (m, 2H), 4.03 (s, 3H), 4.20-4.28 (m, 4H), 4.31-4.38 (m, 1H), 4.52-4.59 (m, 2H), 7.48 (d, J=9.4 Hz, 1H), 7.76 (dd, J=5.1, 7.8 Hz, 1H), 8.03 (d; J=9.1 Hz, 1H), 8.71 (br d, J=7.8 Hz, 1H), 8.88, (dd, J=1.5, 5.1 Hz, 1H), 9.44 (d, J=1.5 Hz, 1H); mass spectrum m/z 439 ((M+1)$^+$, 4.6%).

Example 11

N-(8-{[(2R)-3-(dimethylamino)-2-hydroxypropyl]oxy}-7-methoxy-2,3-dihydroimidazo[1,2-c]quinazolin-5-yl)pyridine-3-carboxamide

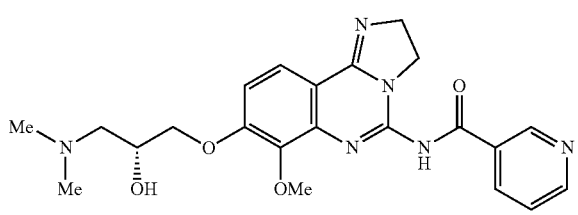 [SMILES: COc1c(OC[C@H](O)CN(C)C)ccc2c1N=C(NC(=O)c1cccnc1)N1CCN=C21]

Prepared using dimethylamine in place of thiomorpholine and Intermediate J in place of Intermediate I in Step 1 (0.14 g, 68%): HPLC ret. time 0.91 min.; $^1$H NMR (DMSO-d$_6$+1 drop TFA-d) δ 2.82 (s, 3H), 2.86 (s, 3H), 3.17-3.30 (m, 2H), 4.03 (s, 3H), 4.19-4.29 (m, 4H), 4.31-4.38 (m, 1H), 4.52-4.60 (m, 2H), 7.48 (d, J09.4 Hz, 1H), 7.93 (dd, J=5.1, 7.8 Hz, 1H), 8.04 (d, J09.1 Hz, 1H), 8.90 (br d; J=8.1 Hz, 1H), 8.97, (br d, J=5.1 Hz, 1H), 9.49 (br s, 1H); mass spectrum m/z 439 ((M+1)$^+$, 2.5%).

Example 12

N-(8-{[(2R)-3-(dipropan-2-ylamino)-2-hydroxypropyl]oxy}-7-methoxy-2,3-dihydroimidazo[1,2-c]quinazolin-5-yl)pyridine-3-carboxamide

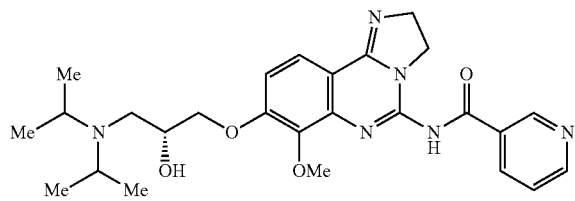 [SMILES: COc1c(OC[C@H](O)CN(C(C)C)C(C)C)ccc2c1N=C(NC(=O)c1cccnc1)N1CCN=C21]

Prepared using diisopropylamine in place of thiomorpholine and Intermediate J in place of Intermediate I in Step 1 (22.0 mg, 16%): HPLC ret. time 1.29 min.; $^1$H NMR (DMSO-$d_6$+1 drop TFA-d) δ 1.22-1.34 (m, 12H), 3.14-3.21 (m, 1H), 3.35 (br d, J=14.3 Hz, 1H), 3.63-3.78 (m, 2H), 4.01 (s, 3H), 4.19-4.31 (m, 5H), 4.52-4.61 (m, 2H), 7.49 (d, J=9.2 Hz, 1H), 7.93 (dd, J=5.7, 8.1 Hz, 1H), 8.06 (d, J=9.0 Hz, 1H), 8.90 (br d, J=8.1 Hz, 1H), 8.97 (dd, J=1.5, 5.3 Hz, 1H), 9.49, (d, J=1.5 Hz, 1H); mass spectrum m/z 495 ((M+1)$^+$, 11%).

Example 29

2-Amino-N-(8-{[(2R)-3-(dimethylamino)-2-hydroxypropyl]oxy}-7-methoxy-2,3-dihydroimidazo[1,2-c]quinazolin-5-yl)pyrimidine-5-carboxamide

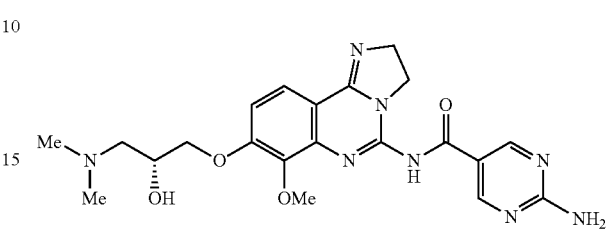

Prepared using dimethylamine in place of thiomorpholine and Intermediate J in place of Intermediate I in Step 1, and using 2-amino-5-pyrimidinecarboxylic acid in place of nicotinic acid in Step 2 (65.0 mg, 39%): HPLC ret. time 0.79 min.; $^1$H NMR (DMSO-$d_6$+1 drop TFA-d) δ 2.82 (s, 3H), 2.85 (s, 3H), 3.15-3.27 (m, 2H), 3.99 (s, 3H), 4.15-4.25 (m, 4H), 4.29-4.38 (m, 1H), 4.44-4.54 (m, 2H), 7.42 (d, J=9.2 Hz, 1H), 7.99 (d, J=9.0 Hz, 1H), 9.02 (s, 2H); mass spectrum m/z 455 ((M+1)$^+$, 3.7%).

Example 20

N-(8-{[(2R)-3-(dipropan-2-ylamino)-2-hydroxypropyl]oxy}-7-methoxy-2,3-dihydroimidazo[1,2-c]quinazolin-5-yl)-2-methylpyridine-3-carboxamide

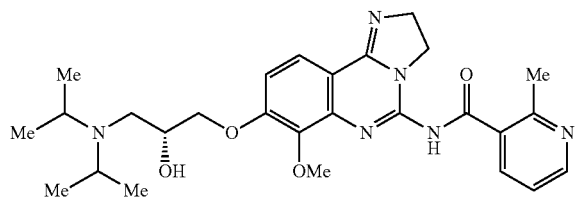 [SMILES: COc1c(OC[C@H](O)CN(C(C)C)C(C)C)ccc2c1N=C(NC(=O)c1cccnc1C)N1CCN=C21]

Prepared using diisopropylamine in place of thiomorpholine and Intermediate J in place of Intermediate I in Step 1, and using 2-methyl-3-pyridinecarboxylic acid in place of nicotinic acid in Step 2 (0.66 g, 70%): HPLC ret. time 1.33 min.; $^1$H NMR (DMSO-$d_6$+1 drop TFA-d) δ 1.23-1.33 (m, 12H), 3.00 (s, 3H), 3.16 (dd, J=10.1, 14.1 Hz, 1H), 3.34 (dm, J=14.1, 1H), 3.70 (sept, J=6.8 Hz, 2H), 4.00 (s, 3H), 4.20-4.31 (m, 5H), 4.47-4.54 (m, 2H), 7.50 (d, J=9.4 Hz, 1H), 7.99 (dd, J=5.8, 7.8 Hz, 1H), 8.06 (d, J=9.1 Hz, 1H), 8.93 (dd, J=1.5, 5.8 Hz, 1H), 9.11 (br d, J=7.1 Hz, 1H); mass spectrum m/z 509 ((M+1)$^+$, 2.7%).

Example 41

N-(8-{[(2R)-3-(dipropan-2-ylamino)-2-hydroxypropyl]oxy}-7-methoxy-2,3-dihydroimidazo[1,2-c]quinazolin-5-yl)-1,3-thiazole-5-carboxamide

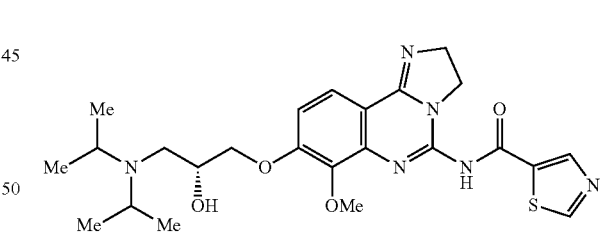

Prepared using diisopropylamine in place of thiomorpholine and Intermediate J in place of Intermediate I in Step 1, and using 1,3-thiazole-5-carboxylic acid in place of nicotinic acid in Step 2 (0.48 g, 55%): HPLC ret. time 1.03 min.; $^1$H NMR (DMSO-$d_6$+1 drop TFA-d) δ 1.23-1.33 (m, 12H), 3.16 (dd, J=9.9, 14.4 Hz, 1H), 3.34 (dm, J=14.2, 1H), 3.70 (sept, J=6.6 Hz, 2H), 4.00 (s, 3H), 4.18-4.25 (m, 3H), 4.27-4.29 (m, 2H), 4.42-4.49 (m, 2H), 7.50 (d, J=9.4 Hz, 1H), 8.02 (d, J=9.4 Hz, 1H), 8.61 (s, 1H), 9.32 (s, 1H); mass spectrum m/z 501 ((M+1)$^+$, 2.3%).

Example 7

Preparation of N-(8-{[(2R)-3-(azetidin-1-yl)-2-hydroxypropyl]oxy}-7-methoxy-2,3-dihydroimidazo[1,2-c]quinazolin-5-yl)pyridine-3-carboxamide

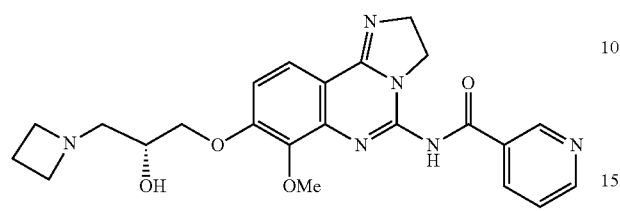

Step 1: Preparation of N-(8-{[(2R)-3-(azetidin-1-yl)-2-hydroxypropyl]oxy}-7-methoxy-2,3-dihydroimidazo[1,2-c]quinazolin-5-yl)amine

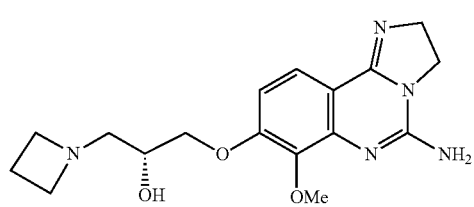 [SMILES: COc1c(OC[C@H](O)CN2CCC2)ccc2c1N=C(N)N1CCN=C21]

A solution of 7-Methoxy-8-[(2R)-oxiran-2-ylmethoxy]-2,3-dihydroimidazo[1,2-c]quinazolin-5-amine (Intermediate F, 0.35 g, 1.21 mmol) and azetidine (0.82 mL, 12.1 mmol, 10 equiv.) in DMF (10 mL) was heated in a microwave reactor for 45 min. at 140° C. The resulting mixture was concentrated under reduced pressure and purified using MPLC to give N-(8-{[(2R)-3-(azetidin-1-yl)-2-hydroxypropyl]oxy}-7-methoxy-2,3-dihydroimidazo[1,2-c]quinazolin-5-yl)amine (0.48 g, 115%): HPLC ret. time 0.67 min.; mass spectrum m/z 346 ((M+1)$^+$, 100%).

Step 2: Preparation of N-(8-{[(2R)-3-(azetidin-1-yl)-2-hydroxypropyl]oxy}-7-methoxy-2,3-dihydroimidazo[1,2-c]quinazolin-5-yl)pyridine-3-carboxamide To a slurry of N-(8-{[(2R)-3-(azetidin-1-yl)-2-hydroxypropyl]oxy}-7-methoxy-2,3-dihydroimidazo[1,2-c]quinazolin-5-yl)amine (0.128 g, 0.37 mmol) and nicotinic acid (0.057 g, 0.46 mmol, 1.3 equiv.) in DMF (4 mL) was added PyBOP (241 mg, 0.46 mmol, 1.3 equiv.) followed by diisopropylethylamine (0.25 mL, 1.48 mmol, 4.0 equiv.). The resulting mixture was stirred at room temperature. After a few hours the mixture turned to a clear solution. The resulting solution was stirred at room temperature for 48 h, then was concentrated under reduced pressure. The residue was separated between water 25 mL, and a 4:1 CH$_2$Cl$_2$/isopropanol solution (25 mL). The resulting organic phase was washed with a saturated sodium bicarbonate solution, dried (an. sodium sulfate) and concentrated under reduced pressure. The resulting material purified using MPLC to give partially purified material (82 mg), which was further purified using preparative HPLC, then triturated with ethyl ether to afford N-(8-{[(2R)-3-(azetidin-1-yl)-2-hydroxypropyl]oxy}-7-methoxy-2,3-dihydroimidazo[1,2-c]quinazolin-5-yl)pyridine-3-carboxamide (0.050 g, 28%): HPLC ret. time 0.91 min.; $^1$H NMR (DMSO-d$_6$+1 drop TFA-d) δ 2.18-2.28 (m, 1H), 2.37-2.45 (m, 1H), 3.24 (dd, J=9.8, 12.8 Hz, 1H), 3.38 (dd, J=2.5, 12.6 Hz, 1H), 4.02 (s, 3H), 4.06-4.18 (m, 5H), 4.21 (app t, J=4.9 Hz, 2H), 4.23-4.29 (m, 2H), 4.52-4.60 (m, 2H), 7.48 (d, J=9.4 Hz, 1H), 7.88 (dd, J=5.3, 7.6 Hz, 1H), 8.30 (d, J=9.1 Hz, 1H), 8.85 (br d, J=8.1 Hz, 1H), 8.95 (dd, J=1.5, 6.8 Hz, 1H), 9.48 (d, J=1.5 Hz, 1H); mass spectrum m/z 451 ((M+1)$^+$, 0.2%).

Example 8

Preparation of N-(8-{[(2R)-2-hydroxy-3-(pyrrolidin-1-yl)propyl]oxy}-7-methoxy-2,3-dihydroimidazo[1,2-c]quinazolin-5-yl)pyridine-3-carboxamide

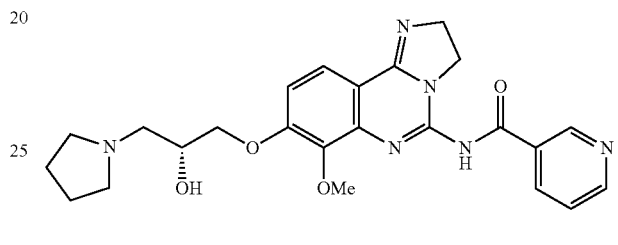

Step 1: Preparation of N-(8-{[(2R)-2-hydroxy-3-(pyrrolidin-1-yl)propyl]oxy}-7-methoxy-2,3-dihydroimidazo[1,2-c]quinazolin-5-yl)amine

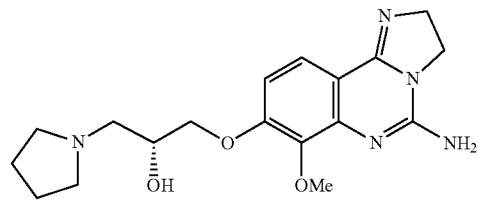 [SMILES: COc1c(OC[C@H](O)CN2CCCC2)ccc2c1N=C(N)N1CCN=C21]

A solution of 7-Methoxy-8-[(2R)-oxiran-2-ylmethoxy]-2,3-dihydroimidazo[1,2-c]quinazolin-5-amine (Intermediate F, 1.00 g, 3.47 mmol) and pyrrolidine (2.87 mL, 34.7 mmol, 10 equiv.) in DMF (18 mL) was in a microwave reactor for 45 min. at 140° C. The resulting mixture was concentrated under reduced pressure. The residue (2.5 g) was purified using MPLC to give N-(8-{[(2R)-2-hydroxy-3-(pyrrolidin-1-yl)propyl]oxy}-7-methoxy-2,3-dihydroimidazo[1,2-c]quinazolin-5-yl)amine (0.97 g, 78%): HPLC ret. time 0.71 min.; $^1$H NMR (DMSO-d$_6$+1 drop TFA-d) δ 1.82-1.92 (m, 2H), 1.94-2.03 (m, 2H), 3.02-3.14 (m, 3H), 3.27-3.33 (m, 2H), 3.52-3.61 (m, 2H), 3.80 (s, 3H), 4.06-4.16 (m, 4H), 4.23 (br sextet, J=4.3 Hz, 1H), 4.28-4.34 (m, 2H), 7.22 (d, J=9.4 Hz, 1H), 7.81 (d, J=9.1 Hz, 1H); mass spectrum m/z 360 ((M+1)$^+$, 100%).

Step 2: Preparation of N-(8-{[(2R)-2-hydroxy-3-(pyrrolidin-1-yl)propyl]oxy}-7-methoxy-2,3-dihydroimidazo[1,2-c]quinazolin-5-yl)pyridine-3-carboxamide To a slurry of N-(8-{[(2R)-2-hydroxy-3-(pyrrolidin-1-yl)propyl]oxy}-7-methoxy-2,3-dihydroimidazo[1,2-c]quinazolin-5-yl)amine (0.250 g, 0.70 mmol) and nicotinic acid (0.107 g, 0.87 mmol, 1.3 equiv.) in DMF (10 mL) was added PyBOP (0.452 g, 0.87 mmol, 1.3 equiv.) followed by diisopropylethylamine (0.48 mL, 2.78 mmol, 4.0 equiv.). The resulting mixture was stirred at room temperature. After a few hours the mixture turned to a clear solution. The resulting solution was stirred at room temperature for 24 h, then was concentrated under reduced pressure. The residue was separated between water (25 mL) and a 4:1 CH$_2$Cl$_2$/isopropanol solution (50 mL). The resulting organic phase was washed with a saturated sodium bicarbonate solution, dried (an. sodium sulfate) and concentrated under reduced pressure. The resulting material (0.588 g) purified using MPLC to afford N-(8-{[(2R)-2-hydroxy-3-(pyrrolidin-1-yl)propyl]oxy}-7-methoxy-2,3-dihydroimidazo[1,2-c]quinazolin-5-yl)pyridine-3-carboxamide (0.16 g, 50%): HPLC ret. time 1.00 min.; $^1$H NMR (DMSO-d$_6$+1 drop TFA-d) δ 1.83-1.93 (m, 2H), 1.93-2.05 (m, 2H), 3.04-3.15 (m, 2H), 3.29-3.34 (m, 2H), 3.53-3.62 (m, 2H), 4.03 (s, 3H), 4.20-4.32 (m, 5H), 4.53-4.60 (m, 2H), 7.48 (d, J=9.1 Hz), 7.88 (dd, J=5.6, 8.1 Hz, 1H), 8.03 (d, J=9.1 Hz, 1H), 8.84, (br d, J=8.1 Hz, 1H), 8.94 (dd, J=1.5, 5.3 Hz, 1H), 9.47 (d, J=1.5 Hz, 1H); mass spectrum m/z 465 ((M+1)$^+$, 17%).

The following examples were prepared in a manner analogous to Example 8:

Example 18

N-(8-{[(2R)-2-hydroxy-3-(pyrrolidin-1-yl)propyl]oxy}-7-methoxy-2,3-dihydroimidazo[1,2-c]quinazolin-5-yl)-2-methylpyridine-3-carboxamide

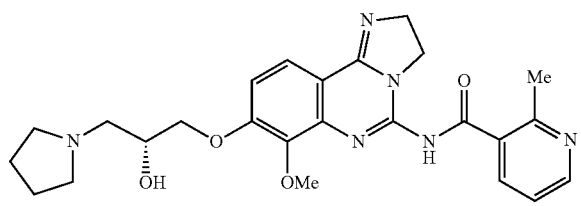 [SMILES: COc1c(OC[C@H](O)CN2CCCC2)ccc2c1N=C(NC(=O)c1cccnc1C)N1CCN=C21]

Prepared using 2-methyl-3-pyridinecarboxylic acid in place of nicotinic acid in Step 2 (0.13 g, 40%): HPLC ret. time 1.01 min.; $^1$H NMR (DMSO-d$_6$+1 drop TFA-d) δ 1.84-1.93 (m, 2H), 1.95-2.05 (m, 2H), 2.99 (s, 3H), 3.06-3.15 (m, 2H), 3.28-3.34 (m, 2H), 3.53-3.62 (m, 2H), 4.02 (s, 3H), 4.19-4.33 (m, 5H), 4.46-4.54 (m, 2H), 7.50 (d, J=9.1 Hz, 1H), 7.95 (app t, J=6.5 Hz, 1H), 8.04 (d, J=9.1 Hz, 1H), 8.91 (br d, J=4.6 Hz, 1H), 9.06 (br s, 1H); mass spectrum m/z 479 ((M+1)$^+$, 2.3%).

Example 24

N-(8-{[(2R)-2-hydroxy-3-(pyrrolidin-1-yl)propyl]oxy}-7-methoxy-2,3-dihydroimidazo[1,2-c]quinazolin-5-yl)pyrimidine-5-carboxamide

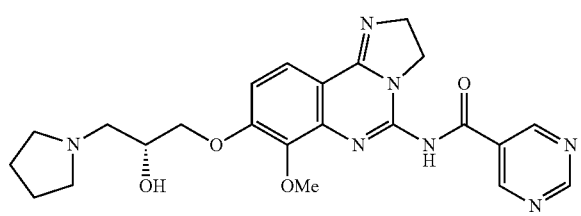 [SMILES: COc1c(OC[C@H](O)CN2CCCC2)ccc2c1N=C(NC(=O)c1cncnc1)N1CCN=C21]

Prepared using 5-pyrimidinecarboxylic acid in place of nicotinic acid in Step 2 (77.4 mg, 54%): $^1$H NMR (DMSO-d$_6$+1 drop TFA-d) δ 1.83-1.92 (m, 2H), 1.96-2.04 (m, 2H), 3.06-3.15 (m, 2H), 3.29-3.32 (m, 2H), 3.53-3.62 (m, 2H), 4.03 (s, 3H), 4.19-4.33 (m, 5H), 4.54-4.60 (m, 2H), 7.48 (d, J=9.4 Hz, 1H), 8.03 (d, J=9.4 Hz, 1H), 9.38 (s, 1H), 9.47 (s, 2H); mass spectrum m/z 464 ((M−1)$^-$, 100%), 466 ((M+1)$^+$, 7.2%).

Example 36

N-(8-{[(2R)-2-Hydroxy-3-(pyrrolidin-1-yl)propyl]oxy}-7-methoxy-2,3-dihydroimidazo[1,2-c]quinazolin-5-yl)-1,3-thiazole-5-carboxamide

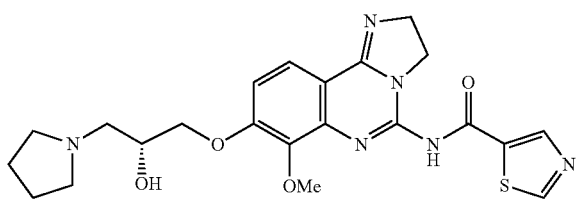 [SMILES: COc1c(OC[C@H](O)CN2CCCC2)ccc2c1N=C(NC(=O)c1cncs1)N1CCN=C21]

Prepared using 1,3-thiazole-5-carboxylic acid in place of nicotinic acid in Step 2 (0.11 g, 81%): $^1$H NMR (DMSO-d$_6$+1 drop TFA-d) δ 1.84-1.91 (m, 2H), 1.96-2.03 (m, 2H), 3.06-3.14 (m, 2H), 3.29-3.33 (m, 2H), 3.53-3.62 (m, 2H), 4.01 (s, 3H), 4.18-4.25 (m, 4H), 4.25-4.32 (m, 1H), 4.42-4.48 (m, 2H), 7.45 (d, J=9.4 Hz, 1H), 8.02 (d, J=9.4 Hz, 1H), 8.61 (s, 1H), 9.31 (s, 2H); mass spectrum m/z 469 ((M−1)$^-$, 4.9%), 471 ((M+1)$^+$, 1.8%).

Example 38

N-(8-{[(2R)-2-Hydroxy-3-(pyrrolidin-1-yl)propyl]oxy}-7-methoxy-2,3-dihydroimidazo[1,2-c]quinazolin-5-yl)-4-methyl-1,3-thiazole-5-carboxamide

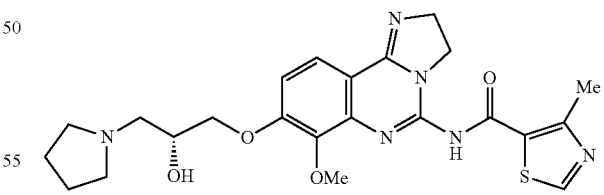

Prepared using 4-methyl-1,3-thiazole-5-carboxylic acid in place of nicotinic acid in Step 2 (0.078 g, 55%): $^1$H NMR (DMSO-d$_6$+1 drop TFA-d) δ 1.85-1.94 (m, 2H), 1.98-2.06 (m, 2H), 2.78 (s, 3H), 3.08-3.17 (m, 2H), 3.30-3.37 (m, 2H), 3.56-3.65 (m, 2H), 4.04 (s, 3H), 4.19-4.27 (m, 4H), 4.28-4.34 (m, 1H), 4.44-4.48 (m, 2H), 7.46 (d, J=9.3 Hz, 1H), 8.02 (d, J=9.3 Hz, 1H), 9.15 (s, 2H); mass spectrum m/z 483 ((M−1)$^-$, 22%), 485 ((M+1)$^+$, 0.9%).

Example 40

N-(8-{[(2R)-2-Hydroxy-3-(pyrrolidin-1-yl)propyl]oxy}-7-methoxy-2,3-dihydroimidazo[1,2-c]quinazolin-5-yl)-1,3-oxazole-5-carboxamide

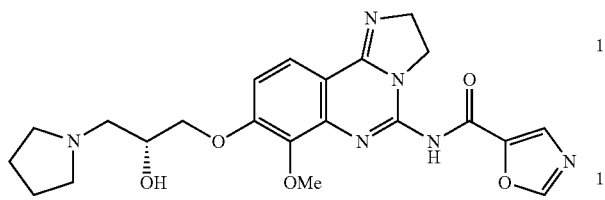

Prepared using 1,3-oxazole-5-carboxylic acid in place of nicotinic acid in Step 2 (0.047 g, 37%): $^1$H NMR (DMSO-$d_6$+1 drop TFA-d) δ 1.82-2.05 (m, 4H), 3.04-3.15 (m, 2H), 3.28-3.34 (m, 2H), 3.52-3.63 (m, 2H), 4.00 (s, 3H), 4.16-4.32 (m, 5H), 4.39-4.49 (m, 2H), 7.45 (d, J=9.2 Hz, 1H), 8.00 (d, J=9.0 Hz, 1H), 8.02 (s, 1H), 8.63 (s, 1H); mass spectrum m/z 454 ((M−1)$^-$, 0.07%), 456 ((M+1)$^+$, 3.2%).

Example 9

Preparation of N-(8-{[(2R)-2-Hydroxy-3-(piperidin-1-yl)propyl]oxy}-7-methoxy-2,3-dihydroimidazo[1,2-c]quinazolin-5-yl)pyridine-3-carboxamide

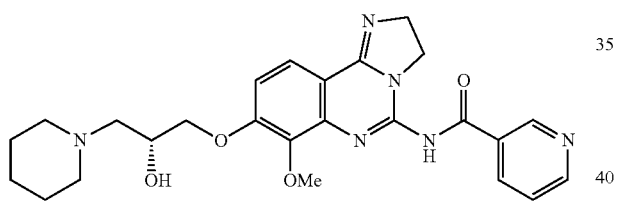

Step 1: Preparation of N-(8-{[(2R)-2-Hydroxy-3-(piperidin-1-yl)propyl]oxy}-7-methoxy-2,3-dihydroimidazo[1,2-c]quinazolin-5-yl)amine

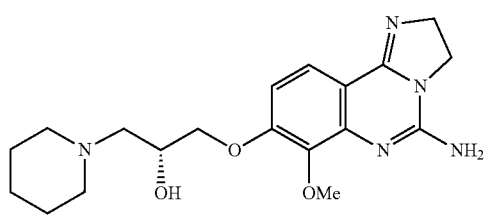 [SMILES: COc1c(OC[C@H](O)CN2CCCCC2)ccc2c1N=C(N)N1CCN=C21]

To a slurry of 5-amino-7-methoxy-2,3-dihydroimidazo[1,2-c]quinazolin-8-ol bis(trifluoroacetate) (Intermediate E, 3.00 g, 6.52 mmol) in DMF (72 mL) was added caesium carbonate (10.62 g, 32.6 mmol, 10.0 equiv.) and the resulting slurry was stirred at room temperature for 1.5 hr, followed by the addition of (R)-glycidyl methanesulfonate (Intermediate F, Step 1, 45 mL, 0.29 M in DMF, 13.0 mmol, 2.0 equiv.). This mixture was stirred at 60° C. for 12 hr and concentrated under reduced pressure to a volume of approximately 50 mL and divided into 3 portions. Each portion was treated with 2.15 mL piperidine (6.45 mL total, 65.2 mmol, 10 equiv.) and was heated in a microwave reactor for 45 min. at 140° C. The combined resulting mixtures were concentrated under reduced pressure. The resulting solids (1.93 g) were purified by MPLC to give N-(8-{[(2R)-2-hydroxy-3-(piperidin-1-yl)propyl]oxy}-7-methoxy-2,3-dihydroimidazo[1,2-c]quinazolin-5-yl)amine (1.93 g, 79%): $^1$H NMR (DMSO-$d_6$+1 drop TFA-d) δ 1.30-1.43 (m, 1H), 1.56-1.70 (m, 2H), 1.70-1.84 (m, 2H), 2.88-3.04 (m, 2H), 3.11-3.32 (m, 2H), 3.42-3.52 (m, 2H), 3.82 (s, 3H), 4.09-4.17 (m, 4H), 4.28-4.38 (m, 3H), 7.24 (d, J=9.4 Hz, 1H), 7.83 (d, J=9.1 Hz, 1H).

Step 2: Preparation of N-(8-{[(2R)-2-hydroxy-3-(piperidin-1-yl)propyl]oxy}-7-methoxy-2,3-dihydroimidazo[1,2-c]quinazolin-5-yl)pyridine-3-carboxamide To a slurry of N-(8-{[(2R)-2-hydroxy-3-(piperidin-1-yl)propyl]oxy}-7-methoxy-2,3-dihydroimidazo[1,2-c]quinazolin-5-yl)amine (0.125 g, 0.34 mmol) and nicotinic acid (0.052 g, 0.42 mmol, 1.3 equiv.) in DMF 3.6 mL) was added PyBOP (0.218 g, 0.42 mmol, 1.3 equiv.) followed by diisopropylethylamine (0.23 mL, 1.34 mmol, 4.0 equiv.). The resulting mixture was stirred at room temperature. After a few hours the mixture turned to a clear solution. The resulting solids were removed by filtration, washed sequentially with DMF, water, then MeOH, and dried at 50° C. under reduced pressure to afford N-(8-{[(2R)-2-hydroxy-3-(piperidin-1-yl)propyl]oxy}-7-methoxy-2,3-dihydroimidazo[1,2-c]quinazolin-5-yl)pyridine-3-carboxamide (0.11 g, 66%): HPLC ret. time 1.00 min.; $^1$H NMR (DMSO-$d_6$+1 drop TFA-d) δ 1.30.1.44 m, 1H), 1.58-1.71 (m, 2H), 1.72-1.85 (m, 3H), 2.89-3.56 (m, 2H), 3.18 (dd, J=10.1, 13.1 Hz, 1H), 3.25-3.31 (m, 1H), 3.45-3.52 (m, 2H), 4.03 (s, 3H), 4.20-4.29 (m, 4H), 4.38-4.49 (m, 1H), 4.53-4.60 (m, 2H), 7.48 (d, J=9.4 Hz, 1H), 7.85 (dd, J=5.3, 7.9 Hz, 1H), 8.04 (d, J=9.1 Hz, 1H), 8.82 (br d, J=8.1 Hz, 1H), 8.93 (dd, J=1.5, 5.3 Hz, 1H), 9.47 (d, J=1.5 Hz, 1H); mass spectrum m/z 479 ((M+1)$^+$, 0.4%).

The following examples were prepared in a manner analogous to Example 9:

Example 14

N-(8-{[(2R)-2-Hydroxy-3-(morpholin-4-yl)propyl]oxy}-7-methoxy-2,3-dihydroimidazo[1,2-c]quinazolin-5-yl)-2-methylpyridine-3-carboxamide

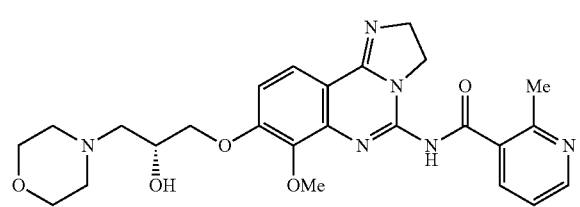 [SMILES: COc1c(OC[C@H](O)CN2CCOCC2)ccc2c1N=C(NC(=O)c1cccnc1C)N1CCN=C21]

Prepared using morpholine in place of piperidine in Step 1, and 2-methyl-3-pyridinecarboxylic acid in place of nicotinic acid in Step 2 (12.1 g, 39%): HPLC ret. time 0.91 min.; $^1$H NMR (DMSO-$d_6$+1 drop TFA-d) δ 2.99 (s, 3H), 3.09-3.40 (m, 4H), 3.48 (br d, J=12.1 Hz, 2H), 3.63-3.83 (m, 2H), 3.89-4.01 (m, 2H), 4.02 (s, 3H), 4.18-4.29 (m, 4H), 4.38-

4.46 (m, 1H), 4.46-4.55 (m, 2H), 7.50 (d, J=9.0 Hz, 1H), 7.96 (dd, J=6.2, 7.5 Hz, 1H), 8.05 (d, J=9.0 Hz, 1H), 8.91 (d, J=5.5 Hz, 1H), 9.06 (br d, J=8.3 Hz, 1H); mass spectrum m/z 493 ((M−1)⁻, 100%), 495 ((M+1)⁺, 4.6%).

Example 15

N-(8-{[(2S)-2-Hydroxy-3-(morpholin-4-yl)propyl]oxy}-7-methoxy-2,3-dihydroimidazo[1,2-c]quinazolin-5-yl)-2-methylpyridine-3-carboxamide

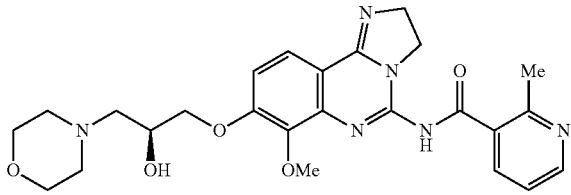 [SMILES: COc1c(OC[C@@H](O)CN2CCOCC2)ccc2c1N=C(NC(=O)c1cccnc1C)N1CCN=C21]

Prepared using (S)-glycidyl methanesulfonate (Intermediate H, Step 1) in place of (R)-glycidyl methanesulfonate (Intermediate F, Step 1), and morpholine in place of piperidine in Step 1, and 2-methyl-3-pyridinecarboxylic acid in place of nicotinic acid in Step 2 (0.059 g, 56%): TLC (9:1 CH₂Cl₂/MeOH+1% NH₄OH in MeOH) R_f 0.44; HPLC ret. time 0.81 min.; ¹H NMR (DMSO-d₆+1 drop TFA-d) δ 2.99 (s, 3H), 3.09-3.40 (m, 4H), 3.48 (br d, J=12.1 Hz, 2H), 3.63-3.83 (m, 2H), 3.89-4.01 (m, 2H), 4.02 (s, 3H), 4.18-4.29 (m, 4H), 4.38-4.46 (m, 1H), 4.46-4.55 (m, 2H), 7.50 (d, J=9.0 Hz, 1H), 7.96 (dd, J=6.2, 7.5 Hz, 1H), 8.05 (d, J=9.0 Hz, 1H), 8.91 (d, J=5.5 Hz, 1H), 9.06 (br d, J=8.3 Hz, 1H); mass spectrum m/z 495 ((M+1)⁺, 2.3%).

Example 19

N-(8-{[(2R)-2-Hydroxy-3-(piperidin-1-yl)propyl]oxy}-7-methoxy-2,3-dihydroimidazo[1,2-c]quinazolin-5-yl)-2-methylpyridine-3-carboxamide

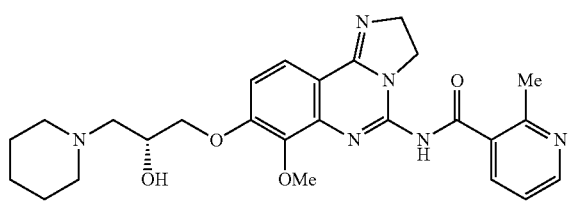 [SMILES: COc1c(OC[C@H](O)CN2CCCCC2)ccc2c1N=C(NC(=O)c1cccnc1C)N1CCN=C21]

Prepared using 2-methyl-3-pyridinecarboxylic acid in place of nicotinic acid in Step 2 (0.059 g, 56%): TLC (9:1 CH₂Cl₂/MeOH+1% NH₄OH in MeOH) R_f 0.45; ¹H NMR (DMSO-d₆+1 drop TFA-d) δ 1.32-1.44 (m, 1H), 1.61-1.71 (m, 2H), 1.72-1.85 (m, 3H), 2.90-3.05 (m, 2H), 2.99 (s, 3H), 3.17 (dd, J=10.1, 13.1 Hz, 1H), 3.28 (dd, J=2.5, 13.1 HZ, 1H), 3.44-3.52 (m, 2H), 4.02 (s, 3H), 4.20-4.28 (m, 4H), 4.38-4.44 (m, 1H), 4.46-4.54 (m, 2H), 7.50 (d, J=9.4 Hz, 1H), 7.96 (dd, J=6.1, 7.3 Hz, 1H), 8.05, (d, J=9.1 Hz, 1H), 8.91 (dd, J=1.5, 5.8 Hz, 1H), 9.06, br s, 1H); mass spectrum m/z 493 ((M+1)⁺, 4.0%).

Example 22

6-Amino-N-(8-{[(2S)-2-hydroxy-3-(morpholin-4-yl)propyl]oxy}-7-methoxy-2,3-dihydroimidazo[1,2-c]quinazolin-5-yl)pyridine-3-carboxamide

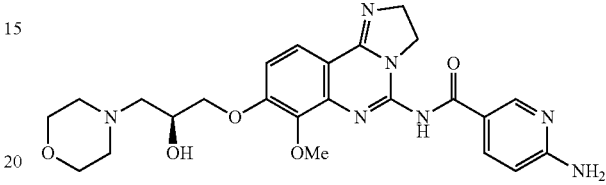

Prepared using (S)-glycidyl methanesulfonate (Intermediate H, Step 1) in place of (R)-glycidyl methanesulfonate (Intermediate F, Step 1) in Step 1, and 6-amino-3-pyridinecarboxylic acid in place of nicotinic acid in Step 2 (37.0 mg, 35%): HPLC ret. time 0.82 min.; ¹H NMR (DMSO-d₆+1 drop TFA-d) δ 3.13-3.40 (m, 4H), 3.43-3.53 (m, 2H), 3.64-3.83 (m, 2H), 3.89-3.98 (m, 2H), 4.01 (s, 3H), 4.18-4.28 (m, 4H), 4.37-4.45 (m, 1H), 4.45-4.54 (m, 2H), 7.03 (d, J=9.4 Hz, 1H), 7.46 (d, J=9.4 Hz, 1H), 8.02 (d, J=9.0 Hz, 1H), 8.45 (dd, J=2.1, 9.2 HZ, 1H), 8.75 (d, J=1.7 Hz, 1H); mass spectrum m/z 495 ((M+1)⁺, 8.7%).

Example 23

6-Amino-N-(8-{[(2R)-2-hydroxy-3-(morpholin-4-yl)propyl]oxy}-7-methoxy-2,3-dihydroimidazo[1,2-c]quinazolin-5-yl)-2-methylpyridine-3-carboxamide

Prepared using morpholine in place of piperidine in Step 1, and 6-amino-2-methyl-3-pyridinecarboxylic acid in place of nicotinic acid in Step 2 (60.0 mg, 69%): HPLC ret. time 0.83 min.; ¹H NMR (DMSO-d₆+1 drop TFA-d) δ 2.81 (s, 3H), 3.11-3.39 (m, 4H), 3.43-3.51 (m, 2H), 3.63-3.82 (m, 2H), 3.89-3.98 (m, 2H), 4.00 (s, 3H), 4.16-4.27 (m, 4H), 4.38-4.50 (m, 3H), 6.86 (d, J=9.4 Hz, 1H), 7.46 (d, J=9.2 Hz, 1H), 8.02 (d, J=9.2 Hz, 1H), 8.57 (d, J=9.4 Hz, 1H); mass spectrum m/z 510 ((M+1)⁺, 4.4%).

Example 25

2-Amino-N-{8-[2-hydroxy-3-(morpholin-4-yl)propoxy]-7-methoxy-2,3-dihydroimidazo[1,2-c]quinazolin-5-yl}pyrimidine-5-carboxamide

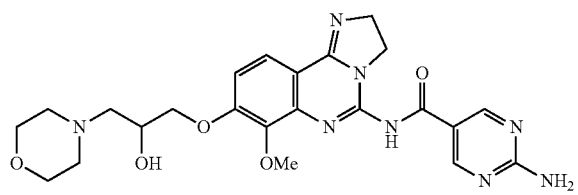 [SMILES: COc1c(OCC(O)CN2CCOCC2)ccc2c1N=C(NC(=O)c1cnc(N)nc1)N1CCN=C21]

Prepared using morpholine in place of piperidine and racemic glycidyl methanesulfonate in place of (R)-glycidyl methanesulfonate in Step 1, and 2-amino-5-pyrimidinecarboxylic acid in place of nicotinic acid in Step 2 (40.0 mg, 46%): HPLC ret. time 0.81 min.; $^1$H NMR (DMSO-$d_6$+1 drop TFA-d) δ 3.15-3.39 (m, 4H), 3.44-3.52 (m, 2H), 3.63-3.83 (m, 2H), 3.89-3.99 (m, 2H), 4.00 (s, 3H), 4.15-4.26 (m, 4H), 4.37-4.45 (m, 1H), 4.45-4.54 (m, 2H), 7.44 (d, J=9.2 Hz, 1H), 8.00 (d, J=9.2 Hz, 1H), 8.99 (s, 2H); mass spectrum m/z 497 ((M+1)$^+$, 11%).

Example 26

2-Amino-N-(8-{[(2S)-2-hydroxy-3-(morpholin-4-yl)propyl]oxy}-7-methoxy-2,3-dihydroimidazo[1,2-c]quinazolin-5-yl)pyrimidine-5-carboxamide

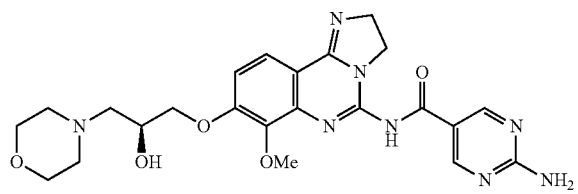 [SMILES: COc1c(OC[C@@H](O)CN2CCOCC2)ccc2c1N=C(NC(=O)c1cnc(N)nc1)N1CCN=C21]

Prepared using (S)-glycidyl methanesulfonate (Intermediate H, Step 1) in place of (R)-glycidyl methanesulfonate (Intermediate F, Step 1), and morpholine in place of piperidine in Step 1, and 2-amino-5-pyrimidinecarboxylic acid in place of nicotinic acid in Step 2 (75.0 mg, 71%): HPLC ret. time 0.81 min.; $^1$H NMR (DMSO-$d_6$+1 drop TFA-d) δ 3.14-3.38 (m, 4H), 3.44-3.52 (m, 2H), 3.69 (app t, J=12.0 Hz, 1H), 3.77/app t, J=12.1 Hz, 1H), 3.90-3.98 (m, 2H), 4.00 (s, 3H), 4.16-4.25 (m, 4H), 4.38-4.44 (m, 1H), 4.46-4.52 (m, 2H), 7.43 (d, J=9.1 Hz, 1H), 7.99 (d, J=9.1 Hz, 1H), 8.97 (s, 2H); mass spectrum m/z 497 ((M+1)$^+$, 8.8%).

Example 30

N-(8-{[(2R)-2-Hydroxy-3-(morpholin-4-yl)propyl]oxy}-7-methoxy-2,3-dihydroimidazo[1,2-c]quinazolin-5-yl)-3H-imidazo[4,5-b]pyridine-6-carboxamide

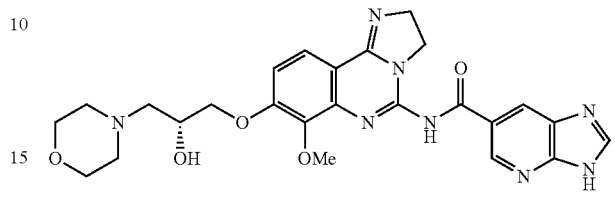

Prepared using morpholine in place of piperidine in Step 1, and 3H-imidazo[4,5-b]pyridine-6-carboxylic acid in place of nicotinic acid in Step 2 (0.18 g, 60%): HPLC ret. time 0.75 min.; $^1$H NMR (DMSO-$d_6$+1 drop TFA-d) δ 3.15-3.39 (m, 4H), 3.45-3.51 (m, 2H), 3.65-3.82 (m, 2H), 3.91-4.02 (m, 3H), 4.04 (s, 3H), 4.21-4.28 (m, 4H), 4.39-4.46 (m, 1H), 4.56-4.63 (m, 2H) 6.86 (d, J=9.4 Hz, 1H), 7.47 (d, J=9.4 Hz, 1H), 8.03 (d, J=9.1 Hz, 1H), 8.89 (br s, 1H), 9.22 (s, 1H), 9.38 (s, 1H); mass spectrum m/z 521 ((M+1)$^+$, 2.7%).

Example 31

N-{8-[2-Hydroxy-3-(morpholin-4-yl)propoxy]-7-methoxy-2,3-dihydroimidazo[1,2-c]quinazolin-5-yl}-1,3-thiazole-5-carboxamide

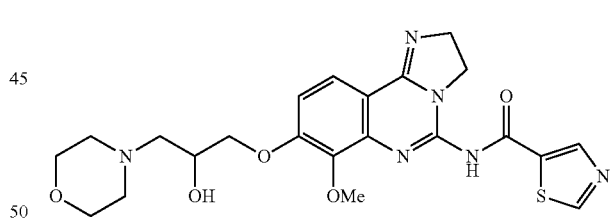

Prepared using morpholine in place of piperidine and racemic glycidyl methane sulfonate in place of (R)-glycidyl methanesulfonate in Step 1, and 1,3-thiazole-5-carboxylic acid in place of nicotinic acid in Step 2 (23.0 mg, 27%): TLC (9:1 CH$_2$Cl$_2$/MeOH+1% NH$_4$OH in MeOH) R$_f$ 0.48; HPLC ret. time 0.78 min.; $^1$H NMR (DMSO-$d_6$+1 drop TFA-d) δ 3.17-3.42 (m, 4H), 3.49-3.54 (m, 2H), 3.74 (app t, J=11.8 Hz, 1H), 3.82 (app t, J=11.6 Hz, 1H) 3.95-4.05 (m, 2H), 4.06 (s, 3H), 4.23-4.31 (m, 4H), 4.43-4.53 (m, 3H), 7.50 (d, J=9.1 Hz, 1H), 8.05 (d, J=9.1 Hz, 1H), 8.65 (s, 1H), 9.36 (s, 1H); mass spectrum m/z 487 ((M+1)$^+$, 6.6%).

Example 32

N-(8-{[(2R)-2-Hydroxy-3-(morpholin-4-yl)propyl]oxy}-7-methoxy-2,3-dihydroimidazo[1,2-c]quinazolin-5-yl)-1,3-thiazole-5-carboxamide

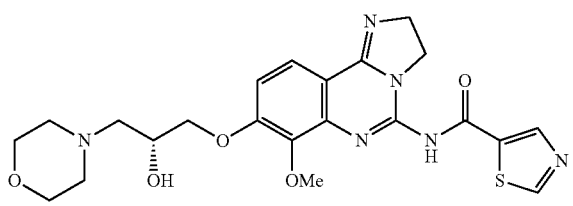 [SMILES: COc1c(OC[C@H](O)CN2CCOCC2)ccc2c1N=C(NC(=O)c1cncs1)N1CCN=C21]

Prepared using morpholine in place of piperidine in Step 1, and 1,3-thiazole-5-carboxylic acid in place of nicotinic acid in Step 2 (0.18 g, 60%): HPLC ret. time 0.88 min.; $^1$H NMR (DMSO-$d_6$+1 drop TFA-d) δ 3.17-3.42 (m, 4H), 3.49-3.54 (m, 2H), 3.74 (app t, J=11.8 Hz, 1H), 3.82 (app t, J=11.6 Hz, 1H), 3.95-4.05 (m, 2H), 4.06 (s, 3H), 4.23-4.31 (m, 4H), 4.43-4.53 (m, 3H), 7.50 (d, J=9.1 Hz, 1H), 8.05 (d, J=9.1 Hz, 1H), 8.65 (s, 1H), 9.36 (s, 1H); mass spectrum m/z 487 ((M+1)$^+$, 6.8%).

Example 33

N-(8-{[(2S)-2-Hydroxy-3-(morpholin-4-yl)propyl]oxy}-7-methoxy-2,3-dihydroimidazo[1,2-c]quinazolin-5-yl)-1,3-thiazole-5-carboxamide

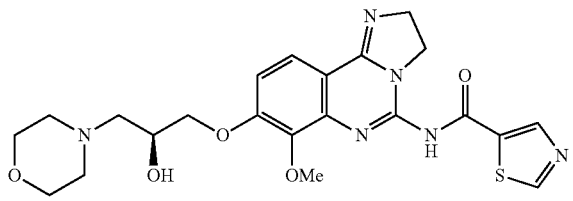 [SMILES: COc1c(OC[C@@H](O)CN2CCOCC2)ccc2c1N=C(NC(=O)c1cncs1)N1CCN=C21]

Prepared using (S)-glycidyl methanesulfonate (Intermediate H, Step 1) in place of (R)-glycidyl methanesulfonate (Intermediate F, Step 1), and morpholine in place of piperidine in Step 1, and 1,3-thiazole-5-carboxylic acid in place of nicotinic acid in Step 2 (42.0 mg, 41%): TLC (9:1 CH$_2$Cl$_2$/MeOH+1% NH$_4$OH in MeOH) R$_f$ 0.43; HPLC ret. time 0.81 min.; $^1$H NMR (DMSO-$d_6$+1 drop TFA-d) δ 3.11-3.0 (m, 4H), 3.43-3.52 (m, 2H), 3.69 (app t, J=11.8 Hz, 1H), 3.78 (app t, J=11.6 Hz, 1H) 3.88-4.00 (m, 2H), 4.01 (s, 3H), 4.16-4.27 (m, 4H), 4.37-4.51 (m, 3H), 7.45 (d, J=9.1 Hz, 1H), 8.01 (d, J=9.1 Hz, 1H), 8.60 (s, 1H), 9.31 (s, 1H); mass spectrum m/z 487 ((M+1)$^+$, 4.6%).

Example 37

N-(8-{[(2R)-2-Hydroxy-3-(piperidin-1-yl)propyl]oxy}-7-methoxy-2,3-dihydroimidazo[1,2-c]quinazolin-5-yl)-1,3-thiazole-5-carboxamide

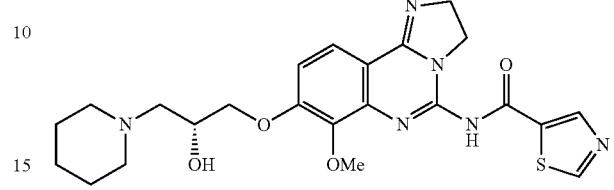

Prepared using 1,3-thiazole-5-carboxylic acid in place of nicotinic acid in Step 2 (0.18 g, 60%): HPLC ret. time 1.10 min.; $^1$H NMR (DMSO-$d_6$+1 drop TFA-d) δ 1.30-1.45 (m, 1H), 1.60-1.86 (m, 5H), 2.87-3.06 (m, 2H), 3.12-3.31 (m, 2H), 3.43-3.54 (m, 2H), 4.01 (s, 3H), 4.16-4.27 (m, 4H), 4.35-4.50 (m, 3H), 7.45 (d, J=9.2 Hz, 1H), 8.00 (d, J=9.2 Hz, 1H), 8.61 (s, 1H), 9.31 (s, 1H); mass spectrum m/z 485 ((M+1)$^+$, 4.1%).

Example 39

2-Amino-N-(8-{[(2R)-2-hydroxy-3-(morpholin-4-yl)propyl]oxy}-7-methoxy-2,3-dihydroimidazo[1,2-c]quinazolin-5-yl)-4-methyl-1,3-thiazole-5-carboxamide

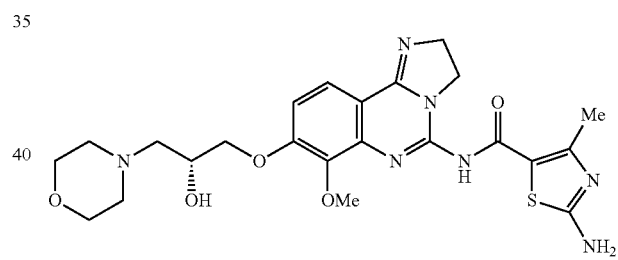

Prepared using morpholine in place of piperidine in Step 1, and 2-amino-4-methyl-1,3-thiazole-5-carboxylic acid in place of nicotinic acid in Step 2 (0.18 g, 60%): HPLC ret. time 0.83 min.; $^1$H NMR (DMSO-$d_6$+1 drop TFA-d) δ 2.57 (s, 3H), 3.11-3.38 (m, 4H), 3.44-3.51 (m, 2H), 3.69 (app t, J=11.9 Hz, 1H), 3.77 (app t, J=11.5 Hz, 1H), 3.90-3.98 (m, 2H), 3.99 (s, 3H), 4.16-4.26 (m, 4H), 4.32-4.44 (m, 3H), 7.44 (d, J=9.1 Hz, 1H), 8.00 (s, 1H); mass spectrum m/z 516 ((M+1)$^+$, 3.0%).

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellu lose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCL_2F_2$, $F_2ClC$—$CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellu lose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, Lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known anti-hyper-proliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, topoisomerase inhibitors, biological response modifiers, or anti-hormones.

The additional pharmaceutical agent can be aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BAY 80-6946, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulfate, letrozole, Leucovorin, Leuprolide, leuprolide acetate, Levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, oxapred, oxaliplatin, paclitaxel, pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, RDEA 119, rebif, rhenium-186 etidronate, rituximab, rofeon-A, romurtide, salagen, sandostatin, sargramostim, semustine, sizofiran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, sorafenib, avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, Lanreotide, lasofoxifene, libra, Lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or combinations thereof.

In an embodiment of the present invention, a compound of general formula (I) as defined herein can optionally be administered in combination with one or more of the following: 1311-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, 1-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, Lanreotide, lapatinib, lenalidomide, lenograstim, lentinan, letrozole, Leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

Optional anti-hyper-proliferative agents which can be added to the composition include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of the invention include but are not limited to other anti-cancer agents such as epothilone and its derivatives, irinotecan, raloxifen and topotecan.

The compounds of the invention may also be administered in combination with protein therapeutics. Such protein therapeutics suitable for the treatment of cancer or other angiogenic disorders and for use with the compositions of the invention include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, Labetuzumab, alpha-particle-emitting radioisotope-llinked lintuzumab, EM-1421, HyperAcute vaccine, tucotuzumab celmoleukin, galiximab, HPV-16-E7, Javelin—prostate cancer, Javelin—melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 1311-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

A compound of general formula (I) as defined herein can optionally be administered in combination with one or more of the following: ARRY-162, ARRY-300, ARRY-704, AS-703026, AZD-5363, AZD-8055, BEZ-235, BGT-226, BKM-120, BYL-719, CAL-101, CC-223, CH-5132799, deforolimus, E-6201, enzastaurin, GDC-0032, GDC-0068, GDC-0623, GDC-0941, GDC-0973, GDC-0980, GSK-2110183, GSK-2126458, GSK-2141795, MK-2206, novolimus, OSI-027, perifosine, PF-04691502, PF-05212384, PX-866, rapamycin, RG-7167, RO-4987655, RO-5126766, selumetinib, TAK-733, trametinib, triciribine, UCN-01, WX-554, XL-147, XL-765, zotarolimus, ZSTK-474

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(7) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in VIVO.

As mentioned supra, the compounds of the present invention have surprisingly been found to effectively inhibit allo-MEK and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by allo-MEK, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula (I) described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mps-1, such as, for example, haematological tumours, solid tumours, and/or metastases thereof, e.g. Leukaemias and myelodysplastic syndrome, malignant Lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's Lymphoma, cutaneous T-cell Lymphoma, Burkitt Lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Evaluation

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al., 1993) taxotere (Bissery et al., 1995), and topoisomerase inhibitors (Edelman & Gandara, 1996) were demonstrated with the use of in vitro tumor proliferation assays.

Demonstration of the activity of the compounds of the present invention may be accomplished through in vitro, ex vivo, and in vivo assays that are well known in the art. For example, to demonstrate the activity of the compounds of the present invention, the following assays may be used.

Biological Assays

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

Determination of % Inhibition and $IC_{50}$ Values of Compounds in PI3Kα kinase assay PI3Kα inhibitory activity of compounds of the present invention was quantified employing the HTRF-based PI3K inhibition assay as described below.

Chemicals and Assay Materials

As reagents for the kinase reaction itself and the quantification of the reaction product, the PI3-Kinase HTRF Assay kit from Millipore (#33-017) was used. With this kit the phosphatidylinositol 3,4,5-trisphosphate ($PIP_3$) generated in the kinase reaction is detected by displacement of a biotinylated ligand from an energy transfer complex consisting of a Europium-labeled anti-GST monoclonal antibody, a GST-tagged PH domain, biotinylated $PIP_3$ and Streptavidin-Allophycocyanin (APC). As kinase a complex of N-terminal His6-tagged recombinant full-length human p110α and untagged, recombinant, full length, human p85α, coexpressed by baculovirus infected Sf21 insect cells and purified using $Ni^{2+}$/NTA-agarose, was used (Millipore product #14-602).

For the assay 50 nL of a 80-fold concentrated solution of the test compound in DMSO was pipetted into a black low volume 384-well microtiter plate (Greiner Bio-One, Frickenhausen, Germany), 3 μL of a solution of PI3Kα and phosphatidylinositol-4,5-bisphosphate ($PIP_2$, 13.8 μM=>final conc. in 4 μl reaction volume=10 μM) in 1× reaction buffer (exact composition not disclosed by the vendor) were added and the mixture was incubated for 15 min at 22° C. to allow pre-binding of the test compounds to the enzyme before the start of the kinase reaction. The amount of PI3Kα was chosen to have the enzyme reaction in the linear range and depended on the activity of the individual lot, typical concentrations in assay were in the range of 90 ng/mL. Then the kinase reaction was started by the addition of 1 μL of a solution of adenosine triphosphate (ATP, 40 μM=>final conc. in the 4 μL assay volume is 10 μM) in reaction buffer and the resulting mixture was incubated for a reaction time of 20 min at 22° C.

The reaction was stopped by the addition of 1 μL of an stop solution (containing the biotinylated $PIP_3$ used as a tracer), then 1 μL detection mix (containing a Europium-labeled anti-GST monoclonal antibody, a GST-tagged PH domain, and Streptavidin-Allophycocyanin) was added and resulting mixture was incubated 3 h at 22° C. to allow the formation of complexes between the detection reagents and either the $PIP_3$ generated in the kinase reaction, or the biotinylated $PIP_3$ added with the stop solution. Subsequently, the amount of energy transfer complex consisting of a Europium-labeled anti-GST monoclonal antibody, a GST-tagged PH domain, biotinylated $PIP_3$ and Streptavidin-Allophycocyanin (APC) was evaluated by measurement of the resonance energy transfer from the Europium-labeled anti-GST monoclonal antibody to the Streptavidin-Allophycocyanin. Therefore, the fluorescence emissions at 620 nm and 665 nm after excitation at 350 nm were measured using a TR-FRET reader, e.g., a Pherastar (BMG Labtechnologies, Offenburg, Germany) or a Viewlux (Perkin-Elmer). The ratio of the emissions at 665 nm and at 622 nm was taken as the measure for the amount of biotinylated $PIP_3$ bound to the GST-tagged PH domain, which is negatively correlated with the amount of $PIP_3$ generated. The data were normalized (enzyme reaction without inhibitor=0% inhibition; all other assay components in the absence of enzyme=100% inhibition). Normally test compounds were tested on the same microtiter plate at 10 different concentrations in the range of 25 μM to 1.3 nM (25 μM, 8.3 μM, 2.8 μM, 0.93 μM, 0.31 μM, 103 nM, 34 nM, 11 nM, 3.8 nM and 1.3 nM, a dilution series prepared before the assay at the level of the 80-fold conc. stock solutions by serial 1:3 dilutions) in duplicate values for each concentration and $IC_{50}$ values were calculated by a 4-parameter fit using in-house software.

The following example compounds displayed an average $IC_{50}$ in the PI3K alpha biochemical assay of less than 10 nanomolar: 1, 5, 6, 8, 9, 10, 12, 14, 17, 18, 19, 20, 21, 23, 25, 27, 28, 29, 30, 32, 34, 35, 36, 37, 38, 39, 41. The following example compounds displayed an average $IC_{50}$ in the PI3K alpha biochemical assay of between 10 and 50 nanomolar: 2, 3, 4, 7, 11, 16, 24. The following example compound displayed an average $IC_{50}$ in the PI3K alpha biochemical assay of greater than 50 nanomolar: 40. Percent inhibition values obtained for example compounds at a 0.93 μM concentration are given in Table 1.

Determination of % Inhibition and $IC_{50}$ Values of Compounds in PI3Kβ Kinase Assay PI3Kβ inhibitory activity of compounds of the present invention was quantified employing the HTRF based PI3K inhibition assay as described below.

Chemicals and Assay Materials

As reagents for the kinase reaction itself and the quantification of the reaction product, the PI3-Kinase HTRF Assay kit from Millipore (#33-017) was used. With this kit the phosphatidylinositol 3,4,5-trisphosphate ($PIP_3$) generated in the kinase reaction is detected by displacement of a biotinylated ligand from an energy transfer complex consisting of a Europium-labeled anti-GST monoclonal antibody, a GST-tagged PH domain, biotinylated $PIP_3$ and Streptavidin-Allophycocyanin (APC). As kinase a complex of N-terminal His6-tagged recombinant full-length human p110 βand untagged, recombinant, full length, human p85α, coexpressed by baculovirus infected Sf21 insect cells and purified using $Ni^{2+}$/NTA-agarose, was used (Millipore product #14-603).

For the assay 50 nL of a 80-fold concentrated solution of the test compound in DMSO was pipetted into a black low volume 384-well microtiter plate (Greiner Bio-One, Frickenhausen, Germany), 3 μl of a solution of PI3Kβ and phosphatidylinositol-4,5-bisphosphate ($PIP_2$, 13.8 μM=>final conc. in 4 μl reaction volume=10 μM) in 1× reaction buffer (exact composition not disclosed by the vendor) were added and the mixture was incubated for 15 min at 22° C. to allow pre-binding of the test compounds to the enzyme before the start of the kinase reaction. The amount of PI3Kβ was chosen to have the enzyme reaction in the linear range and depended on the activity of the individual lot, typical concentrations in assay were in the range of 120 ng/mL. Then the kinase reaction was started by the addition of 1 μL of a solution of adenosine triphosphate (ATP, 40 μM=>final conc. in the 4 μl assay volume is 10 μM) in reaction buffer and the resulting mixture was incubated for a reaction time of 20 min at 22° C.

The reaction was stopped by the addition of 1 μL of an stop solution (containing the biotinylated $PIP_3$ used as a tracer). Then 1 μL detection mix (containing a Europium-labeled anti-GST monoclonal antibody, a GST-tagged PH domain, and Streptavidin-Allophycocyanin) was added and resulting mixture was incubated for 3 h at 22° C. to allow the formation of complexes between the detection reagents and either the $PIP_3$ generated in the kinase reaction, or the biotinylated $PIP_3$ added with the stop solution. Subsequently the amount of energy transfer complex consisting of a Europium-labeled anti-GST monoclonal antibody, a GST-tagged PH domain, biotinylated $PIP_3$ and Streptavidin-Allophycocyanin (APC) was evaluated by measurement of the resonance energy transfer from the Europium-labeled anti-GST monoclonal antibody to the Streptavidin-Allophycocyanin. Therefore, the fluorescence emissions at 620 nm and 665 nm after excitation at 350 nm were measured using a TR-FRET reader, e.g., a Pherastar (BMG Labtechnologies, Offenburg, Germany) or a Viewlux (Perkin-Elmer). The ratio of the emissions at 665 nm and at 622 nm were taken as the measure for the amount of biotinylated $PIP_3$ bound to the GST-tagged PH domain, which is negatively correlated with the amount of $PIP_3$ generated. The data were normalized (enzyme reaction without inhibitor=0% inhibition, all other assay components in the absence of enzyme=100% inhibition). Normally, test compounds were tested on the same microtiter plate at 10 different concentrations in the range of 25 μM to 1.3 nM (25 μM, 8.3 μM, 2.8 μM, 0.93 μM, 0.31 μM, 103 nM, 34 nM, 11 nM, 3.8 nM and 1.3 nM, a dilution series prepared before the assay at the level of the 80-fold conc. stock solutions by serial 1:3 dilutions) in duplicate values for each concentration and $IC_{50}$ values were calculated by a 4 parameter fit using in-house software.

The following example compounds displayed an average $IC_{50}$ in the PI3K beta biochemical assay of less than 10 nanomolar: 25, 28, 29, 38 and 39. The following example compounds displayed an average $IC_{50}$ in the PI3K beta biochemical assay of between 10 and 50 nanomolar: 2, 5, 8, 9, 10, 11, 12, 14, 16, 17, 18, 19, 20, 21, 23, 24, 27, 30, 32, 34, 35, 36, 37 and 41. The following example compounds displayed an average IC$_{50}$ in the PI3K beta biochemical assay of greater than 50 nanomolar: 1, 3, 4, 6, 7, and 40. Percent inhibition values obtained for example compounds at a 0.93 μM concentration are given in Table 1.

TABLE 1

| Example No | PI3K alpha average % Inhibition at 0.93 μM | PI3K beta average % Inhibition at 0.93 μM | PI3K beta average IC$_{50}$/ PI3K alpha average IC$_{50}$ | IUPAC Name |
|---|---|---|---|---|
| Comparative Example 1 | 97.4 | 92.1 | 9.92 | N-{8-[2-hydroxy-3-(morpholin-4-yl)propoxy]-7-methoxy-2,3-dihydroimidazo[1,2-c]quinazolin-5-yl}pyridine-3-carboxamide |
| 2 | 97.6 | 94.4 | 2.98 | N-(8-{[(2R)-2-hydroxy-3-(morpholin-4-yl)propyl]oxy}-7-methoxy-2,3-dihydroimidazo[1,2-c]quinazolin-5-yl)pyridine-3-carboxamide |
| 3 | 103.4 | 92.9 | 6.20 | N-(8-{[(2S)-2-hydroxy-3-(morpholin-4-yl)propyl]oxy}-7-methoxy-2,3-dihydroimidazo[1,2-c]quinazolin-5-yl)pyridine-3-carboxamide |
| 4 | 99.8 | 96.4 | 4.85 | N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]pyridine-3-carboxamide |
| 5 | 100.9 | 104.0 | 3.68 | N-(8-{[(2R)-2-hydroxy-3-(8-oxa-3-azabicyclo[3.2.1]oct-3-yl)propyl]oxy}-7-methoxy-2,3-dihydroimidazo[1,2-c]quinazolin-5-yl)pyridine-3-carboxamide |
| 6 | 91.2 | 84.1 | 9.96 | N-{8-[2-hydroxy-3-(thiomorpholin-4-yl)propoxy]-7-methoxy-2,3-dihydroimidazo[1,2-c]quinazolin-5-yl}pyridine-3-carboxamide |
| 7 | 99.5 | 97.3 | 2.22 | N-(8-{[(2R)-3-(azetidin-1-yl)-2-hydroxypropyl]oxy}-7-methoxy-2,3-dihydroimidazo[1,2-c]quinazolin-5-yl)pyridine-3-carboxamide |
| 8 | 102.0 | 100.8 | 2.62 | N-(8-{[(2R)-2-hydroxy-3-(pyrrolidin-1-yl)propyl]oxy}-7-methoxy-2,3-dihydroimidazo[1,2-c]quinazolin-5-yl)pyridine-3-carboxamide |
| 9 | 103.5 | 97.2 | 2.02 | N-(8-{[(2R)-2-hydroxy-3-(piperidin-1-yl)propyl]oxy}-7-methoxy-2,3-dihydroimidazo[1,2-c]quinazolin-5-yl)pyridine-3-carboxamide |
| 10 | 96.3 | 98.1 | 5.47 | N-{8-[3-(dimethylamino)-2-hydroxypropoxy]-7-methoxy-2,3-dihydroimidazo[1,2-c]quinazolin-5-yl}pyridine-3-carboxamide |
| 11 | 82.0 | 95.5 | 1.60 | N-(8-{[(2R)-3-(dimethylamino)-2-hydroxypropyl]oxy}-7-methoxy-2,3-dihydroimidazo[1,2-c]quinazolin-5-yl)pyridine-3-carboxamide |
| 12 | 104.0 | 114.6 | 4.74 | N-(8-{[(2R)-3-(dipropan-2-ylamino)-2-hydroxypropyl]oxy}-7-methoxy-2,3-dihydroimidazo[1,2-c]quinazolin-5-yl)pyridine-3-carboxamide |
| 13 | | | | N-{8-[2-hydroxy-3-(morpholin-4-yl)propoxy]-7-methoxy-2,3-dihydroimidazo[1,2-c]quinazolin-5-yl}-2-methylpyridine-3-carboxamide |
| 14 | 103.8 | 101.6 | 3.09 | N-(8-{[(2R)-2-hydroxy-3-(morpholin-4-yl)propyl]oxy}-7-methoxy-2,3-dihydroimidazo[1,2-c]quinazolin-5-yl)-2-methylpyridine-3-carboxamide |
| 15 | | | | N-(8-{[(2S)-2-hydroxy-3-(morpholin-4-yl)propyl]oxy}-7-methoxy-2,3-dihydroimidazo[1,2-c]quinazolin-5-yl)-2-methylpyridine-3-carboxamide |
| 16 | 108.7 | 87.7 | 3.94 | N-(8-{[(2R)-3-(azetidin-1-yl)-2-hydroxypropyl]oxy}-7-methoxy-2,3-dihydroimidazo[1,2-c]quinazolin-5-yl)-2-methylpyridine-3-carboxamide |
| 17 | 108.9 | 87.2 | 5.36 | N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]-2-methylpyridine-3-carboxamide |
| 18 | 96.9 | 103.0 | 3.90 | N-(8-{[(2R)-2-hydroxy-3-(pyrrolidin-1-yl)propyl]oxy}-7-methoxy-2,3-dihydroimidazo[1,2-c]quinazolin-5-yl)-2-methylpyridine-3-carboxamide |
| 19 | 102.6 | 91.2 | 2.78 | N-(8-{[(2R)-2-hydroxy-3-(piperidin-1-yl)propyl]oxy}-7-methoxy-2,3-dihydroimidazo[1,2-c]quinazolin-5-yl)-2-methylpyridine-3-carboxamide |
| 20 | 102.4 | 98.6 | 4.20 | N-(8-{[(2R)-3-(dipropan-2-ylamino)-2-hydroxypropyl]oxy}-7-methoxy-2,3-dihydroimidazo[1,2-c]quinazolin-5-yl)-2-methylpyridine-3-carboxamide |
| 21 | | | 9.37 | 6-amino-N-{8-[2-hydroxy-3-(morpholin-4-yl)propoxy]-7-methoxy-2,3-dihydroimidazo[1,2-c]quinazolin-5-yl}pyridine-3-carboxamide |
| 22 | | | | 6-amino-N-(8-{[(2S)-2-hydroxy-3-(morpholin-4-yl)propyl]oxy}-7-methoxy-2,3-dihydroimidazo[1,2-c]quinazolin-5-yl)pyridine-3-carboxamide |

TABLE 1-continued

| Example No | PI3K alpha average % Inhibition at 0.93 μM | PI3K beta average % Inhibition at 0.93 μM | PI3K beta average IC$_{50}$/ PI3K alpha average IC$_{50}$ | IUPAC Name |
|---|---|---|---|---|
| 23 | 104.7 | 118.6 | 7.30 | 6-amino-N-(8-{[(2R)-2-hydroxy-3-(morpholin-4-yl)propyl]oxy}-7-methoxy-2,3-dihydroimidazo[1,2-c]quinazolin-5-yl)-2-methylpyridine-3-carboxamide |
| 24 | 85.1 | 94.7 | 1.99 | N-(8-{[(2R)-2-hydroxy-3-(pyrrolidin-1-yl)propyl]oxy}-7-methoxy-2,3-dihydroimidazo[1,2-c]quinazolin-5-yl)pyrimidine-5-carboxamide |
| 25 | 92.7 | 93.3 | 8.30 | 2-amino-N-{8-[2-hydroxy-3-(morpholin-4-yl)propoxy]-7-methoxy-2,3-dihydroimidazo[1,2-c]quinazolin-5-yl}pyrimidine-5-carboxamide |
| 26 | | | | 2-amino-N-{8-{[(2S)-2-hydroxy-3-(morpholin-4-yl)propyl]oxy}-7-methoxy-2,3-dihydroimidazo[1,2-c]quinazolin-5-yl)pyrimidine-5-carboxamide |
| 27 | 97.9 | 102.3 | 5.52 | 2-amino-N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]pyrimidine-5-carboxamide |
| 28 | 102.1 | 101.8 | 4.71 | 2-amino-N-(8-{[(2R)-2-hydroxy-3-(8-oxa-3-azabicyclo[3.2.1]oct-3-yl)propyl]oxy}-7-methoxy-2,3-dihydroimidazo[1,2-c]quinazolin-5-yl)pyrimidine-5-carboxamide dihydrochloride |
| 29 | 102.5 | 106.5 | 6.75 | 2-amino-N-(8-{[(2R)-3-(dimethylamino)-2-hydroxypropyl]oxy}-7-methoxy-2,3-dihydroimidazo[1,2-c]quinazolin-5-yl)pyrimidine-5-carboxamide |
| 30 | 110.3 | 107.5 | 8.83 | N-(8-{[(2R)-2-hydroxy-3-(morpholin-4-yl)propyl]oxy}-7-methoxy-2,3-dihydroimidazo[1,2-c]quinazolin-5-yl)-3H-imidazo[4,5-b]pyridine-6-carboxamide |
| 31 | | | | N-{8-[2-hydroxy-3-(morpholin-4-yl)propoxy]-7-methoxy-2,3-dihydroimidazo[1,2-c]quinazolin-5-yl}-1,3-thiazole-5-carboxamide |
| 32 | 96.1 | 95.5 | 5.91 | N-(8-{[(2R)-2-hydroxy-3-(morpholin-4-yl)propyl]oxy}-7-methoxy-2,3-dihydroimidazo[1,2-c]quinazolin-5-yl)-1,3-thiazole-5-carboxamide |
| 33 | | | | N-(8-{[(2S)-2-hydroxy-3-(morpholin-4-yl)propyl]oxy}-7-methoxy-2,3-dihydroimidazo[1,2-c]quinazolin-5-yl)-1,3-thiazole-5-carboxamide |
| 34 | 94.2 | 97.1 | 7.21 | N-[8-({(2R)-3-[(2R,6S)-2,6-dimethylmorpholin-4-yl]-2-hydroxypropyl}oxy)-7-methoxy-2,3-dihydroimidazo[1,2-c]quinazolin-5-yl]-1,3-thiazole-5-carboxamide |
| 35 | 109.3 | 101.6 | 6.30 | N-(8-{[(2R)-3-(azetidin-1-yl)-2-hydroxypropyl]oxy}-7-methoxy-2,3-dihydroimidazo[1,2-c]quinazolin-5-yl)-1,3-thiazole-5-carboxamide |
| 36 | 92.4 | 93.9 | 3.41 | N-(8-{[(2R)-2-hydroxy-3-(pyrrolidin-1-yl)propyl]oxy}-7-methoxy-2,3-dihydroimidazo[1,2-c]quinazolin-5-yl)-1,3-thiazole-5-carboxamide |
| 37 | 103.0 | 93.7 | 2.98 | N-(8-{[(2R)-2-hydroxy-3-(piperidin-1-yl)propyl]oxy}-7-methoxy-2,3-dihydroimidazo[1,2-c]quinazolin-5-yl)-1,3-thiazole-5-carboxamide |
| 38 | 92.8 | 95.1 | 5.64 | N-(8-{[(2R)-2-Hydroxy-3-(pyrrolidin-1-yl)propyl]oxy}-7-methoxy-2,3-dihydroimidazo[1,2-c]quinazolin-5-yl)-4-methyl-1,3-thiazole-5-carboxamide |
| 39 | 109.7 | 122.3 | 5.32 | 2-amino-N-(8-{[(2R)-2-hydroxy-3-(morpholin-4-yl)propyl]oxy}-7-methoxy-2,3-dihydroimidazo[1,2-c]quinazolin-5-yl)-4-methyl-1,3-thiazole-5-carboxamide |
| 40 | 88.0 | 72.7 | 3.09 | N-(8-{[(2R)-2-hydroxy-3-(pyrrolidin-1-yl)propyl]oxy}-7-methoxy-2,3-dihydroimidazo[1,2-c]quinazolin-5-yl)-1,3-oxazole-5-carboxamide |
| 41 | 95.7 | 99.3 | 5.83 | N-(8-{[(2R)-3-(dipropan-2-ylamino)-2-hydroxypropyl]oxy}-7-methoxy-2,3-dihydroimidazo[1,2-c]quinazolin-5-yl)-1,3-thiazole-5-carboxamide |

It is believed that one skilled in the art, using the preceeding information and information available in the art, can utilize the present invention to its fullest extent. Those skilled in the art will recognize that the invention may be practiced with variations on the disclosed structures, materials, compositions and methods without departing from the spirit or scope of the invention as it is set forth herein and such variations are regarded as within the ambit of the invention. The compounds described in the examples are intended to be representative of the invention, and it will be understood that the scope of the invention is not limited by the scope of the examples. The topic headings set forth above are meant as guidance where certain information can be found in the application, but are not intended to be the only source in the application where information on such topics can be found.

References

Abbosh, P. H.; Nephew, K. P. *Thyroid* 2005, 15, 551-561. Multiple signaling pathways converge on β-catenin in thyroid cancer.

Aiello, L. P.; Avery, R. L.; Arrigg, P. G.; Keyt, B. A.; Jampel, H. D.; Shah, S. T.; Pasquale, L. R.; Thieme, H.; Iwamoto, M. A.; Park, J. E.; et al. *N. Engl. J. Med.* 1994, 331, 1480-1487. Vascular endothelial growth factor in ocular fluid of patients with diabetic retinopathy and other retinal disorders.

Ali, I. U.; Schriml, L. M.; Dean, M. *J. Natl. Cancer Inst.* 1999, 91, 1922-1932. Mutational spectra of PTEN/MMAC1 gene: a tumor suppressor with lipid phosphatase activity.

Bachman, K. E.; Argani, P.; Samuels, Y.; Silliman, N.; Ptak, J.; Szabo, S.; Konishi, H.; Karakas, B.; Blair, B. G.; Lin, C.; Peters, B. A.; Velculescu, V. E.; Park, B. H. *Cancer Biol. Therap.* 2004, 3, 772-775. The PIK3CA gene is mutated with high frequency in human breast cancers.

Bader, A. G.; Kang, S.; Vogt, P. K. *Proc. Natl. Acad. Sci. U.S.A.* 2006, 103, 1475-1479. Cancer-specific mutations in PIK3CA are oncogenic in vivo.

Barthwal, M. K.; Sathyanarayana, P.; Kundu, C. N.; Rana, B.; Pradeep, A.; Sharma, C.; Woodgett, J. R.; Rana, A. *J. Biol. Chem.* 2003, 278, 3897-3902. Negative Regulation of Mixed Lineage Kinase 3 by Protein Kinase B/AKT Leads to Cell Survival.

Bénistant, C.; Chapuis, H.; Roche, S. *Oncogene* 2000, 19, 5083-5090. A specific function for phosphatidylinositol 3-kinase α (p85α-p110α) in cell survival and for phosphatidylinositol 3-kinase β (p85α-p110β) in de novo DNA synthesis of human colon carcinoma cells.

Bissery, M.- C.; Nohynek, G.; Sanderink, G.- J.; Lavelle, F. *Anti-Cancer Drugs* 1995, 6, 339-355. Docetaxel (Taxotere): a review of preclinical and clinical experience. Part I: preclinical experience.

Broderick, D. K.; Di, C.; Parrett, T. J.; Samuels, Y. R.; Cummins, J. M.; McLendon, R. E.; Fults, D. W.; Velculescu, V. E.; Bigner, D. D.; Yan, H. *Cancer Res.* 2004, 64, 5048-5050. Mutations of PIK3CA in anaplastic oligodendrogliomas, high-grade astrocytomas, and medulloblastomas.

Brown, R. A.; Shepherd, P. R. *Biochem. Soc. Trans.* 2001, 29, 535-537. Growth factor regulation of the novel class II phosphoinositide 3-kinases.

Brugge, J.; Hung, M.- C.; Mills, G. B. *Cancer Cell* 2007, 12, 104-107. A new mutational aktivation in the PI3K pathway.

Brunet, A.; Bonni, A.; Zigmond, M. J.; Lin, M. Z.; Juo, P.; Hu, L. S.; Anderson, M. J.; Arden, K. C.; Blenis, J.; Greenberg, M. E. *Cell* 1999, 96, 857-868. Akt promotes cell survival by phosphorylating and inhibiting a Forkhead transcription factor.

Byun, D.- S.; Cho, K.; Ryu, B.- K.; Lee, M.- G.; Park, J.- I.; Chae, K.- S.; Kim, H.- J.; Chi, S.- G. *Int. J. Cancer* 2003, 104, 318-327. Frequent monoallelic deletion of PTEN and its reciprocal association with PIK3CA amplification in gastric carcinoma.

Campbell, I. G.; Russell, S. E.; Choong, D. Y. H.; Montgomery, K. G.; Ciavarella, M. L.; Hooi, C. S. F.; Cristiano, B. E.; Pearson, R. B.; Phillips, W. A. *Cancer Res.* 2004, 64, 7678-7681. Mutation of the PIK3CA gene in ovarian and breast cancer.

Cardone, M. H.; Roy, N.; Stennicke, H. R.; Salvesen, G. S.; Franke, T. F.; Stanbridge, E.; Frisch, S.; Reed, J. C. *Science* 1998, 282, 1318-1321. Regulation of cell death protease caspase-9 by phosphorylation.

Chan, T. O.; Tsichlis, P. N. *Sci. STKE* 2001, 2001, pel. PDK2: a complex tail in one Akt.

Chen, Y. L.; Law, P.- Y.; Loh, H. H. *Curr. Med. Chem.: Anti-Cancer Agents* 2005, 5, 575-589. Inhibition of PI3K/Akt signaling: An emerging paradigm for targeted cancer therapy.

Ciechomska, I.; Pyrzynska, B.; Kazmierczak, P.; Kaminska, B. *Oncogene* 2003, 22, 7617-7627. Inhibition of Akt kinase signalling and activation of Forkhead are indispensable for up-regulation of FasL expression in apoptosis of glioma cells.

Cross, D. A. E.; Alessi, D. R.; Cohen, P.; Andjelkovich, M.; Hemmings, B. A. *Nature* 1995, 378, 785-789. Inhibition of glycogen synthase kinase-3 by insulin mediated by protein kinase B.

Cully, M.; You, H.; Levine, A. J.; Mak, T. W. *Nat. Rev. Cancer* 2006, 6, 184-192. Beyond PTEN mutations: the PI3K pathway as an integrator of multiple inputs during tumorigenesis.

Czauderna, F.; Fechtner, M.; Aygun, H.; Arnold, W.; Klippel, A.; Giese, K.; Kaufmann, J. *Nucleic Acids Res.* 2003, 31, 670-682. Functional studies of the PI(3)-kinase signalling pathway employing synthetic and expressed siRNA.

Daly, C.; Wong, V.; Burova, E.; Wei, Y.; Zabski, S.; Griffiths, J.; Lai, K.- M.; Lin, H. C.; Ioffe, E.; Yancopoulos, G. D.; Rudge, J. S. *Genes Dev.* 2004, 18, 1060-1071. Angiopoietin-1 modulates endothelial cell function and gene expression via the transcription factor FKHR (FOXO1).

del Peso, L.; Gonzalez-Garcia, M.; Page, C.; Herrera, R.; Nunez, G. *Science* 1997, 278, 687-689. Interleukin-3-induced phosphorylation of BAD through the protein kinase Akt.

Diehl, J. A.; Cheng, M.; Roussel, M. F.; Sherr, C. J. *Genes Dev.* 1998, 12, 3499-3511. Glycogen synthase kinase-3b regulates cyclin D1 proteolysis and subcellular localization.

Dijkers, P. F.; Medema, R. H.; Lammers, J.- W. J.; Koenderman, L.; Coffer, P. J. *Curr. Biol.* 2000, 10, 1201-1204. Expression of the pro-apoptotic Bcl-2 family member Bim is regulated by the Forkhead transcription factor FKHR-L1.

Domin, J.; Waterfield, M. D. *FEBS Lett.* 1997, 410, 91-95. Using structure to define the function of phosphoinositide 3-kinase family members.

Downes, C. P.; Gray, A.; Lucocq, J. M. *Trends Cell Biol.* 2005, 15, 259-268. Probing phosphoinositide functions in signaling and membrane trafficking.

Edelman, M. J.; Gandara, D. R. *Cancer Chemotherap. Pharmacol.* 1996, 37, 385-393. Promising new agents in the treatment of non-small cell lung cancer.

Figueroa, C.; Tarras, S.; Taylor, J.; Vojtek, A. B. *J. Biol. Chem.* 2003, 278, 47922-47927. Akt2 negatively regulates assembly of the POSH-MLK-JNK signaling complex.

Fleming, I. N.; Gray, A.; Downes, C. P. *Biochem. J.* 2000, 351, 173-182. Regulation of the Rac1-specific exchange factor tiam1 involves both phosphoinositide 3-kinase-dependent and -independent components.

Funaki, M.; Katagiri, H.; Inukai, K.; Kikuchi, M.; Asano, T. *Cell. Signalling* 2000, 12, 135-142. Structure and function of phosphatidylinositol-3,4 kinase.

Gallia, G. L.; Rand, V.; Siu, I. M.; Eberhart, C. G.; James, C. D.; Marie, S. K. N.; Oba-Shinjo, S. M.; Carlotti, C. G.; Caballero, O. L.; Simpson, A. J. G.; Brock, M. V.; Massion, P. P.; Carson, B. S., Sr.; Riggins, G. J. *Mol.*

Cancer Res. 2006, 4, 709-714. PIK3CA gene mutations in pediatric and adult glioblastoma multiforme.

Garcia-Rostan, G.; Costa, A. M.; Pereira-Castro, I.; Salvatore, G.; Hernandez, R.; Hermsem, M. J. A.; Herrero, A.; Fusco, A.; Cameselle-Teijeiro, J.; Santoro, M. *Cancer Res.* 2005, 65, 10199-10207. Mutation of the PIK3CA gene in anaplastic thyroid cancer.

Gershtein, E. S.; Shatskaya, V. A.; Ermilova, V. D.; Kushlinsky, N. E.; Krasil'nikov, M. A. *Clin. Chim. Acta* 1999, 287, 59-67. Phosphatidylinositol 3-kinase expression in human breast cancer.

Gottschalk, A. R.; Doan, A.; Nakamura, J. L.; Stokoe, D.; Haas-Kogan, D. A. *Int. J. Radiat. Oncol. Biol. Phys.* 2005, 63, 1221-1227. Inhibition of phosphatidylinositol-3-kinase causes increased sensitivity to radiation through a PKB-dependent mechanism.

Gupta, A. K.; Cerniglia, G. J.; Mick, R.; Ahmed, M. S.; Bakanauskas, V. J.; Muschel, R. J.; McKenna, W. G. *Int. J. Radiat. Oncol. Biol. Phys.* 2003, 56, 846-853. Radiation sensitization of human cancer cells in vivo by inhibiting the activity of PI3K using LY294002.

Haas-Kogan, D.; Shalev, N.; Wong, M.; Mills, G.; Yount, G.; Stokoe, D. *Curr. Biol.* 1998, 8, 1195-1198. Protein kinase B (PKB/Akt) activity is elevated in glioblastoma cells due to mutation of the tumor suppressor PTEN/MMAC.

Hartmann, C.; Bartels, G.; Gehlhaar, C.; Holtkamp, N.; von Deimling, A. *Acta Neuropathol.* 2005, 109, 639-642. PIK3CA mutations in glioblastoma multiforme.

Hennessy, B. T.; Smith, D. L.; Ram, P. T.; Lu, Y.; Mills, G. B. *Nat. Rev. Drug Disc.* 2005, 4, 988-1004. Exploiting the PI3K/AKT Pathway for Cancer Drug Discovery.

Hodgkinson, C. P.; Sale, E. M.; Sale, G. *J. Biochemistry* 2002, 41, 10351-10359. Characterization of PDK2 activity against Protein Kinase B gamma.

Hresko, R. C.; Murata, H.; Mueckler, M. *J. Biol. Chem.* 2003, 278, 21615-21622. Phosphoinositide-dependent Kinase-2 is a distinct protein kinase enriched in a novel cytoskeletal fraction associated with adipocyte plasma membranes.

Huang, C.; Ma, W.- Y.; Dong, Z. *Mol. Cell. Biol.* 1996, 16, 6427-6435. Requirement for phosphatidylinositol 3-kinase in epidermal growth factor-induced AP-1 transactivation and transformation in JB6 P+ cells.

Hupp, T. R.; Lane, D. P.; Ball, K. L. *Biochem. J.* 2000, 352, 1-17. Strategies for manipulating the p53 pathway in the treatment of human cancer.

Ihle, N. T.; Williams, R.; Chow, S.; Chew, W.; Berggren, M. I.; Paine-Murrieta, G.; Minion, D. J.; Halter, R. J.; Wipf, P.; Abraham, R.; Kirkpatrick, L.; Powis, G. *Mol. Cancer Ther.* 2004, 3, 763-772. Molecular pharmacology and antitumor activity of PX-866, a novel inhibitor of phosphoinositide-3-kinase signaling.

Ikenoue, T.; Kanai, F.; Hikiba, Y.; Obata, T.; Tanaka, Y.; Imamura, J.; Ohta, M.; Jazag, A.; Guleng, B.; Tateishi, K.; Asaoka, Y.; Matsumura, M.; Kawabe, T.; Omata, M. *Cancer Res.* 2005, 65, 4562-4567. Functional analysis of PIK3CA gene mutations in human colorectal cancer.

Ishii, N.; Maier, D.; Merlo, A.; Tada, M.; Sawamura, Y.; Diserens, A.- C.; Van Meir, E. G. *Brain Pathol.* 1999, 9, 469-479. Frequent co-alterations of TP53, p16/CDKN2A, p14ARF, PTEN tumor suppressor genes in human glioma cell lines.

Itoh, T.; Takenawa, T. *Cell. Signalling* 2002, 14, 733-743. Phosphoinositide-binding domains. Functional units for temporal and spatial regulation of intracellular signalling.

Janssen, J. W. G.; Schleithoff, L.; Bartram, C. R.; Schulz, A. S. *Oncogene* 1998, 16, 1767-1772. An oncogenic fusion product of the phosphatidylinositol 3-kinase p85b subunit and HUMORF8, a putative deubiquitinating enzyme.

Jia, S.; Liu, Z.; Zhang, S.; Liu, P.; Zhang, L.; Lee, S. H.; Zhang, J.; Signoretti, S.; Loda, M.; Roberts, T. M.; Zhao, J. J. *Nature* 2008, 454, 776-779. Essential roles of PI(3)K-p110β in cell growth, metabolism and tumorigenesis.

Jia, S.; Roberts, T. M.; Zhao, J. J. *Curr. Opin. Cell Biol.* 2009, 21, 199-208. Should individual PI3 kinase isoforms be targeted in cancer?

Jimenez, C.; Jones, D. R.; Rodriguez-Viciana, P.; Gonzalez-Garcia, A.; Leonardo, E.; Wennstrom, S.; Von Kobbe, C.; Toran, J. L.; R.- Borlado, L.; Calvo, V.; Copin, S. G.; Albar, J. P.; Gaspar, M. L.; Diez, E.; Marcos, M. A. R.; Downward, J.; Martinez-A, C.; Merida, I.; Carrera, A. C. *EMBO J.* 1998, 17, 743-753. Identification and characterization of a new oncogene derived from the regulatory subunit of phosphoinositide 3-kinase.

Jucker, M.; Sudel, K.; Horn, S.; Sickel, M.; Wegner, W.; Fiedler, W.; Feldman, R. A. *Leukemia* 2002, 16, 894-901. Expression of a mutated form of the p85a regulatory subunit of phosphatidylinositol 3-kinase in a Hodgkin's lymphoma-derived cell line (CO).

Kang, S.; Bader, A. G.; Vogt, P. K. *Proc. Natl. Acad. Sci. U.S.A.* 2005, 102, 802-807. Phosphatidylinositol 3-kinase mutations identified in human cancer are oncogenic.

Kang, S.; Denley, A.; Vanhaesebroeck, B.; Vogt, P. K. *Proc. Natl. Acad. Sci. U.S.A.* 2006, 103, 1289-1294. Oncogenic transformation induced by the p110b, -g, and -d isoforms of class I phosphoinositide 3-kinase.

Katso, R.; Okkenhaug, K.; Ahmadi, K.; White, S.; Timms, J.; Waterfield, M. D. *Ann. Rev. Cell. Dev. Biol.* 2001, 17, 615-675. Cellular function of phosphoinositide 3-kinases: implications for development, immunity, homeostasis, and cancer.

Kim, A. H.; Khursigara, G.; Sun, X.; Franke, T. F.; Chao, M. V. *Mol. Cell. Biol.* 2001, 21, 893-901. Akt phosphorylates and negatively regulates apoptosis signal-regulating kinase 1.

Kim, D.; Dan, H. C.; Park, S.; Yang, L.; Liu, Q.; Kaneko, S.; Ning, J.; He, L.; Yang, H.; Sun, M.; Nicosia, S. V.; Cheng, J. Q. *Front. Biosci.* 2005, 10, 975-987. AKT/PKB signaling mechanisms in cancer and chemoresistance.

Klippel, A.; Kavanaugh, W. M.; Pot, D.; Williams, L. T. *Mol. Cell. Biol.* 1997, 17, 338-344. A specific product of phosphatidylinositol 3-kinase directly activates the protein kinase Akt through its pleckstrin homology domain.

Kodaki, T.; Woscholski, R.; Hallberg, B.; Rodriguez-Viciana, P.; Downward, J.; Parker, P. J. *Curr. Biol.* 1994, 4, 798-806. The activation of phosphatidylinositol 3-kinase by Ras.

Kops, G. J. P. L.; De Ruiter, N. D.; De Vries-Smits, A. M. M.; Powell, D. R.; Bos, J. L.; Burgering, B. M. T. *Nature* 1999, 398, 630-634. Direct control of the Forkhead transcription factor AFX by protein kinase B.

Lee, J. T., Jr.; Steelman, L. S.; McCubrey, J. A. *Cancer Res.* 2004, 64, 8397-8404. Phosphatidylinositol 3'-Kinase Activation Leads to Multidrug Resistance Protein-1 Expression and Subsequent Chemoresistance in Advanced Prostate Cancer Cells.

Lee, J. W.; Soung, Y. H.; Kim, S. Y.; Lee, H. W.; Park, W. S.; Nam, S. W.; Kim, S. H.; Lee, J. Y.; Yoo, N. J.; Lee, S. H. *Oncogene* 2005, 24, 1477-1480. PIK3CA gene is frequently mutated in breast carcinomas and hepatocellular carcinomas.

Lemmon, M. A. *Traffic* 2003, 4, 201-213. Phosphoinositide recognition domains.

Levine, D. A.; Bogomolniy, F.; Yee, C. J.; Lash, A.; Barakat, R. R.; Borgen, P. I.; Boyd, J. *Clin. Cancer Res.* 2005, 11, 2875-2878. Frequent Mutation of the PIK3CA Gene in Ovarian and Breast Cancers.

Li, J.; Yen, C.; Liaw, D.; Podsypanina, K.; Bose, S.; Wang, S. I.; Puc, J.; Miliaresis, C.; Rodgers, L.; McCombie, R.; Bigner, S. H.; Giovanella, B. C.; Ittmann, M.; Tycko, B.; Hibshoosh, H.; Wigler, M. H.; Parsons, R. *Science* 1997, 275, 1943-1947. PTEN, a putative protein tyrosine phosphatase gene mutated in human brain, breast, and prostate cancer.

Li, V. S. W.; Wong, C. W.; Chan, T. L.; Chan, A. S. W.; Zhao, W.; Chu, K.-M.; So, S.; Chen, X.; Yuen, S. T.; Leung, S. Y. *BMC Cancer* 2005, 5, 29. Mutations of PIK3CA in gastric adenocarcinoma.

Li, Y.-L.; Tian, Z.; Wu, D.-Y.; Fu, B.-Y.; Xin, Y. *World J. Gastroenterol.* 2005, 11, 285-288. Loss of heterozygosity on 10q23.3 and mutation of tumor suppressor gene PTEN in gastric cancer and precancerous lesions.

Liao, Y.; Hung, M.-C. *Mol. Cell. Biol.* 2003, 23, 6836-6848. Regulation of the activity of p38 mitogen-activated protein kinase by Akt in cancer and adenoviral protein E1A-mediated sensitization to apoptosis.

Liu, P.; Cheng, H.; Roberts, T. M.; Zhao, J. J. *Nat. Rev. Drug Disc.* 2009, 8, 627-644. Targeting the phosphoinositide 3-kinase pathway in cancer.

Lopez-Ilasaca, M.; Li, W.; Uren, A.; Yu, J.-c.; Kazlauskas, A.; Gutkind, J. S.; Heidaran, M. A. *Biochem Biophys. Res. Commun.* 1997, 232, 273-277. Requirement of phosphatidylinositol-3 kinase for activation of JNK/SAPKs by PDGF.

Lopez, P. F.; Sippy, B. D.; Lambert, H. M.; Thach, A. B.; Hinton, D. R. *Invest. Ophthalmol. Vis. Sci.* 1996, 37, 855-868. Transdifferentiated retinal pigment epithelial cells are immunoreactive for vascular endothelial growth factor in surgically excised age-related macular degeneration-related choroidal neovascular membranes.

Ma, Y.-Y.; Wei, S.-J.; Lin, Y.-C.; Lung, J.-C.; Chang, T.-C.; Whang-Peng, J.; Liu, J. M.; Yang, D.-M.; Yang, W. K.; Shen, C.-Y. *Oncogene* 2000, 19, 2739-2744. PIK3CA as an oncogene in cervical cancer.

Mayo, L. D.; Dixon, J. E.; Durden, D. L.; Tonks, N. K.; Donner, D. B. *J. Biol. Chem.* 2002, 277, 5484-5489. PTEN protects p53 from Mdm2 and sensitizes cancer cells to chemotherapy.

Momand, J.; Wu, H.-H.; Dasgupta, G. *Gene* 2000, 242, 15-29. MDM2—master regulator of the p53 tumor suppressor protein.

Motti, M. L.; De Marco, C.; Califano, D.; Fusco, A.; Viglietto, G. *Cell Cycle* 2004, 3, 1074-1080. Akt-dependent T198 phosphorylation of cyclin-dependent kinase inhibitor p27kip1 in breast cancer.

Myers, M. P.; Pass, I.; Batty, I. H.; Van Der Kaay, J.; Stolarov, J. P.; Hemmings, B. A.; Wigler, M. H.; Downes, C. P.; Tonks, N. K. *Proc. Natl. Acad. Sci. U.S.A.* 1998, 95, 13513-13518. The lipid phosphatase activity of PTEN is critical for its tumor suppressor function.

Nagata, Y.; Lan, K.-H.; Zhou, X.; Tan, M.; Esteva, F. J.; Sahin, A. A.; Klos, K. S.; Li, P.; Monia, B. P.; Nguyen, N. T.; Hortobagyi, G. N.; Hung, M.-C.; Yu, D. *Cancer Cell* 2004, 6, 117-127. PTEN activation contributes to tumor inhibition by trastuzumab, and loss of PTEN predicts trastuzumab resistance in patients.

Naito, A. T.; Akazawa, H.; Takano, H.; Minamino, T.; Nagai, T.; Aburatani, H.; Komuro, I. *Circ. Res.* 2005, 97, 144-151. Phosphatidylinositol 3-Kinase-Akt Pathway Plays a Critical Role in Early Cardiomyogenesis by Regulating Canonical Wnt Signaling.

Nema, S.; Washkuhn, R. J.; Brendel, R. J. *PDA J. Pharm. Sci. Technol.* 1997, 51, 166-171. Excipients and their use in injectable products.

Oda, K.; Stokoe, D.; Taketani, Y.; McCormick, F. *Cancer Res.* 2005, 65, 10669-10673. High Frequency of Coexistent Mutations of PIK3CA and PTEN Genes in Endometrial Carcinoma.

Ogawara, Y.; Kishishita, S.; Obata, T.; Isazawa, Y.; Suzuki, T.; Tanaka, K.; Masuyama, N.; Gotoh, Y. *J. Biol. Chem.* 2002, 277, 21843-21850. Akt enhances Mdm2-mediated ubiquitination and degradation of p53.

Oki, E.; Kakeji, Y.; Baba, H.; Tokunaga, E.; Nakamura, T.; Ueda, N.; Futatsugi, M.; Yamamoto, M.; Ikebe, M.; Maehara, Y. *J. Gastroenterol. Hepatol.* 2006, 21, 814-818. Impact of loss of heterozygosity of encoding phosphate and tensin homolog on the prognosis of gastric cancer.

Olson, J. M.; Hallahan, A. R. *Trends Mol. Med.* 2004, 10, 125-129. p38 MAP kinase: a convergence point in cancer therapy.

Osaki, M.; Oshimura, M.; Ito, H. *Apoptosis* 2004, 9, 667-676. PI3K-Akt pathway: Its functions and alterations in human cancer.

Pastorino, J. G.; Tafani, M.; Farber, J. L. *J. Biol. Chem.* 1999, 274, 19411-19416. Tumor necrosis factor induces phosphorylation and translocation of BAD through a phosphatidylinositide-3-OH kinase-dependent pathway.

Pendaries, C.; Tronchere, H.; Plantavid, M.; Payrastre, B. *FEBS Lett.* 2003, 546, 25-31. Phosphoinositide signaling disorders in human diseases.

Phillips, W. A.; St. Clair, F.; Munday, A. D.; Thomas, R. J. S.; Mitchell, C. A. *Cancer* 1998, 83, 41-47. Increased levels of phosphatidylinositol 3-kinase activity in colorectal tumors.

Philp, A. J.; Campbell, I. G.; Leet, C.; Vincan, E.; Rockman, S. P.; Whitehead, R. H.; Thomas, R. J. S.; Phillips, W. A. *Cancer Res.* 2001, 61, 7426-7429. The phosphatidylinositol 3'-kinase p85a gene is an oncogene in human ovarian and colon tumors.

Powell, M. F.; Nguyen, T.; Baloian, L. *PDA J. Pharm. Sci. Technol.* 1998, 52, 238-311. Compendium of excipients for parenteral formulations.

Powis, G.; Bonjouklian, R.; Berggren, M. M.; Gallegos, A.; Abraham, R.; Ashendel, C.; Zalkow, L.; Matter, W. F.; Dodge, J. *Cancer Res.* 1994, 54, 2419-2423. Wortmannin, a potent and selective inhibitor of phosphatidylinositol-3-kinase.

Pu, P.; Kang, C.; Zhang, Z.; Liu, X.; Jiang, H. *Technol. Cancer Res. Treat.* 2006, 5, 271-280. Downregulation of PIK3CB by siRNA suppresses malignant glioma cell growth in vitro and in vivo.

Rahimi, N.; Tremblay, E.; Elliott, B. *J. Biol. Chem.* 1996, 271, 24850-24855. Phosphatidylinositol 3-kinase activity is required for hepatocyte growth factor-induced mitogenic signals in epithelial cells.

Roche, S.; Downward, J.; Raynal, P.; Courtneidge, S. A. *Mol. Cell. Biol.* 1998, 18, 7119-7129. A function for phosphatidylinositol 3-kinase b (p85a-p110b) in fibroblasts during mitogenesis: requirement for insulin- and lysophosphatidic acid-mediated signal transduction.

Roche, S.; Koegl, M.; Courtneidge, S. A. *Proc. Natl. Acad. Sci. U.S.A.* 1994, 91, 9185-9189. The phosphatidylinositol 3-kinase a is required for DNA synthesis induced by some, but not all, growth factors.

Romashkova, J. A.; Makarov, S. S. *Nature* 1999, 401, 86-90. Nf-kB is a target of Akt in anti-apoptotic PDGF signalling.

Saal, L. H.; Holm, K.; Maurer, M.; Memeo, L.; Su, T.; Wang, X.; Yu, J. S.; Malmstroem, P.- O.; Mansukhani, M.; Enoksson, J.; Hibshoosh, H.; Borg, A.; Parsons, R. *Cancer Res.* 2005, 65, 2554-2559. PIK3CA mutations correlate with hormone receptors, node metastasis, and ERBB2, and are mutually exclusive with PTEN loss in human breast carcinoma.

Samuels, Y.; Diaz, L. A., Jr.; Schmidt-Kittler, O.; Cummins, J. M.; DeLong, L.; Cheong, I.; Rago, C.; Huso, D. L.; Lengauer, C.; Kinzler, K. W.; Vogelstein, B.; Velculescu, V. E. *Cancer Cell* 2005, 7, 561-573. Mutant PIK3CA promotes cell growth and invasion of human cancer cells.

Samuels, Y.; Ericson, K. *Curr. Opin. Oncol.* 2006, 18, 77-82. Oncogenic PI3K and its role in cancer.

Samuels, Y.; Wang, Z.; Bardelli, A.; Silliman, N.; Ptak, J.; Szabo, S.; Yan, H.; Gazdar, A.; Powell, S. M.; Riggins, G. J.; Willson, J. K. V.; Markowitz, S.; Kinzler, K. W.; Vogelstein, B.; Velculescu, V. E. *Science* 2004, 304, 554. Brevia: High frequency of mutations of the PIK3Ca gene in human cancers.

Scheid, M. P.; Marignani, P. A.; Woodgett, J. R. *Mol. Cell. Biol.* 2002, 22, 6247-6260. Multiple phosphoinositide 3-kinase-dependent steps in activation of protein kinase B.

Schultz, R. M.; Merriman, R. L.; Andis, S. L.; Bonjouklian, R.; Grindey, G. B.; Rutherford, P. G.; Gallegos, A.; Massey, K.; Powis, G. *Anticancer Res.* 1995, 15, 1135-1139. In vitro and in vivo antitumor activity of the phosphatidylinositol-3-kinase inhibitor, wortmannin.

Segrelles, C.; Moral, M.; Lara, M. F.; Ruiz, S.; Santos, M.; Leis, H.; Garcia-Escudero, R.; Martinez-Cruz, A. B.; Martinez-Palacio, J.; Hernandez, P.; Ballestin, C.; Paramio, J. M. *Oncogene* 2006, 25, 1174-1185. Molecular determinants of Akt-induced keratinocyte transformation.

Sekimoto, T.; Fukumoto, M.; Yoneda, Y. *EMBO J.* 2004, 23, 1934-1942. 14-3-3 suppresses the nuclear localization of threonine 157-phosphorylated p27Kip1.

Semba, S.; Itoh, N.; Ito, M.; Youssef, E. M.; Harada, M.; Moriya, T.; Kimura, W.; Yamakawa, M. *Clin. Cancer Res.* 2002, 8, 3824-3831. Down-regulation of PIK3CG catalytic subunit of phosphatidylinositol 3-OH kinase by CpG hypermethylation in human colorectal carcinoma.

Shayesteh, L.; Lu, Y.; Kuo, W.- L.; Baldocchi, R.; Godfrey, T.; Collins, C.; Pinkel, D.; Powell, B.; Mills, G. B.; Gray, J. W. *Nat. Genet.* 1999, 21, 99-102. PIK3CA is implicated as an oncogene in ovarian cancer.

Shekar, S. C.; Wu, H.; Fu, Z.; Yip, S.- C.; Nagajyothi; Cahill, S. M.; Girvin, M. E.; Backer, J. M. *J. Biol. Chem.* 2005, 280, 27850-27855. Mechanism of Constitutive Phosphoinositide 3-Kinase Activation by Oncogenic Mutants of the p85 Regulatory Subunit.

Silvestrini, R.; Zaffaroni, N.; Orlandi, L.; Oriana, S. *Stem Cells* 1993, 11, 528-535. In vitro cytotoxic activity of taxol and taxotere on primary cultures and established cell lines of human ovarian cancer.

Stahl, J. M.; Cheung, M.; Sharma, A.; Trivedi, N. R.; Shanmugam, S.; Robertson, G. P. *Cancer Res.* 2003, 63, 2881-2890. Loss of PTEN Promotes Tumor Development in Malignant Melanoma.

Stambolic, V.; Suzuki, A.; De La Pompa, J. L.; Brothers, G. M.; Mirtsos, C.; Sasaki, T.; Ruland, J.; Penninger, J. M.; Siderovski, D. P.; Mak, T. W. *Cell* 1998, 95, 29-39. Negative regulation of PKB/Akt-Dependent cell survival by the tumor suppressor PTEN.

Stauffer, F.; Holzer, P.; Garcia-Echeverria, C. *Curr. Med. Chem.: Anti-Cancer Agents* 2005, 5, 449-462. Blocking the PI3K/PKB pathway in tumor cells.

Steck, P. A.; Pershouse, M. A.; Jasser, S. A.; Yung, W. K. A.; Lin, H.; Ligon, A. H.; Langford, L. A.; Baumgard, M. L.; Hattier, T.; Davis, T.; Frye, C.; Hu, R.; Swedlund, B.; Teng, D. H. F.; Tavtigian, S. V. *Nat. Genet.* 1997, 15, 356-362. Identification of a candidate tumor suppressor gene, MMAC1, at chromosome 10q23.3 that is mutated in multiple advanced cancers.

Stephens, L.; Williams, R.; Hawkins, P. *Curr. Opin. Pharmacol.* 2005, 5, 357-365. Phosphoinositide 3-kinases as drug targets in cancer.

Still, W. C.; Kahn, M.; Mitra, A. *J. Org. Chem.* 1978, 43, 2923-2925. Rapid chromatographic technique for preparative separations with moderate resolution.

Strickley, R. G. *PDA J. Pharm. Sci. Technol.* 1999, 53, 324-349. Parenteral formulations of small molecules therapeutics marketed in the United States (1999). Part I.

Su, J. D.; Mayo, L. D.; Donner, D. B.; Durden, D. L. *Cancer Res.* 2003, 63, 3585-3592. PTEN and Phosphatidylinositol 3'-Kinase Inhibitors Up-Regulate p53 and Block Tumor-induced Angiogenesis: Evidence for an Effect on the Tumor and Endothelial Compartment.

Tanaka, M.; Grossman, H. B. *Gene Therap.* 2003, 10, 1636-1642. In vivo gene therapy of human bladder cancer with PTEN suppresses tumor growth, downregulates phosphorylated Akt, and increases sensitivity to doxorubicin.

Tang, E. D.; Nunez, G.; Barr, F. G.; Guan, K.- L. *J. Biol. Chem.* 1999, 274, 16741-16746. Negative regulation of the forkhead transcription factor FKHR by Akt.

Taylor, V.; Wong, M.; Brandts, C.; Reilly, L.; Dean, N. M.; Cowsert, L. M.; Moodie, S.; Stokoe, D. *Mol. Cell. Biol.* 2000, 20, 6860-6871. 5' Phospholipid phosphatase SHIP-2 causes protein kinase B inactivation and cell cycle arrest in glioblastoma cells.

Toker, A. *Cell Mol. Life Sci.* 2002, 59, 761-779. Phosphoinositides and signal transduction.

Traer, C. J.; Foster, F. M.; Abraham, S. M.; Fry, M. J. *Bull. Cancer (Paris)* 2006, 93, E53-58. Are class II phosphoinositide 3-kinases potential targets for anticancer therapies?

Vanhaesebroeck, B.; Leevers, S. J.; Ahmadi, K.; Timms, J.; Katso, R.; Driscoll, P. C.; Woscholski, R.; Parker, P. J.; Waterfield, M. D. *Ann. Rev. Biochem.* 2001, 70, 535-602. Synthesis and function of 3-phosphorylated inositol lipids.

Vanhaesebroeck, B.; Waterfield, M. D. *Exp. Cell Res.* 1999, 253, 239-254. Signaling by Distinct Classes of Phosphoinositide 3-Kinases.

Vivanco, I.; Sawyers, C. L. *Nat. Rev. Cancer* 2002, 2, 489-501. The phosphatidylinositol 3-Kinase-AKT pathway in human cancer.

Vogt, P. K.; Gymnopoulos, M.; Hart, J. R. *Curr. Opin. Genet. Dev.* 2009, 19, 12-17. PI 3-kinase and cancer: changing accents.

Wang, Y.; Helland, A.; Holm, R.; Kristensen Gunnar, B.; Borresen-Dale, A.- L. *Human Mutation* 2005, 25, 322. PIK3CA mutations in advanced ovarian carcinomas.

Wee, S.; Lengauer, C.; Wiederschain, D. *Curr. Opin. Oncol.* 2008, 20, 77-82. Class IA phosphoinositide 3-kinase isoforms and human tumorigenesis: implications for cancer drug discovery and development.

West, K. A.; Castillo, S. S.; Dennis, P. A. *Drug Resist. Updates* 2002, 5, 234-248. Activation of the PI3K/Akt pathway and chemotherapeutic resistance.

Whyte, D. B.; Holbeck, S. L. *Biochem Biophys. Res. Commun.* 2006, 340, 469-475. Correlation of PIK3Ca mutations with gene expression and drug sensitivity in NCI-60 cell lines.

Wilker, E.; Lu, J.; Rho, O.; Carbajal, S.; Beltran, L.; DiGiovanni, J. *Mol. Carcinog.* 2005, 44, 137-145. Role of PI3K/Akt signaling in insulin-like growth factor-1 (IGF-1) skin tumor promotion.

Workman, P. *Biochem. Soc. Trans.* 2004, 32, 393-396. Inhibiting the phosphoinositide 3-kinase pathway for cancer treatment.

Wu, G.; Xing, M.; Mambo, E.; Huang, X.; Liu, J.; Guo, Z.; Chatterjee, A.; Goldenberg, D.; Gollin, S. M.; Sukumar, S.; Trink, B.; Sidransky, D. *Breast Cancer Res.* 2005, 7, R609-R616. Somatic mutation and gain of copy number of PIK3CA in human breast cancer.

Yap, D. B.; Hsieh, J. K.; Lu, X. *J. Biol. Chem.* 2000, 275, 37296-37302. Mdm2 inhibits the apoptotic function of p53 mainly by targeting it for degradation.

Yuan, T. L.; Cantley, L. C. *Oncogene* 2008, 27, 5497-5510. PI3K pathway alterations in cancer: variations on a theme.

Yuan, Z.- q.; Feldman, R. I.; Sussman, G. E.; Coppola, D.; Nicosia, S. V.; Cheng, J. Q. *J. Biol. Chem.* 2003, 278, 23432-23440. AKT2 Inhibition of Cisplatin-induced JNK/p38 and Bax Activation by Phosphorylation of ASK1: Implication of AKT2 in Chemoresistance.

Zhao, H.; Dupont, J.; Yakar, S.; Karas, M.; LeRoith, D. *Oncogene* 2004, 23, 786-794. PTEN inhibits cell proliferation and induces apoptosis by downregulating cell surface IGF-IR expression in prostate cancer cells.

Zhao, J. J.; Cheng, H.; Jia, S.; Wang, L.; Gjoerup, O. V.; Mikami, A.; Roberts, T. M. *Proc. Natl. Acad. Sci. U.S.A.* 2006, 103, 16296-16300. The p110a isoform of PI3K is essential for proper growth factor signaling and oncogenic transformation.

Zhichkin, P.; Fairfax, D. J.; Eisenbeis, S. A. *Synthesis* 2002, 720-722. A general procedure for the synthesis of 2-substituted pyrimidine-5-carboxylic esters.

Zhou, B. P.; Liao, Y.; Xia, W.; Spohn, B.; Lee, M. H.; Hung, M. C. *Nat. Cell Biol.* 2001, 3, 245-252. Cytoplasmic localization of p21Cip1/WAF1 by Akt-induced phosphorylation in HER-2/neu-overexpressing cells.

All publications and patents cited above are incorporated herein by reference.

The invention claimed is:

1. A compound of formula (I):

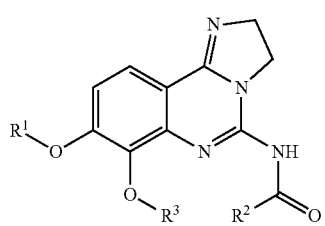

wherein:

$R^1$ is -$(CH_2)_n$-$(CHR^4)$-$(CH_2)_m$-$N(R^5)(R^{5'})$;

$R^2$ is a heteroaryl of structure:

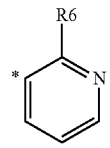

wherein:
* indicates the point of attachment of said heteroaryl with the rest of the compound of formula (I);

$R^3$ is methyl;

$R^4$ is hydroxy in the (R)-configuration;

$R^5$ and $R^{5'}$ are the same or different and are, independently of each other, a hydrogen atom, $C_1$-$C_6$-alkyl, $C_3$-$C_6$-cycloalkyl-$C_1$-$C_6$-alkyl, or $C_1$-$C_6$-alkoxy-$C_1$-$C_6$-alkyl, or $R^5$ and $R^{5'}$ are taken together with the nitrogen atom to which they are bound to form a 3- to 7- membered nitrogen containing heterocyclic ring optionally containing at least one additional heteroatom selected from oxygen, nitrogen, and sulfur, and which is optionally substituted with 1 or more $R^{6'}$ groups;

$R^6$ is a hydrogen atom, a halogen atom, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, aryl, aryl-$C_1$-$C_6$-alkyl, heteroaryl, heteroaryl-$C_1$-$C_6$-alkyl, 3- to 8-membered heterocyclic ring, 3- to 8-membered heterocyclyl-$C_1$-$C_6$-alkyl, -$C_1$-$C_6$-alkyl-$OR^7$, -$C_1$-$C_6$-alkyl-$SR^7$, -$C_1$-$C_6$-alkyl-$N(R^7)(R^{7'})$, -$C_1$-$C_6$-alkyl-$C(=O)R^7$, -CN, -$C(=O)OR^7$, -$C(=O)N(R^7)(R^{7'})$, -$OR^7$, -$SR^7$, -$N(R^7)(R^{7'})$, or
-$NR^7C(=O)R^7$, each of which is optionally substituted with 1 or more $R^8$ groups;

each occurrence of $R^{6'}$ is the same or different and is independently $C_1$-$C_6$-alkyl, $C_3$-$C_6$-cycloalkyl-$C_1$-$C_6$-alkyl, or $C_1$-$C_6$-alkyl-$OR^7$;

each occurrence of $R^7$ and $R^{7'}$ is the same or different and is independently a hydrogen atom, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_3$-$C_6$-cycloalkenyl, aryl, aryl-$C_1$-$C_6$-alkyl, heteroaryl, 3- to 8-membered heterocyclic ring, 3- to 8-membered heterocyclyl-$C_1$-$C_6$-alkyl, or heteroaryl-$C_1$-$C_6$-alkyl;

each occurrence of $R^8$ is independently a halogen atom, nitro, hydroxy, cyano, formyl, acetyl, amino, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-cycloalkenyl, aryl, aryl-$C_1$-$C_6$-alkyl, heteroaryl, 3- to 8-membered heterocyclic ring, heterocyclyl-$C_1$-$C_6$-alkyl, or heteroaryl-$C_1$-$C_6$-alkyl; and n is an integer of 1 and m is an integer of 1;

with the proviso that when:
- said $R^5$ and $R^{5'}$ are taken together with the nitrogen atom to which they are bound to form:

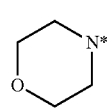

wherein * indicates the point of attachment with the rest of the structure of formula (I), then

- $R^2$ is not:

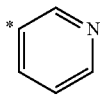

wherein * indicates the point of attachment with the rest of the structure of formula (I),
or a stereoisomer, a tautomer, an N-oxide, or a physiologically acceptable salt thereof, or a mixture of any of the foregoing.

2. The compound according to claim 1, wherein:
$R^5$ and $R^{5'}$ are taken together with the nitrogen atom to which they are bound to form a 3- to 7- membered nitrogen containing heterocyclic ring optionally containing at least one additional heteroatom selected from oxygen and nitrogen and which is optionally substituted with 1 or more $R^{6'}$ groups,
or a stereoisomer, a tautomer, an N-oxide, or a physiologically acceptable salt thereof, or a mixture of any of the foregoing.

3. The compound according to claim 1, wherein:
$R^5$ and $R^{5'}$ are taken together with the nitrogen atom to which they are bound to form morpholinyl,
or a stereoisomer, a tautomer, an N-oxide, or a physiologically acceptable salt thereof, or a mixture of any of the foregoing.

4. The compound according to claim 1, wherein $R^6$ is $C_1$-$C_6$-alkyl optionally substituted with 1 or more $R^8$ groups,
or a stereoisomer, a tautomer, an N-oxide, or a physiologically acceptable salt thereof, or a mixture of any of the foregoing.

5. The compound according to claim 1, wherein $R^6$ is $C_1$-$C_3$-alkyl,
or a stereoisomer, a tautomer, an N-oxide, or a physiologically acceptable salt thereof, or a mixture of any of the foregoing.

6. The compound according to claim 1, wherein $R^6$ is methyl,
or a stereoisomer, a tautomer, an N-oxide, or a physiologically acceptable salt thereof, or a mixture of any of the foregoing.

7. The compound according to claim 1, wherein:
$R^5$ and $R^{5'}$ are taken together with the nitrogen atom to which they are bound to form piperidinyl, pyrrolidinyl, or azetidinyl,
or a stereoisomer, a tautomer, an N-oxide, or a physiologically acceptable salt thereof, or a mixture of any of the foregoing.

8. A method of preparing the compound of formula (I) according to claim 1, comprising reacting an intermediate compound of formula (XI):

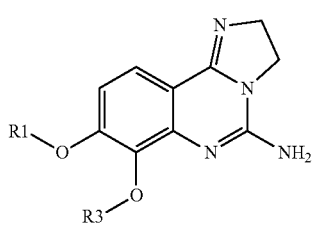

wherein $R^1$ and $R^3$ are as defined in claim 1,
with a compound of formula (XIa):
$R^2COOH$ (XIa)
wherein $R^2$ is as defined in claim 1,
to give the compound of formula (I):

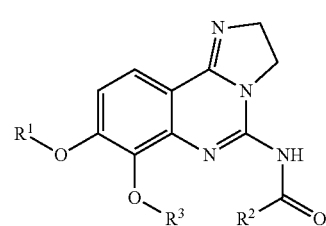

wherein $R^1$, $R^2$ and $R^3$ are as defined in claim 1.

9. A pharmaceutical composition comprising the compound of formula (I), or a stereoisomer, a tautomer, an N-oxide, or a pharmaceutically acceptable salt thereof, or a mixture of any of the foregoing, according to claim 1, and a pharmaceutically acceptable diluent or carrier.

10. A pharmaceutical combination comprising:
one or more compounds of formula (I), or a stereoisomer, a tautomer, an N-oxide, or a pharmaceutically acceptable salt thereof, or a mixture of any of the foregoing, according to claim 1; and
one or more agents selected from: a taxane, Docetaxel, Paclitaxel, or Taxol; an epothilone, Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an anti-androgen, Flutamide, Cyproterone acetate, or Bicalutamide; Bortezomib; a platinum derivative, Cisplatin, or Carboplatin; Chlorambucil; Methotrexate; and Rituximab.

11. A method for treatment of a disease of uncontrolled cell growth, proliferation or survival, an inappropriate cellular immune response, or an inappropriate cellular inflammatory response comprising administering to a human or animal in need thereof the compound of formula (I), or a stereoisomer, a tautomer, an N-oxide, or a pharmaceutically acceptable salt thereof, or a mixture of any of the foregoing, according to claim 1.

12. A compound of formula (XI):

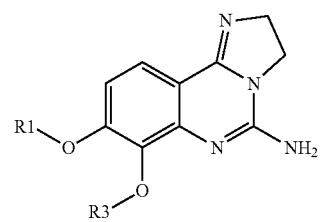

wherein $R^1$ and $R^3$ are as defined in claim 1.

13. The method according to claim 11, wherein the disease of uncontrolled cell growth, proliferation or survival, an inappropriate cellular immune response, or an inappropriate cellular inflammatory response is mediated by the phosphotidylinositol-3-kinase (PI3K) pathway.

14. The method according to claim 11, wherein the disease of uncontrolled cell growth, proliferation or survival, an inappropriate cellular immune response, or an inappropriate cellular inflammatory response is a haemotological tumour, a solid tumour or metastases thereof.

15. The method according to claim 14, wherein the haemotological tumour, solid tumour and/or metastases thereof is selected from leukaemias and myelodysplastic syndrome, malignant lymphomas, head and neck tumours, brain tumours and brain metastases, tumours of the thorax, non-small cell and small cell lung tumours, gastrointestinal tumours, endocrine tumours, mammary and other gynaecological tumours, urological tumours, renal, bladder and prostate tumours, skin tumours, and sarcomas, and metastases thereof.

* * * * *